United States Patent
Barba et al.

(10) Patent No.: US 9,017,648 B2
(45) Date of Patent: Apr. 28, 2015

(54) COSMETIC COMPOSITION COMPRISING A SUPRAMOLECULAR COMPOUND CAPABLE OF ESTABLISHING HYDROGEN BONDS, AND A PARTICULAR ADDITIONAL INGREDIENT

(75) Inventors: Claudia Barba, Paris (FR); Roberto Cavazzuti, Paris (FR)

(73) Assignee: L'Oreal, Paris (FR)

( * ) Notice: Subject to any disclaimer, the term of this patent is extended or adjusted under 35 U.S.C. 154(b) by 220 days.

(21) Appl. No.: 13/516,920

(22) PCT Filed: Dec. 15, 2010

(86) PCT No.: PCT/EP2010/069840
§ 371 (c)(1),
(2), (4) Date: Aug. 3, 2012

(87) PCT Pub. No.: WO2011/073294
PCT Pub. Date: Jun. 23, 2011

(65) Prior Publication Data
US 2013/0004438 A1    Jan. 3, 2013

Related U.S. Application Data

(60) Provisional application No. 61/289,412, filed on Dec. 23, 2009.

(30) Foreign Application Priority Data

Dec. 18, 2009 (FR) ................................ 09 59202

(51) Int. Cl.
*A61K 8/49* (2006.01)
*A61Q 1/04* (2006.01)
(Continued)

(52) U.S. Cl.
CPC .. *A61Q 1/04* (2013.01); *A61Q 1/06* (2013.01); *A61K 8/4953* (2013.01); *A61K 8/891* (2013.01); *A61K 8/90* (2013.01)

(58) Field of Classification Search
None
See application file for complete search history.

(56) References Cited

U.S. PATENT DOCUMENTS 6,517,823 B1 * 2/2003 Norman et al. ............... 424/70.7
7,378,103 B2 * 5/2008 Kanji et al. ................... 424/401
(Continued)

FOREIGN PATENT DOCUMENTS

EP    2 140 858         1/2010
EP      2140858    *    1/2010    ............... A61K 8/49
(Continued)

OTHER PUBLICATIONS

U.S. Appl. No. 13/516,901, filed Jun. 18, 2012, Barba, et al.
(Continued)

*Primary Examiner* — Brian Gulledge
(74) *Attorney, Agent, or Firm* — Oblon, McClelland, Maier & Neustadt, L.L.P.

(57) ABSTRACT

The present invention relates to a cosmetic composition comprising, in a cosmetically acceptable medium, (i) a supramolecular compound that may be obtained by reaction between: —at least one oil bearing at least one nucleophilic reactive function chosen from OH and $NH_2$, and —at least one junction group capable of establishing hydrogen bonds with one or more partner junction groups, each pairing of a junction group involving at least three hydrogen bonds, the said junction group bearing at least one isocyanate or imidazole reactive function capable of reacting with the reactive function borne by the oil, the said junction group also comprising at least one unit of formula (I) or (II): (ii) and at least one additional ingredient preferably chosen from: —silicone elastomers, —polyesters that may be obtained by reacting: a tetraol containing from 4 to 10 carbon atoms; a saturated, linear or branched monocarboxylic acid containing from 9 to 23 carbon atoms; a cyclic dicarboxylic acid containing from 6 to 12 carbon atoms; and an aromatic monocarboxylic acid containing from 7 to 11 carbon atoms, —film-forming agents chosen from silicone resins and film-forming polymers, preferably chosen from the group comprising: a film-forming block ethylenic copolymer, a vinyl polymer comprising at least one carbosiloxane dendrimer-based unit, a dispersion of acrylic or vinyl radical homopolymer or copolymer particles dispersed in the said liquid fatty phase, —structuring agents chosen from semicrystalline polymers and thickeners comprising at least one group and preferably at least two groups capable of establishing hydrogen interactions, chosen from: polymeric thickeners, and organogelling agents. The invention also relates to a cosmetic treatment process comprising the application of the said composition.

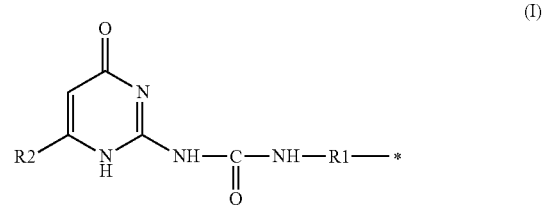

(I)

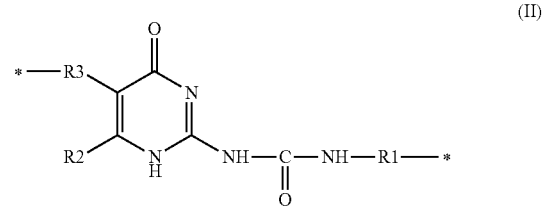

(II)

22 Claims, No Drawings

(51) Int. Cl.
  *A61Q 1/06*  (2006.01)
  *A61K 8/891*  (2006.01)
  *A61K 8/90*  (2006.01)

(56) References Cited

U.S. PATENT DOCUMENTS

2004/0161394 A1* 8/2004 Mougin et al. .............. 424/70.11
2009/0004274 A1   1/2009 Hoorne-Van Gemert et al.
2010/0028277 A1* 2/2010 Chodorowski-Kimmes
                         et al. ............................... 424/59
2010/0247466 A1   9/2010 Mougin et al.

FOREIGN PATENT DOCUMENTS

WO     02 098377      12/2002
WO     2006 118460   11/2006

OTHER PUBLICATIONS

Folmer, B. J. B., et al., "Supramolecular Polymer Materials: a Chain Extension of Telechelic Polymers Using a Reactive Hydrogen-Bonding Synthon," Advanced Materials, vol. 12, No. 12, pp. 874-878, (Jun. 16, 2000).

International Search Report Issued Apr. 28, 2011 in PCT/EP10/69840 Filed Dec. 15, 2010.

* cited by examiner

COSMETIC COMPOSITION COMPRISING A SUPRAMOLECULAR COMPOUND CAPABLE OF ESTABLISHING HYDROGEN BONDS, AND A PARTICULAR ADDITIONAL INGREDIENT

The present invention relates to a cosmetic composition, especially for caring for and/or making up keratin materials, in particular the skin or the lips, comprising novel compounds A (referred to in the context of the present patent application as supramolecular compounds) capable of establishing hydrogen bonds with partner junction groups, combined with an additional ingredient preferably chosen from:
- silicone elastomers,
- film-forming polymers,
- silicone resins,
- polycondensates,
- semicrystalline polymers,
- thickeners comprising at least one group and preferably at least two groups capable of establishing hydrogen interactions, chosen from polymeric thickeners and organogelling agents.

Many cosmetic compositions exist for which gloss properties of the deposited film, after application to keratin materials, are desired. Mention may be made, for example, of lipsticks or nail varnishes. In order to obtain such a result, it is possible to combine particular starting materials, especially lanolins, with "glossy" oils such as polybutenes, or esters of fatty acid or of fatty alcohol with a high carbon number; or alternatively certain plant oils; or alternatively esters resulting from the partial or total esterification of a hydroxylated aliphatic compound with an aromatic acid, as described in patent application EP 1 097 699.

However, obtaining gloss properties for the deposit of a cosmetic composition is occasionally associated with a tacky nature of the compositions. This tacky nature causes these formulations to leave marks on supports such as glasses and cups.

Formulators are thus in search of starting materials and/or systems for obtaining compositions whose deposit is characterized by gloss (in particular in the case of lip makeup compositions) and preferably a tack-free effect, and which are pleasant to wear (no sensation of tautness).

The aim of the present invention is to propose cosmetic compositions for obtaining such a uniform film-forming deposit on keratin materials, the said film combining good gloss properties (in particular in the case of lipsticks), gloss remanence over time (in particular 1 hour after application), which are preferably non-tacky, and which are particularly comfortable to wear (no sensation of tautness or dryness). The compositions according to the invention also allow the production of a transfer-free deposit that has a good level of remanence, in particular when it is a makeup composition, and good remanence of the colour of the deposit on keratin materials, and in particular on the skin or the lips.

One subject of the present invention is thus a cosmetic composition for making up and/or caring for keratin materials (especially the skin or the lips), comprising, in a cosmetically acceptable medium:
(i) a compound A (referred to, in the context of this patent application, as a supramolecular compound) that can be obtained by reaction between:
   at least one oil bearing at least one nucleophilic reactive function chosen from OH and NH$_2$, and
   at least one junction group capable of establishing hydrogen bonds with one or more partner junction groups, each pairing of a junction group involving at least three hydrogen bonds, the said junction group bearing at least one isocyanate or imidazole reactive function capable of reacting with the reactive function borne by the oil, the said junction group also comprising at least one unit of formula (I) or (II):

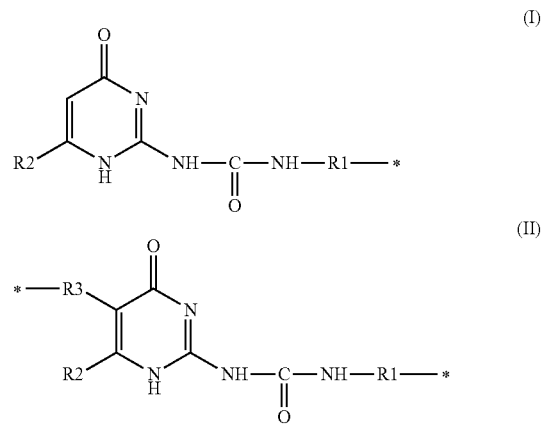

in which:
R1 and R3, which may be identical or different, represent a divalent carbon-based radical chosen from (i) a linear or branched $C_1$-$C_{32}$ alkyl group, (ii) a $C_4$-$C_{16}$ cycloalkyl group and (iii) a $C_4$-$C_{16}$ aryl group; optionally comprising 1 to 8 heteroatoms chosen from O, N, S, F, Si and P; and/or optionally substituted with an ester or amide function or with a $C_1$-$C_{12}$ alkyl radical; or a mixture of these groups;
R2 represents a hydrogen atom or a linear, branched or cyclic, saturated or unsaturated, optionally aromatic, $C_1$-$C_{32}$ carbon-based and especially hydrocarbon-based radical, which may comprise one or more heteroatoms chosen from O, N, S, F, Si and P;
(ii) combined with at least one additional ingredient preferably chosen from:
   silicone elastomers,
   polycondensates (also known as polyesters) that may be obtained by reacting:
      a tetraol containing from 4 to 10 carbon atoms;
      a saturated, linear or branched monocarboxylic acid containing from 9 to 23 carbon atoms;
      a cyclic dicarboxylic acid containing from 6 to 12 carbon atoms; and
      an aromatic monocarboxylic acid containing from 7 to 11 carbon atoms,
   film-forming agents chosen from silicone resins and film-forming polymers, preferably chosen from the group comprising:
      a film-forming block ethylenic copolymer,
      a vinyl polymer comprising at least one carbosiloxane dendrimer-based unit,
      a dispersion of acrylic or vinyl radical homopolymer or copolymer particles dispersed in the said liquid fatty phase,
   structuring agents chosen from semicrystalline polymers and thickeners comprising at least one group and preferably at least two groups capable of establishing hydrogen interactions, chosen from:
      polymeric thickeners, and
      organogelling agents.

Supramolecular Compounds:

The compounds A (also known as supramolecular compounds) functionalized according to the present invention are in the form of a solid; this makes it possible especially to form a non-tacky material, which does not transfer onto the fingers once applied to keratin materials; this is not the case for the functionalized compounds of the prior art, especially as described in U.S. Pat. No. 5,707,612, which are in the form of a more or less viscous liquid, and which form a tacky material that transfers onto the fingers after application to keratin materials.

Moreover, it has been found that crosslinking by means of four hydrogen bonds, via ureidopyrimidone groups, can increase the strength of this crosslinking, and thus improve the remanence of the desired cosmetic effect, most particularly the remanence of the deposit or of the gloss.

Furthermore, the compounds, or functionalized oils, according to the invention are easy to convey in the usual cosmetic media, especially the usual cosmetic oily media.

They are advantageously compatible with the oils usually present in cosmetic compositions, and also have good properties of dispersing pigments or fillers.

They are easy to convey in cosmetic oily or solvent media, especially oils, fatty alcohols and/or fatty esters, which facilitates their use in the cosmetic field, especially in lipsticks. They show acceptable solubility in varied cosmetic oily media, such as plant oils, alkanes, esters, whether they are short esters such as butyl or ethyl acetate, or fatty esters, and fatty alcohols, and most particularly in media comprising isododecane, parleam, isononyl isononanoate, octyldodecanol and/or a C12-C15 alkyl benzoate.

The cosmetic compositions according to the invention moreover show good applicability (glidance on application and decaking in the case of solid compositions) and good coverage; good adherence to the support, whether it is to the nails, the eyelashes, the skin or the lips; adequate flexibility and strength of the film, and also an excellent gloss durability. The comfort and glidance properties are also very satisfactory.

In general, in the context of the present patent application, the compounds A may be referred to without preference as "supramolecular compounds" for convenience and for greater clarity.

The compounds A (or supramolecular compounds) of the compositions according to the invention may be obtained by reaction between:
- at least one oil bearing at least one nucleophilic reactive function chosen from OH and $NH_2$, and
- at least one junction group capable of establishing hydrogen bonds with one or more partner junction groups, each pairing of a junction group involving at least three hydrogen bonds, the said junction group bearing at least one isocyanate or imidazole reactive function capable of reacting with the reactive function borne by the oil, the said junction group also comprising at least one unit of formula (I) or (II):

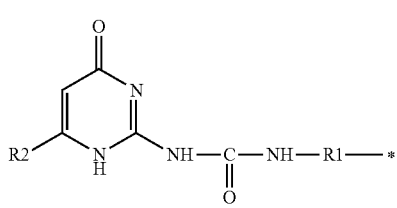

(I)

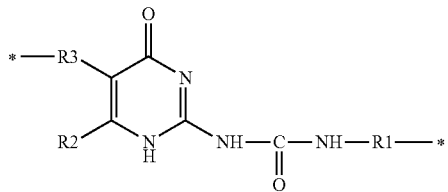

(II)

in which:
R1 and R3, which may be identical or different, represent a divalent carbon-based radical chosen from (i) a linear or branched $C_1$-$C_{32}$ alkyl group, (ii) a $C_4$-$C_{16}$ cycloalkyl group and (iii) a $C_4$-$C_{16}$ aryl group; optionally comprising 1 to 8 heteroatoms chosen from O, N, S, F, Si and P; and/or optionally substituted with an ester or amide function or with a $C_1$-$C_{12}$ alkyl radical; or a mixture of these groups;

R2 represents a hydrogen atom or a linear, branched or cyclic, saturated or unsaturated, optionally aromatic, $C_1$-$C_{32}$ carbon-based and especially hydrocarbon-based radical, which may comprise one or more heteroatoms chosen from O, N, S, F, Si and P.

In conclusion, the supramolecular compounds of the compositions according to the invention thus comprise at least one part (HB) originating from the oil and at least one part (G) originating from the junction group, the said part (G) comprising at least one unit of formula (I) or (II).

In particular, the said parts (HB) and (G) are connected via a covalent bond and may especially be connected via a covalent bond formed during the reaction between the OH and/or $NH_2$ reactive functions borne by the oil and the isocyanate reactive functions borne by the junction group; or alternatively between the $NH_2$ reactive functions borne by the oil and the isocyanate or imidazole functions borne by the junction group.

The preferential production of the compounds according to the invention may thus especially be represented schematically by the chemical reaction between the following species:

$$(HB)\text{-}(OH)_m(NH_2)_n + (G)\text{-}(NCO)_p \text{ or}$$

$$(HB)\text{-}(OH)_m(NH_2)_n + (G)\text{-}(\text{imidazole})_p \text{ with } m, n \text{ and } p$$
being non-zero integers.

The oil that may be used to prepare the compound according to the invention, which may preferably be represented schematically as $(HB)\text{-}(OH)_m(NH_2)_n$, is a fatty substance or a mixture of fatty substances, which is not crystalline at 25° C., and is liquid at room temperature and at atmospheric pressure (25° C., 1 atm.); preferably apolar or even, preferably, water-insoluble.

Preferably, the oil that may be used to prepare the supramolecular compound according to the invention is non-polymeric.

The term "liquid" means that the viscosity of the compound is less than or equal to 2500 centipoises, at 110° C. and 1 atm., measured with a Brookfield DV-I or Brookfield Cap 1000+ rheometer, a person skilled in the art selecting the machine that is suited to the viscosity measurement.

The term "apolar" means a compound whose HLB value (hydrophilic/lipophilic balance) is low; especially less than or equal to 8, preferably less than or equal to 4 and better still less than or equal to 2; preferentially, the HLB value should be low enough to make it possible to obtain a supramolecular material that is not hygroscopic, or not too hygroscopic.

The term "insoluble" means that the oil fraction that can dissolve in water, at 25° C. and 1 atm., is less than 5% by weight (i.e. 5 g of oil in 100 ml of water); preferably less than 3%.

The term "fatty substance" means especially, but not exclusively, a hydrocarbon-based compound comprising one or more saturated or unsaturated, linear, cyclic or branched alkyl chains, containing at least 6 carbon atoms and possibly comprising polar groups such as an acid, hydroxyl or polyol, amine, amide, phosphoric acid, phosphate, ester, ether, urea, carbamate, thiol, thioether or thioester group, this chain possibly containing up to 100 carbon atoms.

Preferably, the oil that may be used to prepare the compound according to the invention is a glossy oil, i.e. an oil with a refractive index of greater than or equal to 1.46 at 25° C. and in particular between 1.46 and 1.55 (the refractive index being defined relative to the sodium D line, at 25° C.)

Preferably, the oil that may be used to prepare the compound according to the invention is a non-volatile oil. The term "non-volatile oil" means an oil that is capable of remaining on keratin materials at room temperature and atmospheric pressure for at least several hours, and that especially has a vapour pressure of less than $10^{-3}$ mmHg (0.13 Pa).

Preferably, the oil has a molar mass (Mw) of between 150 and 6000, especially between 170 and 4000, or even between 180 and 2000, more preferentially between 200 and 1500 and better still between 220 and 800 g/mol.

The oil that may be used in the context of the present invention bears at least one reactive function capable of reacting with the reactive function borne on the junction group, and is especially capable of reacting chemically with the isocyanate or imidazole groups borne by the junction group; preferably, this function is an OH or $NH_2$ function. Preferably, the oil comprises only OH functions, in particular 1 to 3 OH functions, preferentially primary or secondary OH functions, and better still only primary functions.

The oil according to the present invention is preferably a carbon-based and especially a hydrocarbon-based oil, which, besides the reactive function capable of reacting with the junction group, may comprise oxygen, nitrogen, sulfur and/or phosphorus atoms. The oil is very preferentially chosen from cosmetically acceptable oils.

The oil that may be used in the context of the present invention may be chosen from:

(i) saturated or unsaturated, linear, branched or cyclic fatty alcohols containing 6 to 50 carbon atoms, comprising one or more OH; optionally comprising one or more $NH_2$.

Mention may be made in particular of:

saturated or unsaturated, linear or branched C6-C50, especially C6-C32 and in particular C8-C28 monoalcohols, and especially isostearyl alcohol, cetyl alcohol, oleyl alcohol, isopalmitoyl alcohol, 2-butyloctanol, 2-hexyldecanol, 2-octyldecanol, 2-octyldodecanol, 2-octyltetradecanol, 2-decyltetradecanol and 2-dodecylhexadecanol, and especially the alcohols sold under the name Jarcol by the company Jarchem Industries, such as Jarcol I-12, Jarcol I-16, Jarcol I-20 and Jarcol I-24;

saturated or unsaturated, linear or branched C6-C50, especially C6-C40 and in particular C8-C38 diols, and especially branched C32-C36 diols, and in particular the commercial product Pripol 2033 from Uniqema;

saturated or unsaturated, linear or branched C6-C50, especially C6-C32 and in particular C8-C28 triols, and especially phytanetriol;

(ii) esters and ethers bearing at least one free OH, and especially partial polyol esters and ethers, and hydroxylated carboxylic acid esters.

The term "partial polyol ester" means esters prepared by esterification of a polyol with a substituted or unsubstituted carboxylic acid, the reaction not being total, i.e. not performed on all of the free OHs of the polyol; as a result, the ester thus still comprises at least one free OH.

Preferably, the carboxylic acid is a monoacid. A mixture of carboxylic acids, especially monocarboxylic acids, may also be used.

The term "partial polyol ether" means ethers prepared by etherification of a polyol, with itself or with at least one other monohydroxylated or polyhydroxylated alcohol, preferably a monoalcohol, the etherification reaction not being total, i.e. not performed on all of the free OHs of the polyol; as a result, the ether still comprises at least one free OH.

The term "hydroxylated carboxylic acid ester" means (mono and poly)esters prepared by reaction between a carboxylic acid bearing at least one free OH function, and one or more (mono or polyalcohols, preferably a monoalcohol, the reaction possibly being total or partial (performed on all or some of the free OHs of the alcohol).

Among the polyols that may be used for preparing the above esters or ethers, mention may be made of propylene glycol, glycerol, neopentyl glycol, trimethylolpropane, trimethylolethane, polyglycerols and especially polyglycerol-2, polyglycerol-3 and polyglycerol-10; erythritol, dipentaerythritol, pentaerythritol, bis(trimethylolpropane), phytanetriol, sucrose, glucose, methylglucose, sorbitol, fructose, xylose, mannitol or glucosamine; and also diol dimers obtained especially from fatty acid dimers, especially branched aliphatic and/or alicyclic C32-C38 and especially C36 diols, such as those defined in the article Hofer et al., European Coating Journal (March 2000), pages 26-37; and mixtures thereof.

Among the monoalcohols that may be used for preparing the above esters or ethers, mention may be made of linear or branched, preferably branched, C3-C50 alcohols, and especially 2-ethylhexanol, octanol and isostearyl alcohol, and mixtures thereof.

Among the carboxylic acids that may be used for preparing the above esters or ethers, mention may be made of linear or branched, saturated or unsaturated monoacids containing 6 to 50 carbon atoms and diacids containing 3 to 12 carbon atoms, among which mention may be made of octylneodecanoic acid, hexyldecanoic acid, ethylhexanoic acid, isostearic acid, nonanoic acid, isononanoic acid, arachidic acid, stearic acid, palmitic acid, oleic acid, oxalic acid, adipic acid, succinic acid, fumaric acid, maleic acid, capric acid, hexanedioic acid and decanoic acid, and mixtures thereof.

Among the hydroxylated carboxylic acids that may be used for preparing the above esters or ethers, mention may be made of monohydroxylated or polyhydroxylated acids, preferably monohydroxylated acids, containing for example 4 to 28 carbon atoms, and especially 12-hydroxystearic acid, ricinoleic acid, malic acid, lactic acid and citric acid; and mixtures thereof.

Thus, the oil that may be used in the present invention may be chosen, alone or as a mixture, from:

pentaerythritol partial esters, and especially pentaerythrityl adipate, pentaerythrityl caprate, pentaerythrityl succinate, pentaerythrityl tetraisononanoate, pentaerythrityl triisononanoate, pentaerythrityl tetraisostearate, pentaerythrityl triisostearate, pentaerythrityl 2-(tetradecyl)-tetradecanoate, pentaerythrityl (tetraethyl) hexanoate and pentaerythrityl (tetraoctyl)dodecanoate;

dipentaerythritol diesters, triesters, tetraesters or pentaesters, and especially dipentaerythrityl pentaisononanoate, dipentaerythrityl pentaisostearate, dipentaerythrityl tetraisostearate and dipentaerythrityl tris (polyhydroxystearate);

trimethylolpropane monoesters and diesters, for instance trimethylolpropane monoisostearate, trimethylolpropane diisostearate, trimethylolpropane mono-2-ethylhexanoate and trimethylolpropane bis(2-ethylhexanoate);

bis(trimethylolpropane) monoesters, diesters and triesters, for instance bis(trimethylolpropane) diisostearate, bis(trimethylolpropane) triisostearate and bis(trimethylolpropane) triethylhexanoate;

partial monoesters or polyesters of glycerol or of polyglycerols, and especially:
  glyceryl diisostearate and glyceryl diisononanoate;
  polyglycerol-2 monoesters, diesters and triesters; for example with isostearic acid, 2-ethylhexanoic acid and/or isononanoic acid; and especially polyglyceryl-2 isostearate; polyglyceryl-2 diisostearate; polyglyceryl-2 triisostearate; polyglyceryl-2 nonaisostearate; polyglyceryl-2 nonanoate;
  polyglycerol-3 monoesters, diesters, triesters or tetraesters; for example with either isostearic acid, 2-ethylhexanoic acid and/or isononanoic acid; and especially polyglyceryl-3 isostearate; polyglyceryl-3 diisostearate; polyglyceryl-3 triisostearate; polyglyceryl-3 nonaisostearate; polyglyceryl-3 nonanoate;
  polyglycerol-10 partial esters and in particular polyglyceryl-10 nonaisostearate; polyglyceryl-10 nonanoate; polyglyceryl-10 isostearate; polyglyceryl-10 diisostearate; polyglyceryl-10 triisostearate;

propylene glycol monoesters, for instance propylene glycol monoisostearate, propylene glycol neopentanoate or propylene glycol monooctanoate;

diol dimer monoesters, for instance isostearyl dimer dilinoleate and octyldodecyl dimer dilinoleate;

glycerol ethers, such as polyglyceryl-2 oleyl ether, polyglyceryl-3 cetyl ether, polyglyceryl-3 decyl tetradecyl ether and polyglyceryl-2 stearyl ether;

esters between a hydroxylated monocarboxylic, dicarboxylic or tricarboxylic acid and monoalcohols, and in particular:
  esters, especially monoesters, of 12-hydroxystearic acid; such as octyl hydroxystearate and 2-octyldodecyl hydroxystearate; mention may also be made of the corresponding oligomeric polyhydroxystearates, especially having a degree of polymerization of from 1 to 10, bearing at least one residual OH;
  lactic acid esters, and especially C4-40 alkyl lactates, such as 2-ethylhexyl lactate, diisostearyl lactate, isostearyl lactate, isononyl lactate or 2-octyldodecyl lactate;
  malic acid esters, and especially C4-40 alkyl malates, such as bis(2-ethylhexyl) malate, diisostearyl malate or bis(2-octyldodecyl) malate;
  citric acid esters, and especially C4-40 alkyl citrates, such as triisostearyl citrate, triisocetyl citrate and triisoarachidyl citrate;

(iii) hydroxylated natural oils, modified natural oils and plant oils, and especially:
  triglyceryl esters bearing one or more OHs;
  hydrogenated or non-hydrogenated castor oil, and also derivatives thereof derived especially from the transesterification of castor oil; for instance the products Polycin M-365 or Polycin 2525 sold by Vertellus;
  modified epoxidized oils, the modification consisting in opening the epoxy function to obtain a diol, and especially hydroxylated modified soybean oil; hydroxylated soybean oils (directly hydroxylated or epoxidized beforehand); and especially the oils Agrol 2.0, Agrol 3.0 and Agrol 7.0 sold by Bio-Based Technologies, LLC; the oil Soyol R2-052 from the company Urethane Soy System; the Renuva oils sold by Dow Chemical; the oils BioH Polyol 210 and 500 sold by Cargill.

According to a first particularly preferred embodiment, the oil that may be used to prepare the supramolecular compound in the context of the present invention is chosen from linear, branched or cyclic, saturated or unsaturated fatty alcohols, comprising 6 to 50 carbon atoms, comprising one or more OH; optionally comprising one or more $NH_2$, such as:
  saturated or unsaturated, linear or branched C6-C50, especially C6-C32 and in particular C8-C28 monoalcohols, and especially isostearyl alcohol, cetyl alcohol, oleyl alcohol, isopalmitoyl alcohol, 2-butyloctanol, 2-hexyldecanol, 2-octyldodecanol, 2-octyldodecanol, 2-octyltetradecanol, 2-decyltetra-decanol and 2-dodecylhexadecanol, and especially the alcohols sold under the name Jarcol by the company Jarchem Industries, such as Jarcol I-12, Jarcol I-16, Jarcol I-20 and Jarcol I-24;
  saturated or unsaturated, linear or branched, C6-C50, especially C6-C40 and in particular C8-C38 diols, and especially branched C32-36 diols, and in particular the commercial product Pripol 2033 from Uniqema;
  saturated or unsaturated, linear or branched C6-C50, especially C6-C32 and in particular C8-C28 triols, and especially phytanetriol.

According to this first preferred embodiment, the oil that may be used to prepare the supramolecular compound in the context of the present invention is preferably chosen from linear or branched, saturated or unsaturated C6-C50, especially C6-C32 and in particular C8-C28 monoalcohols, and especially isostearyl alcohol, cetyl alcohol, oleyl alcohol, isopalmitoyl alcohol, 2-butyloctanol, 2-hexyldecanol, 2-octyldodecanol, 2-octyldodecanol, 2-octyltetradecanol, 2-decyltetra-decanol and 2-dodecylhexadecanol, and especially the alcohols sold under the name Jarcol by the company Jarchem Industries, such as Jarcol I-12, Jarcol I-16, Jarcol I-20 and Jarcol I-24.

According to a second particularly preferred embodiment, the oil that may be used to prepare the supramolecular compound in the context of the present invention is chosen from esters between a hydroxylated mono-, di- or tricarboxylic acid and monoalcohols, and in particular:
  esters, especially monoesters, of 12-hydroxystearic acid; such as octyl hydroxystearate and 2-octyldodecyl hydroxystearate; mention may also be made of the corresponding oligomeric polyhydroxystearates, especially with a degree of polymerization of from 1 to 10, containing at least one residual OH;
  lactic acid esters, especially C4-40 alkyl lactates, such as 2-ethylhexyl lactate, diisostearyl lactate, isostearyl lactate, isononyl lactate and 2-octyldodecyl lactate;
  malic acid esters, and especially C4-40 alkyl malates, such as 2-diethylhexyl malate, diisostearyl malate and 2-dioctyldodecyl malate;
  citric acid esters, and especially C4-40 alkyl citrates, such as triisostearyl citrate, triisocetyl citrate and triisoarachidyl citrate.

According to this second preferred embodiment, the oil that may be used in the context of the present invention is preferably chosen from esters between a hydroxylated dicarboxylic acid and monoalcohols, and in particular of malic acid, and especially C4-40 alkyl malates, such as 2-diethylhexyl malate, diisostearyl malate and 2-dioctyldodecyl malate.

In particular, when glossy oils are used, the following glossy oils, the refractive index of which at 25° C. is indicated in parentheses, may be used: polyglyceryl-3 diisostearate (1.472), phytanetriol (1.467), castor oil (1.475), 2-octyldodecanol (1.46), oleyl alcohol (1.461), octyl hydroxystearate (1.46), polyglyceryl-2 isostearate (1.468), polyglyceryl-2 diisostearate (1.464), diisostearyl malate (1.462), 2-butyloctanol, 2-hexyldecanol (1.45), 2-decyltetra-decanol (1.457), and also mixtures thereof.

Preferably, the oils that may be used in the present invention are chosen from 2-octyldodecanol, diisostearyl malate, 2-butyloctanol, 2-hexyldecanol, 2-decyltetradecanol; hydrogenated or non-hydrogenated castor oil, and also derivatives thereof; hydroxylated modified soybean oil, and mixtures thereof.

Junction Group

The junction group that may be used to form the supramolecular compound of the compositions according to the invention bears at least one reactive group, especially isocyanate or imidazole, capable of reacting with the reactive functions, especially OH and/or $NH_2$ (exclusively $NH_2$ for imidazole), of the oil, so as to form a covalent bond, especially of urethane type, between the said oil and the said junction group.

Preferably, the junction group that may be used to form the supramolecular compound of the compositions according to the invention bears at least one reactive group, especially isocyanate.

The said junction group is capable of establishing H bonds with one or more partner junction groups, of identical or different chemical nature, each junction group pairing involving at least 3 H (hydrogen) bonds, preferably at least 4 H bonds and preferentially 4 H bonds.

For the purposes of the invention, the term "junction group" means any functional group comprising groups that are H bond donors or acceptors, and that are capable of establishing at least 3 H bonds, preferably at least 4 H bonds, preferentially 4 H bonds, with an identical or different partner junction group.

For the purposes of the invention, the term "partner junction group" means any junction group that can establish H bonds with one or more junction groups of the same or of another polymer according to the invention. The junction groups may be of identical or different chemical nature. If they are identical, they may then establish H bonds between themselves and are then referred to as self-complementary junction groups. If they are different, they are chosen such that they are complementary with respect to H interactions.

The said junction group, bearing isocyanate groups, may thus be represented schematically as $(G)(NCO)_p$, p being a non-zero integer, preferably equal to 1 or 2.

The junction group moreover comprises at least one monovalent unit of formula (I) and/or at least one divalent unit of formula (II), as defined below:

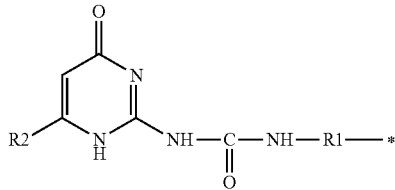
(I)

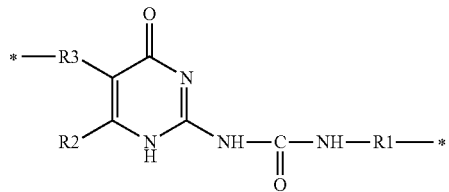
(II)

in which:
R1 and R3, which may be identical or different, represent a divalent carbon-based radical chosen from (i) a linear or branched $C_1$-$C_{32}$ alkyl group, (ii) a $C_4$-$C_{16}$ cycloalkyl group and (iii) a $C_4$-$C_{16}$ aryl group; optionally comprising 1 to 8 heteroatoms chosen from O, N, S, F, Si and P; and/or optionally substituted with an ester or amide function or with a $C_1$-$C_{12}$ alkyl radical; or a mixture of these groups;
R2 represents a hydrogen atom or a linear, branched or cyclic, saturated or unsaturated, optionally aromatic, C1-C32 carbon-based and especially hydrocarbon-based (alkyl) radical, which may comprise one or more heteroatoms chosen from O, N, S, F, Si and P.

Preferably, the junction group moreover comprises at least one monovalent unit of formula (I).

The radical R1 may especially be:
a linear or branched, divalent C2-C12 alkylene group, especially a 1,2-ethylene, 1,6-hexylene, 1,4-butylene, 1,6-(2,4,4-trimethylhexylene), 1,4-(4-methylpentylene), 1,5-(5-methylhexylene), 1,6-(6-methylheptylene), 1,5-(2,2,5-trimethylhexylene) or 1,7-(3,7-dimethyloctylene) group;
a divalent C4-C12 cycloalkylene or arylene group, chosen especially from the following radicals: -isophorone-, tolylene, 2-methyl-1,3-phenylene, 4-methyl-1,3-phenylene; 4,4'-methylenebiscyclohexylene; 4,4-bisphenylenemethylene; or of structure:

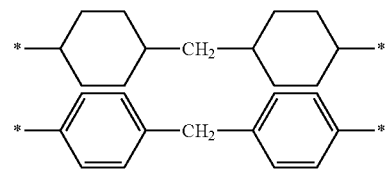

The term "-isophorone-" means the divalent radical having the structure:

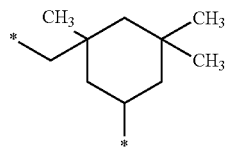 [SMILES: *CC1(C)CC(*)CC(C)(C)C1]

Preferentially, R1 represents -isophorone-, —$(CH_2)_6$— or 4,4'-methylenebiscyclohexylene.

The radical R2 may especially be H or:
a $C_1$-$C_{32}$, in particular $C_1$-$C_{16}$ or even $C_1$-$C_{10}$ alkyl group;
a $C_4$-$C_{12}$ cycloalkyl group;
a $C_4$-$C_{12}$ aryl group;
a ($C_4$-$C_{12}$)aryl($C_1$-$C_{18}$)alkyl group;
a $C_1$-$C_4$ alkoxy group;

an arylalkoxy group, in particular an aryl($C_1$-$C_4$)alkoxy group;

a $C_4$-$C_{12}$ heterocycle;

or a combination of these radicals, which may be optionally substituted with an amino, ester and/or hydroxyl function.

Preferably, R2 represents H, $CH_3$, ethyl, $C_{13}H_{27}$, $C_7H_{15}$, phenyl, isopropyl, isobutyl, n-butyl, tert-butyl, n-propyl or —CH($C_2H_5$)($C_4H_9$).

Preferably, R3 represents a divalent radical —R'3-O—C(O)—NH—R'4- in which R'3 and R'4, which may be identical or different, represent a divalent carbon-based radical chosen from a linear or branched $C_1$-$C_{32}$ alkyl group, a $C_4$-$C_{16}$ cycloalkyl group and a $C_4$-$C_{16}$ aryl group; or a mixture thereof.

In particular, R'3 and R'4 may represent methylene, 1,2-ethylene, 1,6-hexylene, 1,4-butylene, 1,6-(2,4,4-trimethylhexylene), 1,4-(4-methylpentylene), 1,5-(5-methylhexylene); 1,6-(6-methylheptylene); 1,5-(2,2,5-trimethylhexylene), 1,7-(3,7-dimethyloctylene); 4,4'-methylenebiscyclohexylene; 2-methyl-1,3-phenylene; 4-methyl-1,3-phenylene; 4,4'-bisphenylenemethylene; 1,2-tolylene, 1,4-tolylene, 2,4-tolylene, 2,6-tolylene; 1,5-naphthylene; tetramethylxylylene; isophorone.

Most particularly, R'3 may represent a C1-C4 alkylene, especially 1,2-ethylene.

Preferably, R'4 may represent the divalent radical derived from isophorone.

Most particularly, R3 may have the structure:

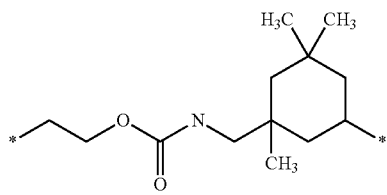 [SMILES: *CCOC(=O)NCC1(C)CC(*)CC(C)(C)C1]

In a particularly preferred manner, the following may apply in formula (I):

$R_1$=-isophorone-, $R_2$=methyl, which gives the unit of formula:

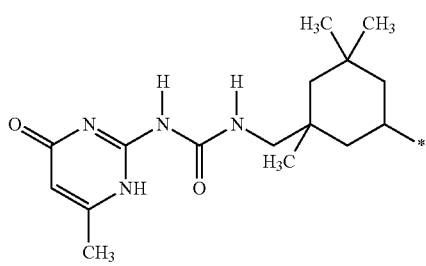

$R_1$=—($CH_2$)$_6$—, $R_2$=methyl, which gives the unit of formula:

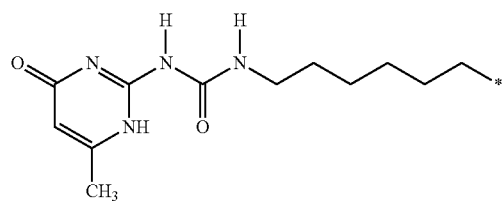

$R_1$=—($CH_2$)$_6$—, $R_2$=isopropyl, which gives the unit of formula:

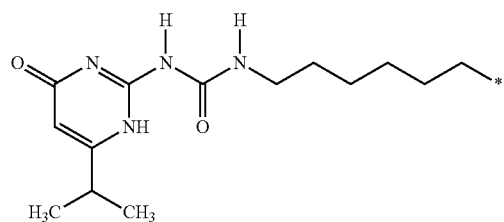

$R_1$=4,4'-methylenebiscyclohexylene and $R_2$=methyl, which gives the unit of formula:

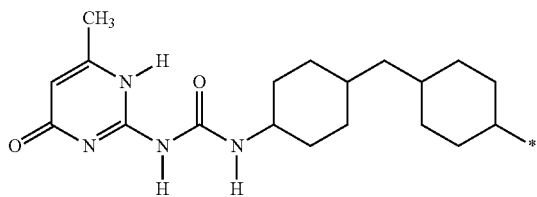

In a particularly preferred manner, in formula (II), R1 may represent the -isophorone-radical, R2=methyl and R3=—($CH_2$)$_2$OCO—NH-isophorone-, which gives the divalent unit of formula:

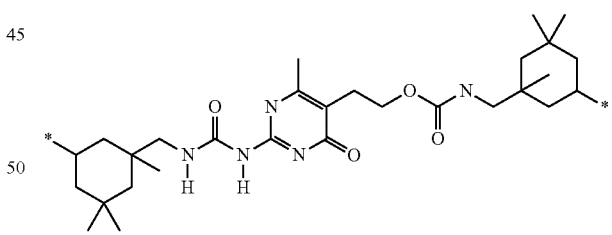

The junction groups bearing only one isocyanate function may have the formula:

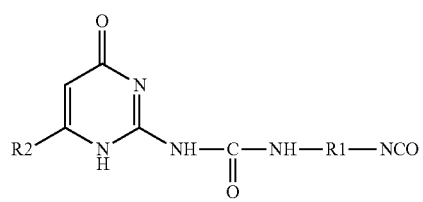

in which R1 and R2 are as defined above; and in particular:
R1 represents -isophorone-, —(CH$_2$)$_6$—, —CH$_2$CH(CH$_3$)—CH$_2$—C(CH$_3$)$_2$—CH$_2$—CH$_2$, 4,4'-methylenebiscyclo-hexylene or 2-methyl-1,3-phenylene; and/or
R2 represents H, CH$_3$, ethyl, C$_{13}$H$_{27}$, C$_7$H$_{15}$, phenyl, isopropyl, isobutyl, n-butyl, tert-butyl, n-propyl or —CH(C$_2$H$_5$)(C$_4$H$_9$).

Preferably, the junction groups may be chosen from the following groups:

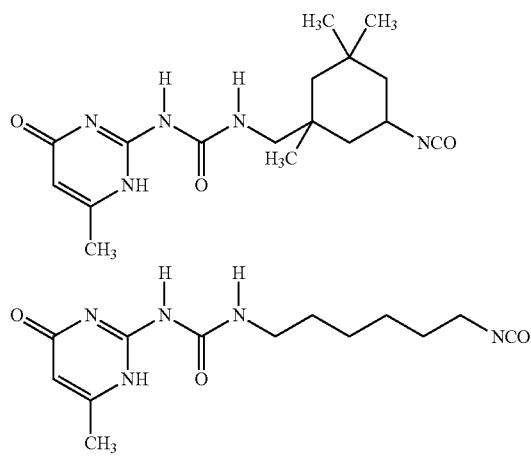

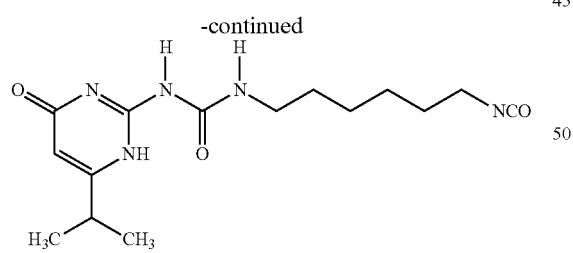

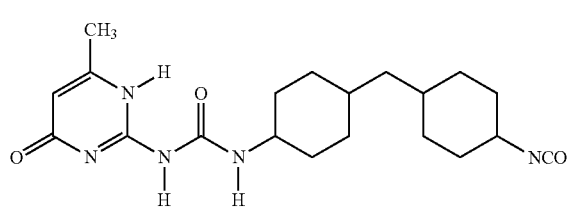

The junction groups bearing two isocyanate functions may have the formula:

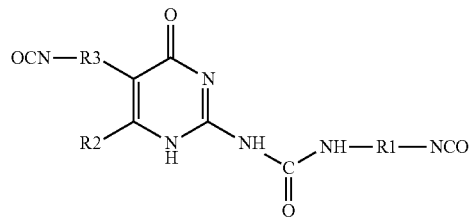

in which R1, R2 and R3 are as defined above, and in particular:
R1 represents -isophorone-, —(CH$_2$)$_2$—, —(CH$_2$)$_6$—, —CH$_2$CH(CH$_3$)—CH$_2$—C(CH$_3$)$_2$—CH$_2$—CH$_2$, 4,4'-methylenebiscyclo-hexylene or 2-methyl-1,3-phenylene; and/or
R2 represents H, CH$_3$, ethyl, C$_{13}$H$_{27}$, C$_7$H$_{15}$, phenyl, isopropyl, isobutyl, n-butyl, tert-butyl, n-propyl or —CH(C$_2$H$_5$)(C$_4$H$_9$); and/or
R3 represents a divalent radical —R'3-O—C(O)—NH—R'4- in which R'3 and R'4, which may be identical or different, represent a divalent carbon-based radical chosen from a linear or branched C$_1$-C$_{30}$ alkyl group, a C$_4$-C$_{12}$ cycloalkyl group and a C$_4$-C$_{12}$ aryl group; or a mixture thereof; and especially R'3 represents a C$_1$-C$_4$ alkylene, especially 1,2-ethylene, and R'4 represents the divalent radical derived from isophorone.

A junction group that is most particularly preferred is the one having the formula:

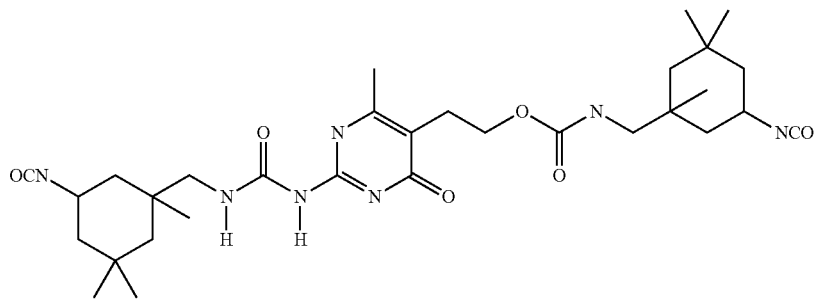

Among the junction groups bearing an imidazole group, mention may be made of the following compound:

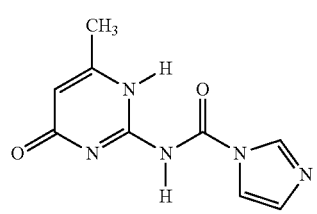 [SMILES: Cc1cc(=O)nc(NC(=O)n2ccnc2)[nH]1]

According to one particular embodiment of the invention, the junction groups may be attached to the oil by functionalization of the junction group with an isocyanate or imidazole.

According to another embodiment, it is possible to perform the reverse reaction by prefunctionalizing the oil with a diisocyanate.

As mentioned above (first mode), the compound according to the invention may thus result from the chemical reaction between an oil (HB)-(OH)$_m$(NH$_2$)$_n$ and a junction group (G)-(NCO)$_p$ or (G)-(imidazole)$_p$.

Preferably, the oil comprises only hydroxyl functions and the junction group comprises 1 or 2 isocyanate functions, which leads to the following reactions:

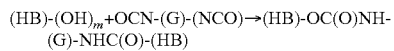

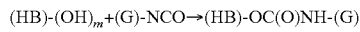

with m=integer greater than or equal to 1.

Preferably, the degree of grafting of the free OHs of the oil is between 1% and 100%, especially between 20% and 99% and better still between 50% and 95%; preferably, this degree is 100% (all the free OHs are functionalized with a junction group), especially when the oil initially comprises only one OH function.

The supramolecular compound according to the invention may be prepared via the processes usually used by those skilled in the art for forming a urethane bond, between the free OH functions of the oil and the isocyanate functions borne by the junction group. By way of illustration, a general preparation process consists in:

ensuring that the oil to be functionalized does not comprise any residual water, heating the oil comprising at least one reactive function, especially OH, to a temperature that may be between 60° C. and 140° C.;

adding the junction group bearing the reactive functions, especially isocyanate;

optionally stirring the mixture, under a controlled atmosphere, at a temperature of about 100-130° C.; for 1 to 24 hours;

monitoring by infrared spectroscopy the disappearance of the characteristic band for isocyanates (between 2500 and 2800 cm$^{-1}$) so as to stop the reaction at the total disappearance of the peak, and then to allow the final product to cool to room temperature.

The reaction may be performed in the presence of a solvent, especially methyltetrahydrofuran, tetrahydro-furan, toluene or butyl acetate; the reaction may also be performed without solvent, in which case the oil may serve as solvent.

It is also possible to add a conventional catalyst for the formation of a urethane bond. An example that may be mentioned is dibutyltin dilaurate.

Finally, the supramolecular compound may be washed and dried, or even purified, according to the general knowledge of a person skilled in the art.

According to the second embodiment, the reaction may include the following steps:

(i) functionalization of the oil with a diisocyanate according to the reaction scheme:

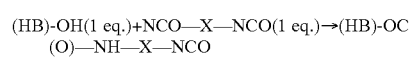

and then (iia) either reaction with 6-methylisocytosine:

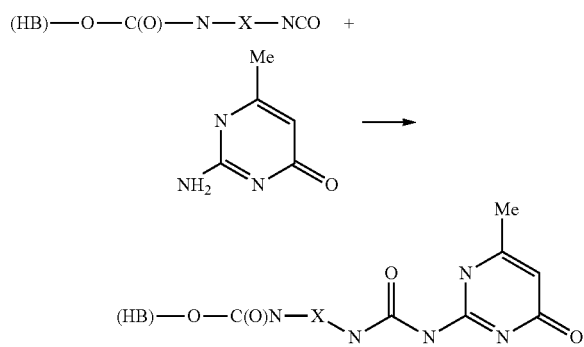

or (iib) reaction with 5-hydroxyethyl-6-methylisocytosine:

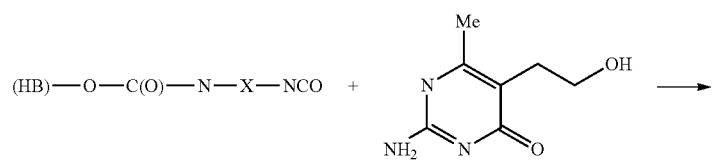

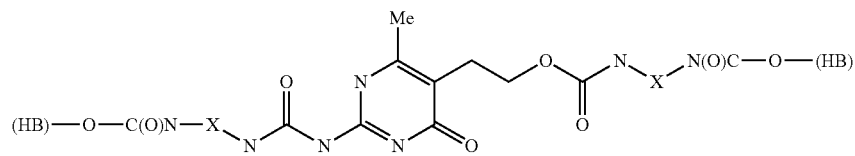

An illustration of such a reaction is given in Folmer et al., Adv. Mater., 12, 874-78 (2000).

The supramolecular compounds of the compositions according to the invention may especially correspond to the following structures:

ureidopyrimidone-functionalized octyldodecanol of structure:

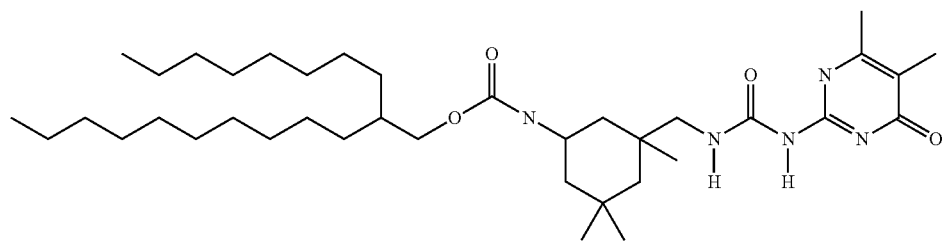
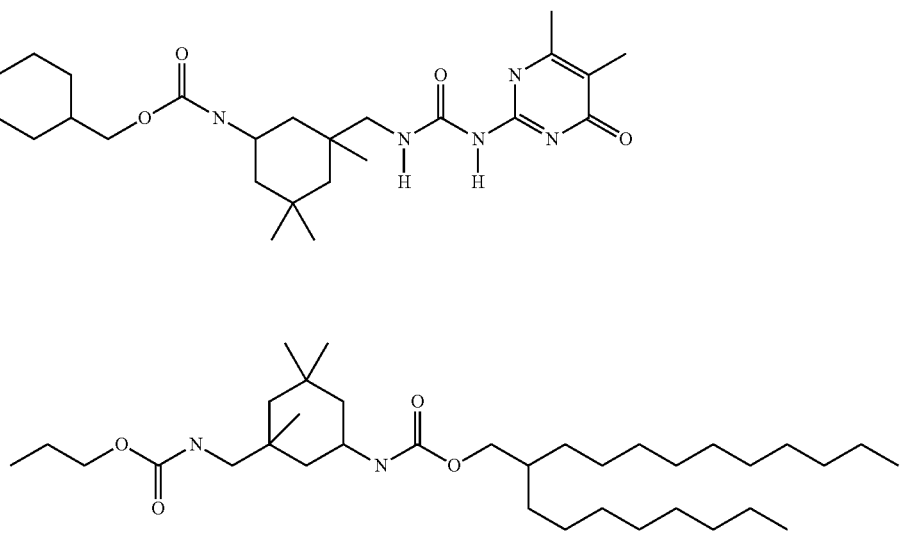
or of structure:
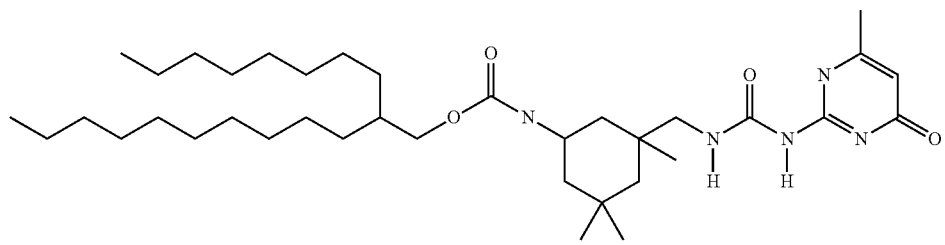 [SMILES: CCCCCCCCCCC(CCCCCCCC)COC(=O)NC1CC(C)(C)CC(C)(CNC(=O)Nc2nc(=O)cc(C)[nH]2)C1]
ureidopyrimidone-functionalized diisostearyl malate of structure:
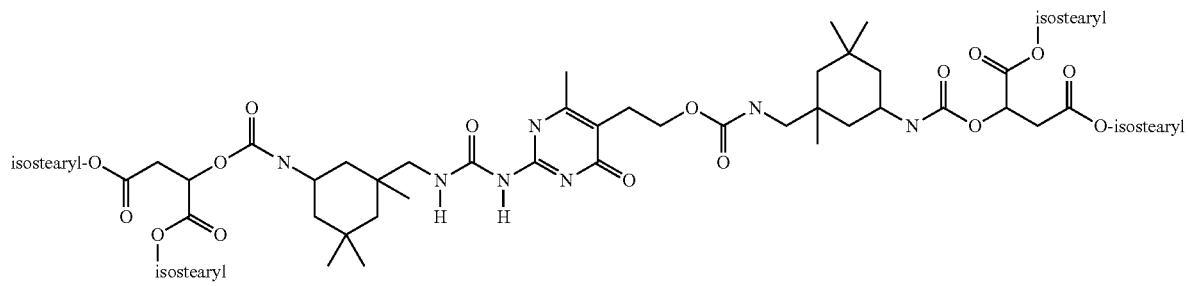

or of structure:
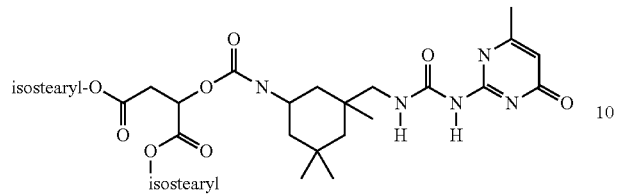
ureidopyrimidone-functionalized castor oil of structure:
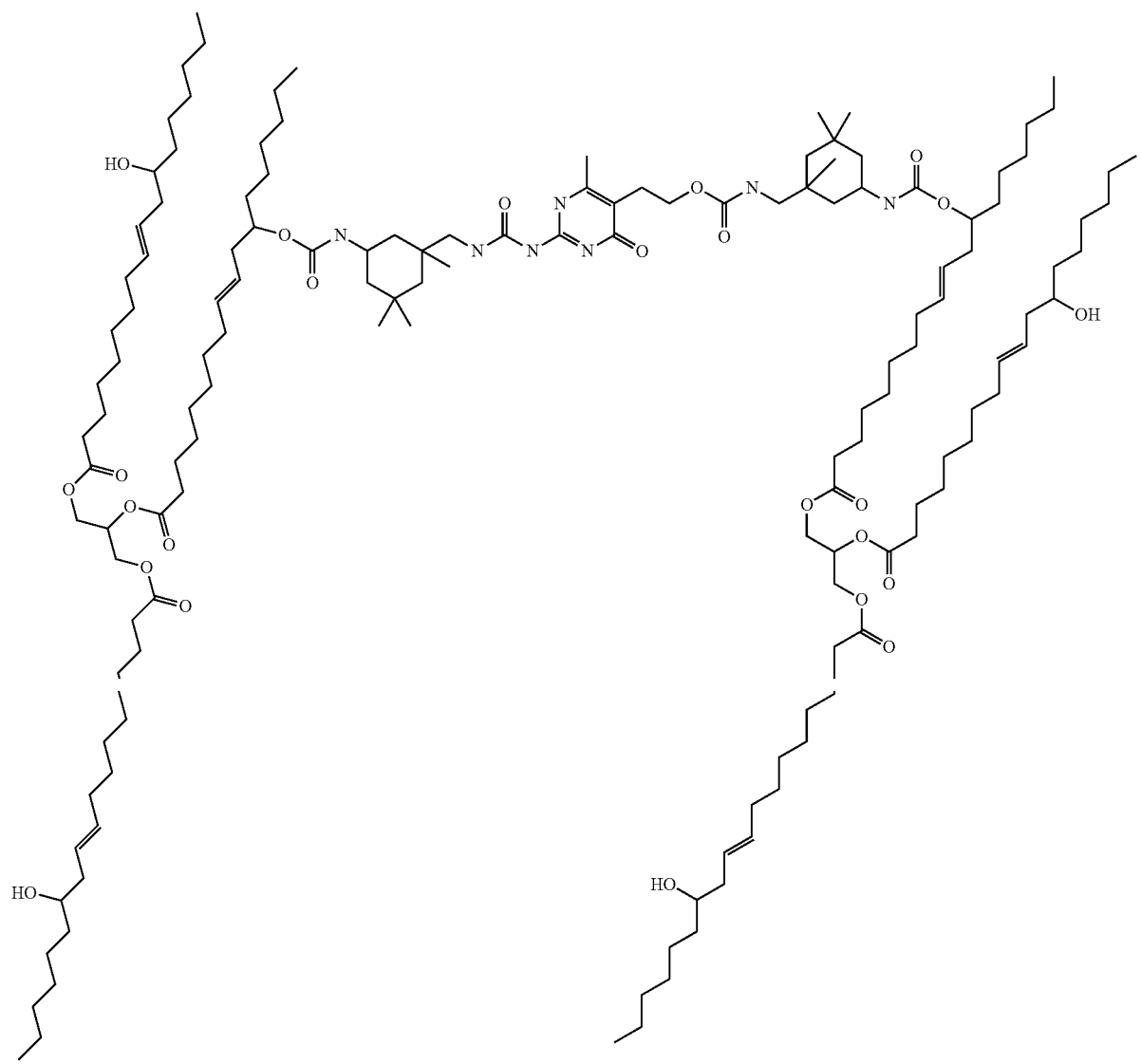

or of structure:
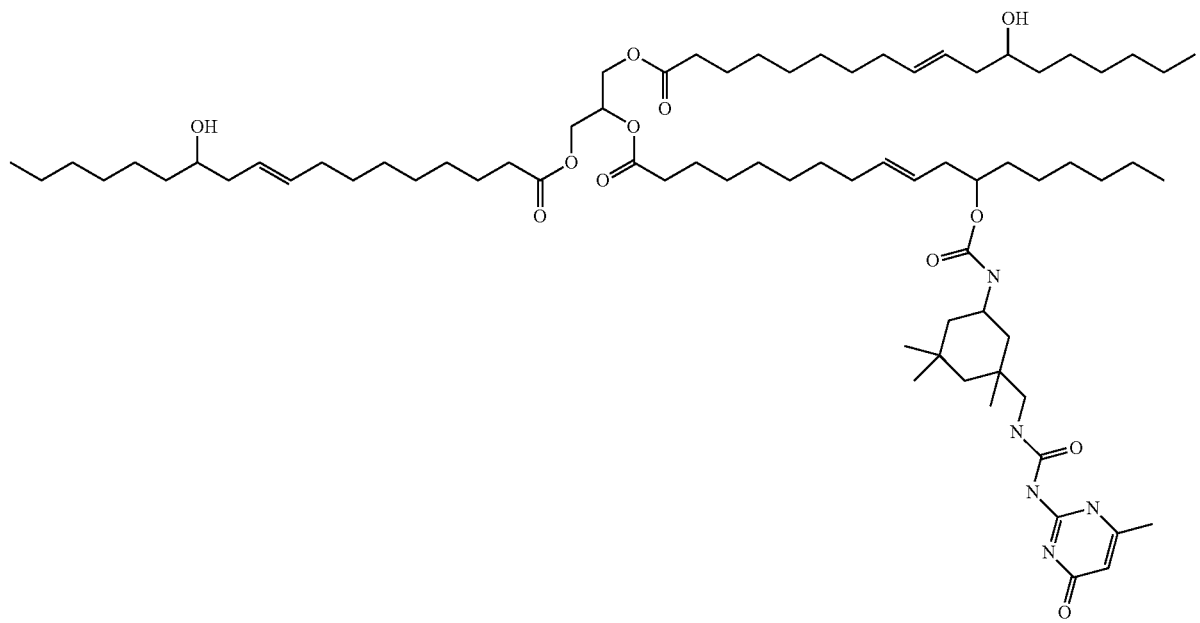 [SMILES: CCCCCCC(O)C/C=C/CCCCCCCC(=O)OCC(COC(=O)CCCCCCC/C=C/CC(O)CCCCCC)OC(=O)CCCCCCC/C=C/CC(CCCCCC)OC(=O)NC1CC(C)(C)CC(C)(CNC(=O)Nc2nc(=O)cc(C)[nH]2)C1]
ureidopyrimidone-functionalized 2-hexyldodecanol of structure:
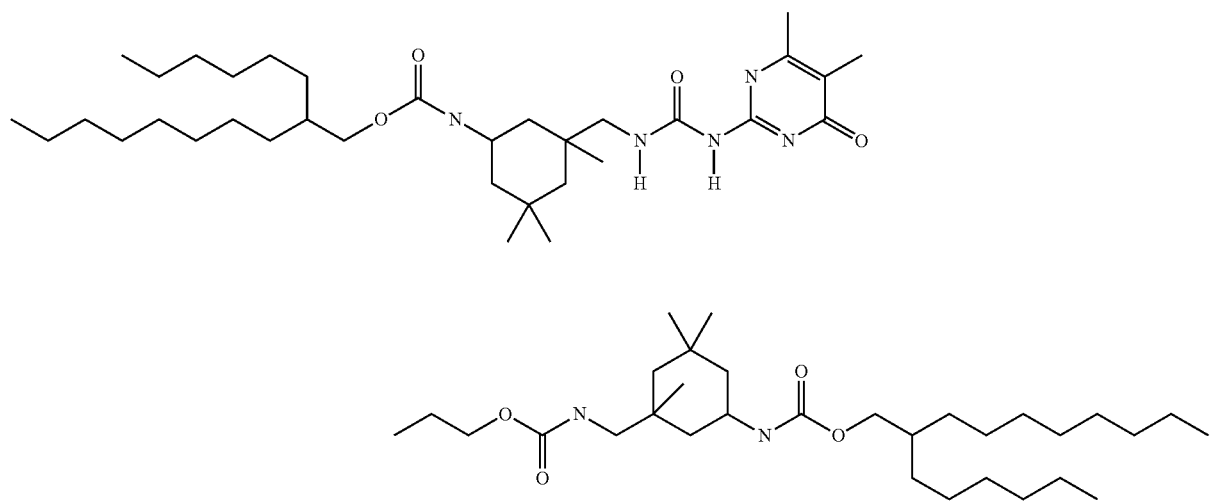
or of structure:
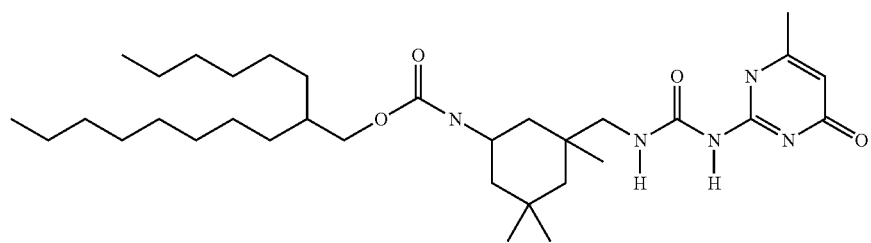 [SMILES: CCCCCCCCC(CCCCCC)COC(=O)NC1CC(C)(C)CC(C)(CNC(=O)Nc2nc(=O)cc(C)[nH]2)C1]

ureidopyrimidone-functionalized 2-decyltetra-decanol of structure:

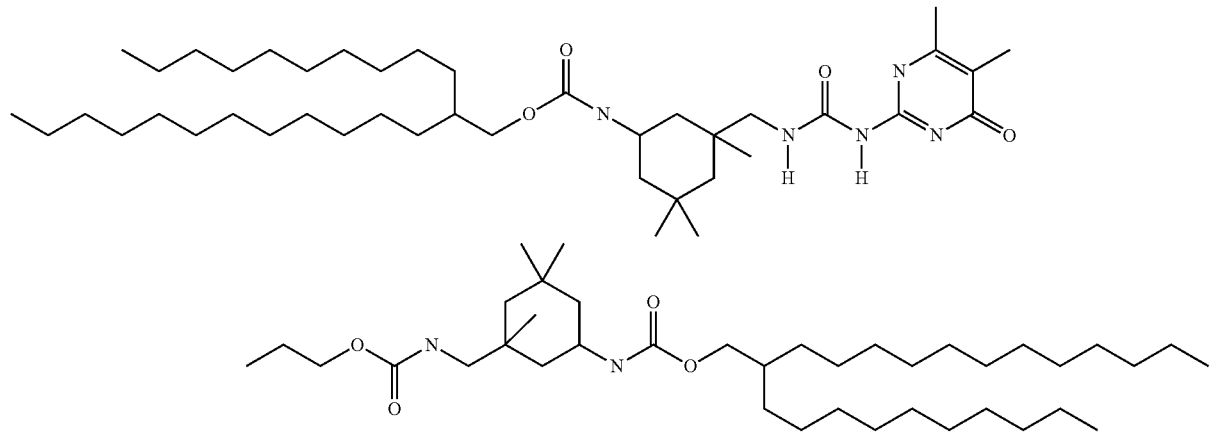

or of structure:

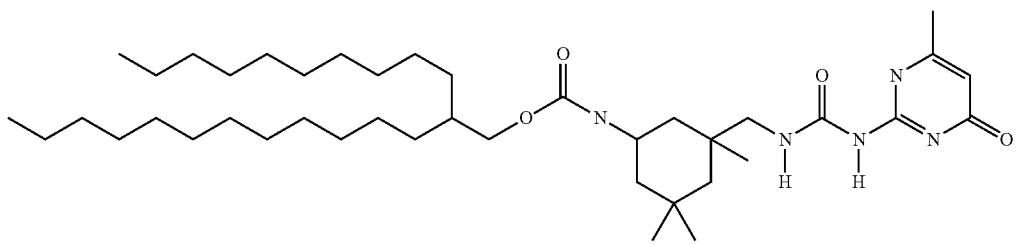 [SMILES: CCCCCCCCCCCCC(CCCCCCCCCC)COC(=O)NC1CC(C)(C)CC(C)(CNC(=O)Nc2nc(=O)cc(C)[nH]2)C1]

It has been found that the use of the compounds according to the invention may lead, after application of the composition to keratin materials, to the formation of a supramolecular polymer in the form of a physically crosslinked network, especially by means of hydrogen bonds, which is generally in the form of a film, and which has very good mechanical strength.

For the purposes of the invention, the term "supramolecular polymer" means a polymer chain or network formed from the assembly of non-polymeric compounds according to the invention with at least one other identical or different non-polymeric compound according to the invention, each assembly comprising at least one pair of identical or different paired junction groups.

For the purposes of the invention the term "pair of paired junction groups" means two junction groups, each of which may optionally be borne by the same compound according to the invention, the two groups being connected together via 4 H bonds.

Thus, the supramolecular polymer will have points of physical crosslinking provided by the H bonds between these pairs of junction groups. The physical crosslinking will ensure the maintenance and persistence of the cosmetic effect in a similar manner to chemical crosslinking, while at the same time allowing reversibility, i.e. the possibility of totally removing the deposit.

Preferably, the supramolecular compound according to the invention has a viscosity, measured at 125° C., of between 30 and 6000 mPa·s, especially between 150 and 4000 mPa·s, or even between 500 and 3500 mPa·s and better still between 750 and 3000 mPa·s.

The number-average molecular mass (Mn) of the supramolecular compound according to the invention is preferably between 180 and 8000, preferably from 200 to 6000, or even from 300 to 4000, better still from 400 to 3000 and preferentially from 500 to 1500.

The supramolecular compound according to the invention is advantageously soluble in the cosmetic oily media usually used, especially in plant oils, C6-C32 alkanes, C8-C32 fatty esters, C2-C7 short esters, C8-C32 fatty alcohols, and more particularly in media comprising at least isododecane, Parleam, isononyl isononanoate, octyldodecanol, a C12-C15 alkyl benzoate, butyl acetate or ethyl acetate, alone or as a mixture.

The term "soluble" means that the compound forms a clear solution in at least one solvent chosen from isododecane, Parleam, isononyl isononanoate, octyldodecanol, a C12-C15 alkyl benzoate, butyl acetate or ethyl acetate, in a proportion of at least 50% by weight, at 25° C.

The supramolecular compounds according to the invention may be used advantageously in a cosmetic composition, which moreover comprises a cosmetically acceptable medium, i.e. a medium that is compatible with keratin materials such as facial or bodily skin, the eyelashes, the eyebrows, the lips and the nails.

Preferably, the composition according to the invention has a content of supramolecular compound of between 5% and 95% by weight, preferably between 10% and 95% by weight and better still preferably between 20% and 90% by weight relative to the total weight of the composition.

As examples of supramolecular compounds that may be used in the compositions according to the invention, mention may be made of the following compounds:

COMPOUND 1

Ureidopyrimidone-functionalized Octyldodecanol

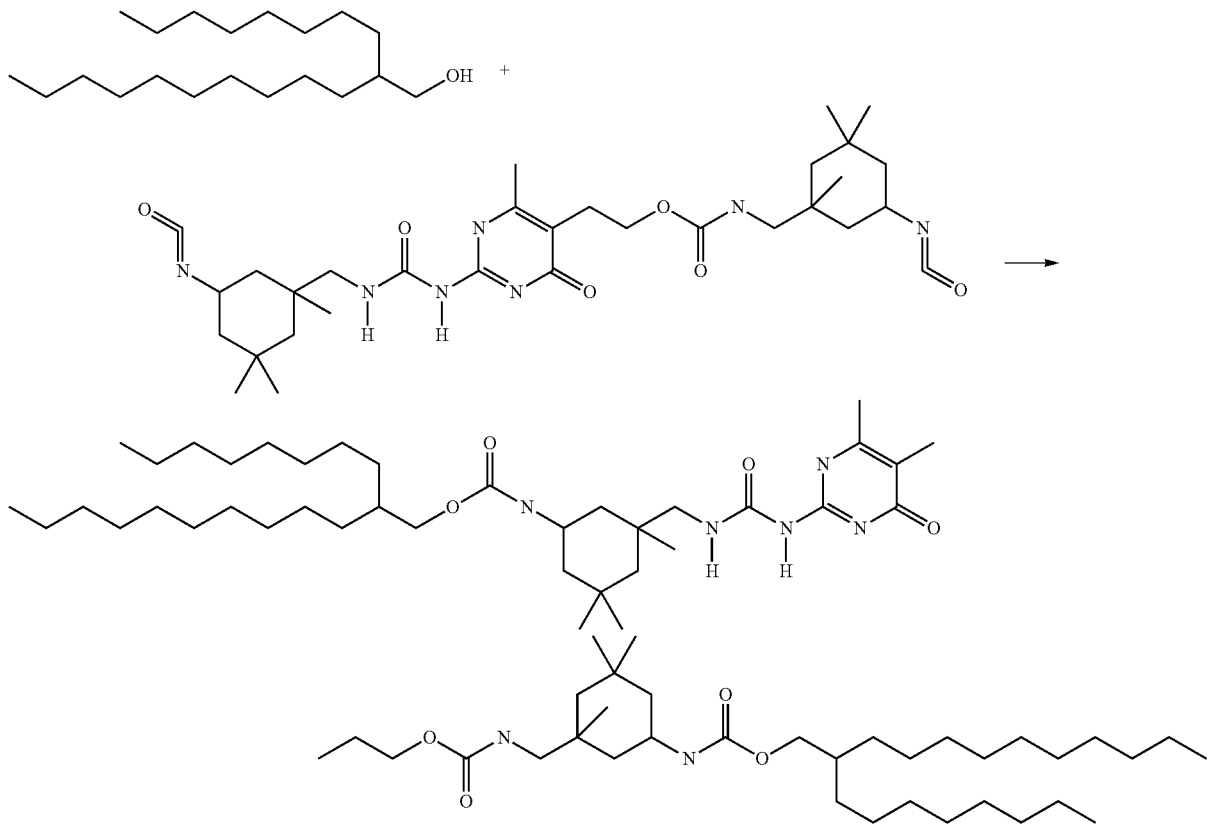

70 g of ureidopyrimidone diisocyanate are dissolved in methyltetrahydrofuran, under argon. 80.3 g of octyldodecanol in 100 ml of dichloromethane are added, under argon, followed by addition of 15 microliters of dibutyltin dilaurate (catalyst). The reaction mixture is refluxed until the isocyanate peak (2250-2265 cm$^{-1}$) has disappeared on IR spectrometry.

The excess octyldodecanol is removed by successive washing of the reaction medium with methanol, followed by three extractions and drying over MgSO$_4$. After evaporation of the organic phase, 103 g of a pale yellow powder, characterized by $^1$H NMR (structure in conformity), are obtained.

This powder may be conveyed in isododecane, for example at a concentration of 10% by weight; this concentration may especially be up to 60% by weight in isododecane, which then leads to a solution that is viscous but still manipulable. It is thus found that by functionalizing with a ureidopyrimidone, the oil changes from a liquid to a solid, which can be conveyed in isododecane at concentrations above 30%.

When a solution comprising 50% by weight of compound in isododecane is applied, after evaporating off the solvent, a glossy transparent film is obtained, which shows good adhesion by fragmentation, and low resistance to friction.

COMPOUND 2

Diisostearyl Malate Functionalized with a Ureidopyrimidone 15 g (0.0234 mol) of diisostearyl malate are dried under reduced pressure at 80° C. for 4 hours. 7.21 g (0.0117 mol) of ureidopyrimidone diisocyanate dissolved in 60 ml of methyltetrahydrofuran, and 12 µl of dibutyltin dilaurate catalyst are added. The mixture is heated at 95° C., under argon, for 26 hours (disappearance of the characteristic band for isocyanates on IR spectroscopy). 20 ml of methyltetrahydrofuran are added to the reaction mixture, and the resulting mixture is then filtered through Celite. After evaporating off the solvent and drying under reduced pressure, a pale yellow solid is obtained.

COMPOUND 3

Castor Oil Functionalized with a Ureidopyrimidone 15 g of castor oil (0.016 mol) are dried under reduced pressure at 80° C. for 4 hours. A solution of 4.9 g of ureidopyrimidone diisocyanate (0.008 mol) in 60 ml of methyltetrahydrofuran, and 12 µl of dibutyltin dilaurate catalyst are added. The mixture is heated at 90° C. for 19 hours (total disappearance of the characteristic band for isocyanates on IR spectroscopy). At the end of the reaction, the solvent is evaporated off and the resulting product is dried under reduced pressure at 35° C. overnight.

A pale yellow solid gum is obtained.

COMPOUND 4 (COMPARATIVE TO EXAMPLE 1)

Octyldodecanol Functionalized with Isophorone

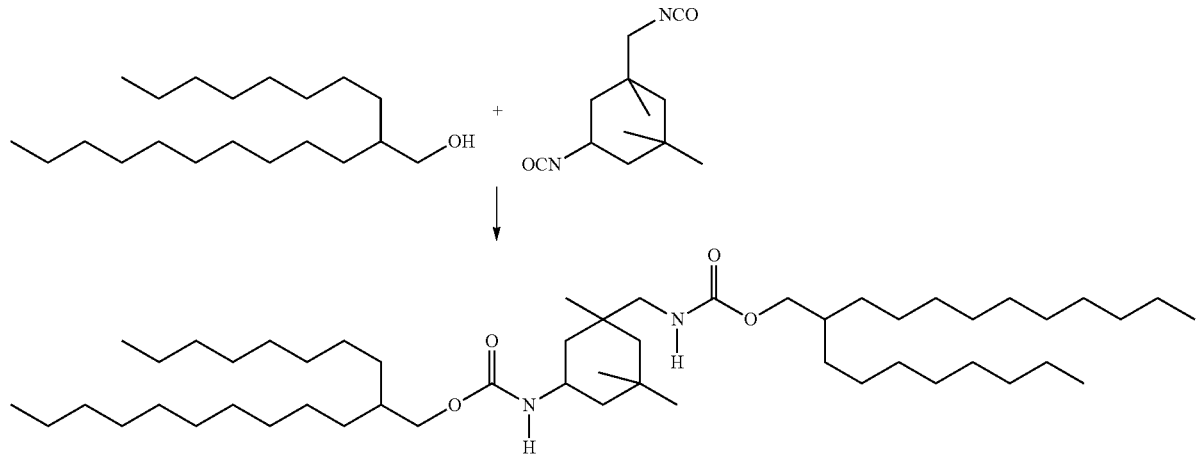

10 g of octyldodecanol are dried under reduced pressure at 80° C. for 2 hours, followed by addition of 3.72 g of isophorone diisocyanate and 25 microliters of dibutyltin dilaurate catalyst. The mixture is heated at 95° C. under argon. The disappearance of the isocyanate is monitored by IR spectroscopy (disappearance of the band between 2250 and 2265 $cm^{-1}$, after heating for 12 hours).

A viscous oil that does not form a cohesive material is obtained.

COMPOUND 5 (COMPARATIVE TO EXAMPLE 2)

Diisostearyl Malate Functionalized with Isophorone 10 g (0.0159 mol) of diisostearyl malate are dried under reduced pressure at 80° C. for 3 hours. 1.77 g (0.079 mol) of isophorone diisocyanate and 2.5 µl of catalyst (dibutyltin dilaurate) are added under argon, and the reaction mixture is heated at 95° C. for 16 hours. During the reaction, the viscosity of the reaction medium increases. The reaction is stopped after disappearance of the characteristic peak for isocyanates on IR spectroscopy.

COMPOUND 6 (COMPARATIVE TO EXAMPLE 3)

Castor Oil Functionalized with Isophorone 15 g (0.016 mol) of castor oil are dried under reduced pressure at 80° C. for 6 hours. 1.78 g (0.008 mol) of isophorone diisocyanate and 12 µl of dibutyltin dilaurate catalyst are added, and the mixture is heated at 90° C. for 16 hours. The reaction is stopped after disappearance of the characteristic peak for isocyanates on IR spectroscopy.

EXAMPLE 7

The compounds prepared in Examples 1 to 6 are observed, visually and by feel, and the results are summarized in the following table:

| | Physical appearance of the compound | Appearance of the film* Refractive index** (refractive index unfunctionalized oil) |
|---|---|---|
| Compound 1 | Yellow solid | Glossy tacky film, which does not dewet; uniform deposit. No transfer onto the fingers. 1.488 (1.46) |
| Compound 4 (comparative) | Transparent viscous oil | Film which dewets; non-uniform deposit. Transfers onto the fingers. 1.474 (1.46) |
| Compound 2 | Yellow solid | Glossy, sparingly tacky film, which does not dewet; uniform deposit. No transfer onto the fingers. 1.478 (1.462) |
| Compound 5 (comparative) | Transparent viscous oil | Glossy tacky film which dewets; non-uniform deposit. No transfer onto the fingers. 1.4598 (1.462) |
| Compound 3 | Yellow solid (solid gum) | Glossy, slightly tacky film; behaviour of a fragile solid, which does not dewet; uniform deposit. No transfer onto the fingers. 1.4852 (1.48) |
| Compound 6 (comparative) | Transparent viscous oil | Very tacky glossy film, which dewets; non-uniform deposit. Transfers onto the fingers. 1.4813 (1.48) |

*The films are formed from a solution containing 40% by weight of the compound, either in isododecane for Examples 1-2 and 4-5, or in tetrahydrofuran for compounds 3 and 6.
**For the refractive index measurements, all the films are formed from a solution containing 40% by weight of the compound in tetrahydrofuran; the refractive index is measured after evaporating off the solvent.
The term "film which does not dewet" means that, after deposition and evaporation of the solvent, a continuous, uniform "true" film is obtained.
The term "film which dewets" means that, after deposition and evaporation of the solvent, a non-uniform, discontinuous film "with holes" is obtained.

A tribometry test is performed on these deposits/films: the films are formed from a solution at 40% by weight in tetrahydrofuran, by deposition onto a nitrile elastomer, followed by drying for 24 hours at 25° C.

The tests are performed using a CSEM tribometer and equipped with a ball 6 mm in diameter. This ball, subjected to a 0.15 N load, rubs repeatedly on a film (10 to 20 µm thick).

The rotation speed of the disk is set at 6.3 cm/s, which corresponds to a frequency of one revolution per second. The test is ended when wear is complete, or else is stopped after 1000 stress revolutions.

| | Observations |
|---|---|
| Compound 1 | The film remains unchanged (uniform) for 300 revolutions (no wear or brittleness); the material is thus cohesive; behaviour of a solid. |
| Compound 4 (comparative) | No measurement possible: the material has no cohesion, and behaves like an oil. |
| Compound 2 | The film remains unchanged (uniform) for 1000 revolutions (no wear or brittleness); the material is thus cohesive and does not wear out |
| Compound 5 (comparative) | The material behaves like an oil, with a buttering effect when it is subjected to the wear test. |
| Example 3 | The film is sparingly brittle but remains unchanged for 10 revolutions; after 10 revolutions, the wear is more pronounced; this reflects the behaviour of a solid. |
| Compound 6 (comparative) | No measurement possible since no film was initially formed: behaviour of an oil. |

It is thus found that there is no decrease in the refractive index after functionalization. The oil keeps its glossy nature, even when functionalized. It is also found that functionalization with ureidopyrimidones leads to films that are more or less tacky, but that do not transfer onto the fingers, unlike the comparative films.

Furthermore, and principally, in the case of the oils functionalized with isophorone (comparative), the films dewet and do not form a uniform deposit. In contrast, the films obtained with the compounds according to the invention do not dewet and are uniform and cohesive. The tribometry results confirm the cohesion properties obtained with the compounds of the invention.

Functionalization with ureidopyrimidones thus leads to materials that are cohesive enough to be able to ensure remanence of the deposit, which, incidentally, is glossy, superior to the remanence of the prior art (isophorone).

In summary: the gloss is maintained, the cohesion of the deposit is improved, and thus its remanence is improved.

COMPOUND 8

Diisostearyl Malate Functionalized with a Ureidopyrimidone

Preparation Protocol

Preparation of the supramolecular oil: Diisostearyl malate functionalized with a ureidopyrimidone 150 g of diisostearyl malate were added over 1 hour 20 minutes at 50° C. to a solution of 57.4 g of isophorone diisocyanate and 38.18 g of methyl isocytosine, in the presence of the catalyst dibutyltin dilaurate, with control of the exothermicity and under an inert atmosphere. Stirring was continued for 55 minutes at 50° C. after the addition, and 50 ml of propylene carbonate were then added. The temperature of the reaction medium was then raised to 140° C. with a contact time of 2 hours, with stirring. The temperature of the reaction medium was then lowered to 70° C., the medium was neutralized by adding 30 ml of ethanol, and stirring was continued for 1 hour.

After adding 780 ml of ethyl acetate, the medium was filtered through Celite. After evaporating off the ethyl acetate, 400 ml of cyclohexane were added to the reaction medium, and the mixture was washed twice with an $H_2O$/EtOH mixture (2v/1v) saturated with NaCl. The organic phase was then stripped with isododecane, down to a viscous liquid, corresponding to the desired molecule in a solids content of 50%. For the purposes of the formulation, this dry extract may optionally be modified by adding isododecane to the medium.

COMPOUND 9

2-Hexyldecanol Functionalized with Ureidopyrimidone

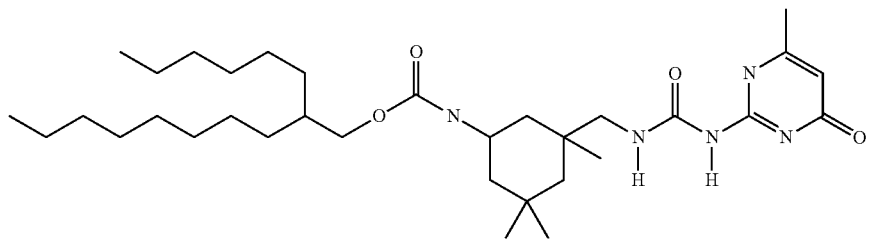 [SMILES: CCCCCCCCC(CCCCCC)COC(=O)NC1CC(C)(C)CC(C)(CNC(=O)Nc2nc(=O)cc(C)[nH]2)C1]

126.4 g of 2-hexyldecanol are heated at 60° C. under reduced pressure for 2 hours to dry them. After 2 hours, the oil is allowed to cool to 20° C. under argon, and is then added slowly, over 5 hours, to a mixture of 116 g of isophorone diisocyanate and 55 mg of DBTL catalyst at 50° C. At the end of the addition, the temperature of the reaction mixture is brought to 110° C., and 90 ml of propylene carbonate and 78.4 g of 6-methylisocytosine are then added, which produces a homogeneous white suspension. Stirring is continued at 110° C. for 2 hours, and the disappearance of the isocyanate is monitored by infrared spectroscopy. The disappearance of the peak at 2250 $cm^{-1}$ is observed. In parallel, disappearance of the amine originating from the isocytosine is monitored by means of an amine assay. At the end of the reaction, 500 g of isododecane are added, at 100° C., and a slightly cloudy pale yellow solution is obtained. 300 ml of ethanol are added and stirring is continued for 2 hours. After filtering through Celite, the reaction mixture is stripped with isododecane at 80° C. in order to remove the alcohol and the propylene carbonate.

Finally, the desired product conveyed in isododecane, in a solids content of 50%, is obtained. The product is especially characterized by HPLC and GPC (structure confirmed).

COMPOUND 10

2-Hexyldecanol Functionalized with Ureidopyrimidone

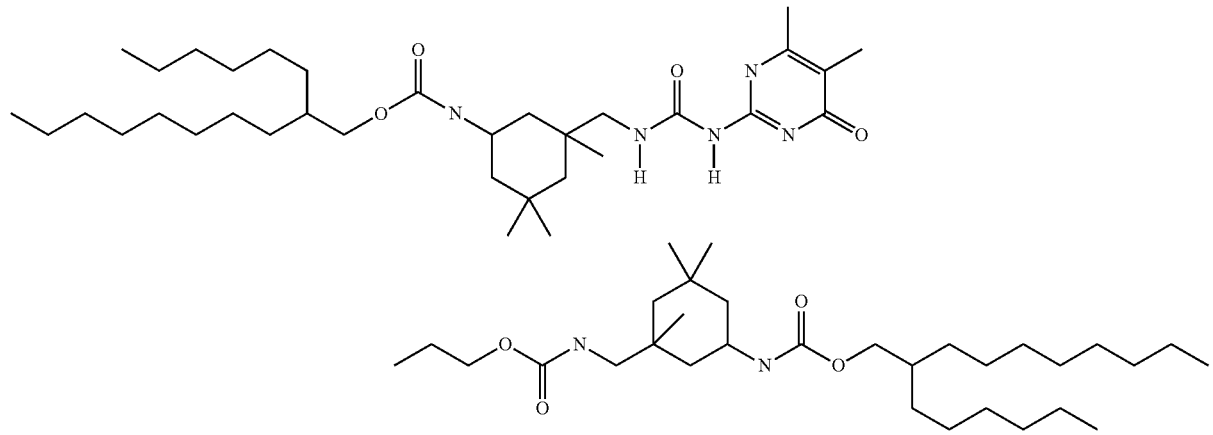

173.1 g of 2-hexyldecanol are heated at 60° C. under reduced pressure for 2 hours to dry them. After 2 hours, the oil is allowed to cool to 50° C. under argon, and is then added slowly, over 5 hours, to a mixture of 158.7 g of isophorone diisocyanate and 77 mg of DBTL catalyst at 50° C. At the end of the addition, the temperature of the reaction mixture is brought to 110° C., and 150 ml of propylene carbonate and 60.3 g of 5-hydroxyethyl-6-methylisocytosine are added, which produces a uniform white suspension. Stirring is continued at 110° C. for 5 hours, and the disappearance of the isocyanate is monitored by infrared spectroscopy. The disappearance of the peak at 2250 cm$^{-1}$ is observed. At the end of the reaction, the temperature of the reaction medium is reduced to 100° C., and 780 g of isododecane are added; a pale yellow cloudy mixture is obtained. 100 ml of ethanol are added and stirring is continued for 2 hours. After filtering through Celite, the reaction mixture is stripped with isododecane at 80° C. in order to remove the alcohol and the propylene carbonate.

Finally, the desired product conveyed in isododecane, in a solids content of 50%, is obtained. The product is especially characterized by HPLC and GPC (structure confirmed).

COMPOUND 11

2-Decyltetradecanol Functionalized with Ureidopyrimidone 126 g of 2-decyltetradecanol are heated at 100° C. under reduced pressure for 4 hours to dry them. After 2 hours, the oil is added, over 4 hours, at 50° C. and under argon, to a mixture of 94.7 g of isophorone diisocyanate and of DBTL catalyst (qs). Monitoring by assay of the isocyanate allows the reaction progress to be followed; at half-equivalence, 126 g of propylene carbonate and 53.3 g of 6-methylisocytosine are added. Stirring and heating are continued at 100° C. for 16 hours, and disappearance of the isocyanate is monitored by infrared spectroscopy. The disappearance of the peak at 2250 cm$^{-1}$ is observed. In parallel, disappearance of the amine originating from the isocytosine is monitored by means of an amine assay. At the end of the reaction, the temperature is cooled to 50° C., 100 ml of ethanol are added and stirring is continued for 5 hours. After filtering through Celite and stripping with isododecane, the desired product conveyed in isododecane, at a solids content of 50%, is obtained. The product is especially characterized by GPC and HPLC coupled to mass spectroscopy.

COMPOUND 12

Ureidopyrimidone-functionalized Jarcol 24 (J24)

200 g of Jarcol I-24 are added at 50° C. to IPDI (1.1 eq. IPDI) in the presence of the catalyst, with control of the exothermicity and under an inert atmosphere. Stirring is continued after the addition, for 30 minutes at 50° C. 1.3 equivalents of methylisocytosine (MIC) are then added to the mixture, followed by addition of 100 ml of propylene carbonate. The temperature of the reaction medium is then raised to 140° C., with a contact time of 1 hour at 140° C. The disappearance of the isocyanate functions is monitored by infrared spectroscopy, and the temperature of the medium is then lowered to 70° C., followed by addition of ml of ethanol and stirring for 1 hour. After addition of ethyl acetate, the medium is filtered through filter paper. After evaporating off the ethyl acetate, cyclohexane is added, followed by 5 washes with a mixture of water saturated with NaCl/ethanol (2v/1v). The organic phase is then dried over Na$_2$SO$_4$, filtered and stripped with isododecane. A solution with a 50% solids content of oil functionalized with a ureidopyrimidone is then obtained.

COMPOUND 13

Ureidopyrimidone-functionalized Jarcol 20 (J20)

180 g of Jarcol I-20 are added at 50° C. to IPDI (1.1 eq. IPDI) in the presence of the catalyst, with control of the exothermicity and under an inert atmosphere.

Stirring is continued for 30 minutes at 50° C. 1.3 equivalents of MIC are added to the reaction medium, followed by addition of 100 ml of propylene carbonate.

The temperature of the reaction medium is then raised to 140° C., with a contact time of 1 hour at 140° C. The reaction is monitored by infrared spectroscopy, with monitoring of the disappearance of the characteristic peak of the isocyanate function. The temperature is then lowered to 70° C., followed by addition of 30 ml of ethanol and stirring for 1 hour. After addition of ethyl acetate, the medium is filtered through filter paper. After evaporating off the ethyl acetate, cyclohexane is added, followed by 5 washes with a mixture of water saturated with NaCl/ethanol (2v/1v). The organic phase is then dried over $Na_2SO_4$, filtered and stripped with isododecane. A solution with a 50% solids content of oil functionalized with a ureidopyrimidone is then obtained.

Preferably, the composition according to the invention has a content of supramolecular compound of between 5% and 95% by weight, preferably between 10% and 95% by weight and better still preferably between 20% and 90% by weight relative to the total weight of the composition.

Additional Ingredient

The composition according to the invention comprises at least one additional ingredient preferably chosen from:
- silicone elastomers,
- silicone resins,
- polycondensates that may be obtained by reacting:
  - a tetraol containing from 4 to 10 carbon atoms;
  - a saturated, linear or branched monocarboxylic acid containing from 9 to 23 carbon atoms;
  - a cyclic dicarboxylic acid containing from 6 to 12 carbon atoms; and
  - an aromatic monocarboxylic acid containing from 7 to 11 carbon atoms,
- film-forming agents chosen from silicone resins and film-forming polymers, preferably chosen from the group comprising:
  - a film-forming block ethylenic copolymer,
  - a vinyl polymer comprising at least one carbosiloxane dendrimer-based unit,
  - a dispersion of acrylic or vinyl radical homopolymer or copolymer particles dispersed in the said liquid fatty phase,
- semicrystalline polymers,
- thickeners comprising at least one group and preferably at least two groups capable of establishing hydrogen interactions, chosen from:
  - polymeric thickeners, and
  - organogelling agents.

Silicone Elastomers:

According to one embodiment, the composition according to the invention comprises as additional ingredient at least one silicone elastomer (also known as an organopolysiloxane elastomer) combined with the said compound A described previously.

These particular elastomers, when they are in combination with the resins according to the invention, may make it possible to obtain tack-free and comfort properties (suppleness and softness of the deposit) for deposits of compositions comprising them.

The term "organopolysiloxane elastomer" means a supple, deformable organopolysiloxane having viscoelastic properties and especially the consistency of a sponge or a supple sphere. Its modulus of elasticity is such that this material withstands deformation and has limited capacity for extension and contraction. This material is capable of regaining its original shape after having been stretched.

The elastomeric crosslinked organopolysiloxane may be obtained via a crosslinking addition reaction of diorganopolysiloxane containing at least one hydrogen bonded to silicon and of diorganopolysiloxane containing ethylenically unsaturated groups bonded to silicon, especially in the presence of a platinum catalyst; or via a dehydrogenation crosslinking condensation reaction between a diorganopolysiloxane containing hydroxyl end groups and a diorgano-polysiloxane containing at least one hydrogen bonded to silicon, especially in the presence of an organotin; or via a crosslinking condensation reaction of a diorgano-polysiloxane containing hydroxyl end groups and of a hydrolysable organopolysilane; or via thermal cross-linking of organopolysiloxane, especially in the presence of an organoperoxide catalyst; or via cross-linking of organopolysiloxane by high-energy radiation such as gamma rays, ultraviolet rays or an electron beam.

Preferably, the elastomeric crosslinked organo-polysiloxane is obtained via a crosslinking addition reaction (A) of diorganopolysiloxane containing at least two hydrogens each linked to a silicon, and (B) of diorganopolysiloxane containing at least two ethylenically unsaturated groups bonded to silicon, especially in the presence (C) of a platinum catalyst, for instance as described in patent application EP-A-295 886.

In particular, the organopolysiloxane elastomer may be obtained via reaction of dimethylpolysiloxane containing dimethylvinylsiloxy end groups and of methylhydrogenopolysiloxane containing trimethylsiloxy end groups, in the presence of a platinum catalyst.

Compound (A) is the base reagent for the formation of elastomeric organopolysiloxane, and the crosslinking takes place via an addition reaction of compound (A) with compound (B) in the presence of the catalyst (C).

Compound (A) is in particular an organopoly-siloxane containing at least two hydrogen atoms linked to different silicon atoms in each molecule.

Compound (A) may have any molecular structure, in particular a linear-chain or branched-chain structure or a cyclic structure.

Compound (A) may have a viscosity at 25° C. ranging from 1 to 50 000 centistokes, in particular in order to show good miscibility with compound (B).

The organic groups linked to the silicon atoms in compound (A) may be alkyl groups such as methyl, ethyl, propyl, butyl or octyl; substituted alkyl groups such as 2-phenylethyl, 2-phenylpropyl or 3,3,3-trifluoropropyl; aryl groups such as phenyl, tolyl or xylyl; substituted aryl groups such as phenylethyl; and substituted monovalent hydrocarbon-based groups such as an epoxy group, a carboxylate ester group or a mercapto group.

Compound (A) may thus be chosen from methyl-hydrogenopolysiloxanes containing trimethylsiloxy end groups, dimethylsiloxane-methylhydrogenosiloxane copolymers containing trimethylsiloxy end groups and dimethylsiloxane-methylhydrogenosiloxane cyclic copolymers.

Compound (B) is advantageously a diorgano-polysiloxane containing at least two lower alkenyl groups (for example $C_2$-$C_4$); the lower alkenyl group may be chosen from vinyl, allyl and propenyl groups. These lower alkenyl groups may be located in any position of the organopolysiloxane molecule, but are preferably located at the end of the organopolysiloxane molecule. The organopolysiloxane (B) may have a branched-chain, linear-chain, cyclic or network structure, but the linear-chain structure is preferred. Compound (B) may have a viscosity ranging from the liquid state to the gum state. Preferably, compound (B) has a viscosity of at least 100 centistokes at 25° C.

Besides the abovementioned alkenyl groups, the other organic groups linked to the silicon atoms in compound (B) may be alkyl groups such as methyl, ethyl, propyl, butyl or octyl; substituted alkyl groups such as 2-phenylethyl, 2-phenylpropyl or 3,3,3-trifluoro-propyl; aryl groups such as phenyl, tolyl or xylyl; substituted aryl groups such as phenylethyl; and substituted monovalent hydrocarbon-based groups such as an epoxy group, a carboxylate ester group or a mercapto group.

The organopolysiloxanes (B) may be chosen from methylvinylpolysiloxanes, methylvinylsiloxane-dimethyl-siloxane copolymers, dimethylpolysiloxanes containing dimethylvinylsiloxy end groups, dimethylsiloxane-methylphenylsiloxane copolymers containing dimethylvinylsiloxy end groups, dimethylsiloxane-diphenylsiloxane-methylvinylsiloxane copolymers containing dimethylvinylsiloxy end groups, dimethyl-siloxane-methylvinylsiloxane copolymers containing trimethylsiloxy end groups, dimethylsiloxane-methyl-phenylsiloxane-methylvinylsiloxane copolymers containing trimethylsiloxy end groups, methyl(3,3,3-trifluoropropyl)polysiloxane containing dimethylvinyl-siloxy end groups, and dimethylsiloxane-methyl(3,3,3-trifluoropropyl)siloxane copolymers containing dimethylvinylsiloxy end groups.

In particular, the elastomeric organopolysiloxane may be obtained via reaction of dimethylpolysiloxane containing dimethylvinylsiloxy end groups and of methylhydrogenopolysiloxane containing trimethylsiloxy end groups, in the presence of a platinum catalyst.

Advantageously, the sum of the number of ethylenic groups per molecule of compound (B) and of the number of hydrogen atoms bonded to silicon atoms per molecule of compound (A) is at least 5.

It is advantageous for compound (A) to be added in an amount such that the molecular ratio between the total amount of hydrogen atoms bonded to silicon atoms in compound (A) and the total amount of all the ethylenically unsaturated groups in compound (B) is within the range from 1.5/1 to 20/1.

Compound (C) is the catalyst for the crosslinking reaction, and is especially chloroplatinic acid, chloroplatinic acid-olefin complexes, chloroplatinic acid-alkenylsiloxane complexes, chloroplatinic acid-diketone complexes, platinum black or platinum on a support.

The catalyst (C) is preferably added in a proportion of from 0.1 to 1000 parts by weight and better still from 1 to 100 parts by weight, as clean platinum metal per 1000 parts by weight of the total amount of compounds (A) and (B).

The elastomer is advantageously a non-emulsifying elastomer.

The term "non-emulsifying" defines organopoly-siloxane elastomers that do not contain any hydrophilic chains, and in particular that do not contain any polyoxyalkylene units (especially polyoxyethylene or polyoxypropylene) or any polyglyceryl units.

The elastomeric crosslinked organopolysiloxane particles are conveyed in the form of a gel constituted by an elastomeric organopolysiloxane included in at least one hydrocarbon-based oil and/or one silicone oil. In these gels, the organopolysiloxane particles are often non-spherical particles.

Non-emulsifying elastomers are especially described in patents EP 242 219, EP 285 886 and EP 765 656 and in patent application JP-A-61-194 009, the content of which is incorporated herein by reference.

Spherical non-emulsifying elastomers that may be used include those sold under the names DC 9040, DC 9041, DC 9509, DC 9505 and DC 9506 by the company Dow Corning.

The spherical non-emulsifying silicone elastomer may also be in the form of an elastomeric crosslinked organopolysiloxane powder coated with silicone resin, especially with silsesquioxane resin, as described, for example, in U.S. Pat. No. 5,538,793, the content of which is incorporated herein by reference. Such elastomers are sold under the names KSP-100, KSP-101, KSP-102, KSP-103, KSP-104 and KSP-105 by the company Shin-Etsu.

Other elastomeric crosslinked organopolysiloxanes in the form of spherical powders may be powders of hybrid silicone functionalized with perfluoroalkyl groups, sold especially under the name KSP-200 by the company Shin-Etsu; powders of hybrid silicone functionalized with phenyl groups, sold especially under the name KSP-300 by the company Shin-Etsu.

It is also possible to use in the compositions according to the invention silicone elastomers with an MQ group, such as those sold by the company Wacker under the names Belsil RG100, Belsil RPG33 and preferentially RG80. These particular elastomers, when in combination with the resins according to the invention, may make it possible to improve the transfer-resistance properties of the compositions comprising them.

The elastomer may also be an emulsifying elastomer.

The term "emulsifying organopolysiloxane elastomer" means an organopolysiloxane elastomer comprising at least one hydrophilic chain, such as polyoxyalkylenated organopolysiloxane elastomers and polyglycerolated silicone elastomers.

The emulsifying organopolysiloxane elastomer may be chosen from polyoxyalkylenated organopolysiloxane elastomers.

The polyoxyalkylenated organopolysiloxane elastomer is a crosslinked organopolysiloxane elastomer that may be obtained via a crosslinking addition reaction of diorganopolysiloxane containing at least one hydrogen bonded to silicon and of a polyoxyalkylene containing at least two ethylenically unsaturated groups.

Preferably, the polyoxyalkylenated crosslinked organopolysiloxane is obtained by a crosslinking addition reaction (A1) of diorganopolysiloxane containing at least two hydrogens each bonded to a silicon, and (B1) of polyoxyalkylene containing at least two ethylenically unsaturated groups, especially in the presence (C1) of a platinum catalyst, as described, for example, in U.S. Pat. Nos. 5,236,986 and 5,412,004.

In particular, the organopolysiloxane may be obtained by reaction of polyoxyalkylene (especially polyoxyethylene and/or polyoxypropylene) containing dimethylvinylsiloxy end groups and of methylhydrogeno-polysiloxane containing trimethylsiloxy end groups, in the presence of a platinum catalyst.

The organic groups bonded to silicon atoms of the compound (A1) may be alkyl groups containing from 1 to 18 carbon atoms, such as methyl, ethyl, propyl, butyl, octyl, decyl, dodecyl (or lauryl), myristyl, cetyl or stearyl; substituted alkyl groups such as 2-phenyl-ethyl, 2-phenylpropyl or 3,3,3-trifluoropropyl; aryl groups such as phenyl, tolyl or xylyl; substituted aryl groups such as phenylethyl; and substituted monovalent hydrocarbon-based groups such as an epoxy group, a carboxylate ester group or a mercapto group.

Compound (A1) may thus be chosen from methylhydrogenopolysiloxanes containing trimethylsiloxy end groups, dimethylsiloxane-methylhydrogenosiloxane copolymers containing trimethylsiloxy end groups, dimethylsiloxane-methylhydrogenosiloxane cyclic copolymers, or dimethylsiloxane-methylhydrogenosiloxane-laurylmethylsiloxane copolymers containing trimethylsiloxy end groups.

Compound (C1) is the crosslinking reaction catalyst, and is especially chloroplatinic acid, chloroplatinic acid-olefin complexes, chloroplatinic acid-alkenylsiloxane complexes, chloroplatinic acid-diketone complexes, platinum black and platinum on a support.

Advantageously, the polyoxyalkylenated silicone elastomers may be formed from divinyl compounds, in particular polyoxyalkylenes containing at least two vinyl groups, reacting with Si—H bonds of a polysiloxane.

Polyoxyalkylenated elastomers are especially described in U.S. Pat. Nos. 5,236,986, 5,412,004, 5,837,793 and 5,811,487, the content of which is incorporated by reference.

Polyoxyalkylenated silicone elastomers that may be used include those sold under the names KSG-21, KSG-20, KSG-30, KSG-31, KSG-32, KSG-33, KSG-210, KSG-310, KSG-320, KSG-330 and KSG-340 by the company Shin-Etsu, or DC9010 and DC9011 by the company Dow Corning.

The emulsifying silicone elastomer may also be chosen from polyglycerolated silicone elastomers.

The polyglycerolated silicone elastomer according to the invention is a crosslinked elastomeric organopolysiloxane that may be obtained by a crosslinking addition reaction of diorganopolysiloxane containing at least one hydrogen bonded to silicon and of polyglycerolated compounds containing ethylenically unsaturated groups, especially in the presence of a platinum catalyst.

Preferably, the crosslinked elastomeric organo-polysiloxane is obtained by a crosslinking addition reaction (A2) of diorganopolysiloxane containing at least two hydrogens each bonded to a silicon, and (B2) of glycerolated compounds containing at least two ethylenically unsaturated groups, especially in the presence (C2) of a platinum catalyst.

In particular, the organopolysiloxane may be obtained by reaction of a polyglycerolated compound containing dimethylvinylsiloxy end groups and of methylhydrogenopolysiloxane containing trimethylsiloxy end groups, in the presence of a platinum catalyst.

Compound (A2) is the base reagent for the formation of elastomeric organopolysiloxane and the crosslinking is performed by an addition reaction of compound (A2) with compound (B2) in the presence of the catalyst (C2).

Compound (A2) is in particular an organopolysiloxane containing at least 2 hydrogen atoms bonded to different silicon atoms in each molecule.

Compound (A2) may have any molecular structure, in particular a linear chain or branched chain structure or a cyclic structure.

Compound (A2) may have a viscosity at 25° C. ranging from 1 to 50 000 centistokes, especially in order to have good miscibility with compound (B2).

The organic groups bonded to silicon atoms of the compound (A2) may be alkyl groups containing from 1 to 18 carbon atoms, such as methyl, ethyl, propyl, butyl, octyl, decyl, dodecyl (or lauryl), myristyl, cetyl or stearyl; substituted alkyl groups such as 2-phenylethyl, 2-phenylpropyl or 3,3,3-trifluoropropyl; aryl groups such as phenyl, tolyl or xylyl; substituted aryl groups such as phenylethyl; and substituted monovalent hydrocarbon-based groups such as an epoxy group, a carboxylate ester group or a mercapto group. Said organic group is preferably chosen from methyl, phenyl and lauryl groups.

Compound (A2) may thus be chosen from methylhydrogenopolysiloxanes containing trimethylsiloxy end groups, dimethylsiloxane-methylhydrogenosiloxane copolymers containing trimethylsiloxy end groups, dimethylsiloxane-methylhydrogenosiloxane cyclic copolymers, or dimethylsiloxane-methylhydrogeno-siloxane-laurylmethylsiloxane copolymers containing trimethylsiloxy end groups.

Compound (B2) may be a polyglycerolated compound corresponding to formula (B') below:

  (B')

in which m is an integer ranging from 2 to 6, n is an integer ranging from 2 to 200, preferably ranging from 2 to 100, preferably ranging from 2 to 50, preferably ranging from 2 to 20, preferably ranging from 2 to 10 and preferentially ranging from 2 to 5, and in particular equal to 3; Gly denotes:

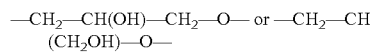

Advantageously, the sum of the number of ethylenic groups per molecule of compound (B2) and of the number of hydrogen atoms bonded to silicon atoms per molecule of compound (A2) is at least 4.

It is advantageous for compound (A2) to be added in an amount such that the molar ratio between the total amount of hydrogen atoms bonded to silicon atoms in compound (A2) and the total amount of all the ethylenically unsaturated groups in compound (B2) is within the range from 1/1 to 20/1.

Compound (C2) is the crosslinking reaction catalyst, and is especially chloroplatinic acid, chloroplatinic acid-olefin complexes, chloroplatinic acid-alkenylsiloxane complexes, chloroplatinic acid-diketone complexes, platinum black and platinum on a support.

The catalyst (C2) is preferably added in from 0.1 to 1000 parts by weight, better still from 1 to 100 parts by weight, as clean platinum metal per 1000 parts by weight of the total amount of compounds (A2) and (B2).

The polyglycerolated silicone elastomer according to the invention is conveyed in the form of a gel in at least one hydrocarbon-based oil and/or one silicone oil. In these gels, the polyglycerolated elastomer is often in the form of non-spherical particles.

Polyglycerolated silicone elastomers that may be used include those sold under the names KSG-710, KSG-810, KSG-820, KSG-830 and KSG-840 by the company Shin-Etsu.

Non-emulsifying elastomers that may more particularly be used include those sold under the names KSG-6, KSG-15, KSG-16, KSG-18, KSG-41, KSG-42, KSG-43 and KSG-44 by the company Shin-Etsu, DC9040 and DC9041 by the company Dow Corning, and SFE 839 by the company General Electric.

Emulsifying elastomers that may more particularly be used include those sold under the names KSG-31, KSG-32, KSG-33, KSG-210 and KSG-710 by the company Shin-Etsu.

The composition according to the invention may comprise such an organopolysiloxane elastomer, alone or as a mixture, in a content ranging from 0.1% to 20% by weight, preferably from 0.2% to 15% by weight and even more preferably from 0.5% to 12% by weight.

The combination of a supramolecular compound as described previously with a silicone elastomer especially makes it possible, in particular in compositions for making up or caring for keratin materials, and particularly the skin or the lips, to obtain uniform mixing and a non-tacky, supple (flexible) deposit on the keratin materials.

It is understood that, in the context of the present invention, the weight percentages of a compound are always expressed as weight of active material of the compound under consideration.

Polyesters or Polycondensates

According to one embodiment, the composition according to the invention comprises as additional ingredient at least one polyester (also known as a polycondensate) combined with the said compound A described previously.

The combination of a supramolecular compound as described previously with a polycondensate as described hereinbelow especially makes it possible, in particular in compositions for making up or caring for keratin materials, and particularly the skin or the lips, to obtain uniform mixing and a glossy, transfer-resistant and sparingly tacky deposit on the keratin materials.

A polyester that is suitable for use in the invention may be advantageously obtained by reacting a polyol, a polycarboxylic acid, a non-aromatic monocarboxylic acid and an aromatic monocarboxylic acid.

In particular, a polyester that is suitable for use in the invention may be preferentially obtained by reacting:
- a tetraol containing from 4 to 10 carbon atoms;
- a linear or branched saturated monocarboxylic acid containing from 9 to 23 carbon atoms;
- a cyclic dicarboxylic acid containing from 6 to 12 carbon atoms;
- an aromatic monocarboxylic acid containing from 7 to 11 carbon atoms.

Advantageously, a polyester of the invention may be obtained by reacting:
- from 10% to 30% by weight of tetraol containing from 4 to 10 carbon atoms;
- from 40% to 80% by weight of a linear or branched saturated monocarboxylic acid containing from 9 to 23 carbon atoms;
- from 5% to 30% by weight of a cyclic dicarboxylic acid containing from 6 to 12 carbon atoms;
- from 0.1% to 10% by weight of an aromatic monocarboxylic acid containing from 7 to 11 carbon atoms, the contents being expressed as weight percentages relative to the total weight of the polyester.

A polyester used according to the invention comprises a tetraol. The term "tetraol" means a polyol comprising 4 hydroxyl groups.

A tetraol used for the preparation of the polyester is advantageously a linear, branched and/or cyclic, saturated or unsaturated hydrocarbon-based compound containing from 4 to 10 carbon atoms, and possibly also comprising one or more oxygen atoms intercalated in the chain (ether function). Obviously, a mixture of such tetraols may be used.

A tetraol may in particular be a saturated, linear or branched hydrocarbon-based compound containing 4 to 10 carbon atoms.

A tetraol may be chosen from pentaerythritol or tetramethylolmethane, erythritol, diglycerol and ditrimethylolpropane.

Preferably, the tetraol is chosen from pentaerythritol and diglycerol.

Even more preferentially, a tetraol may be pentaerythritol.

The content of tetraol, or tetraol mixture, represents from 10% to 30% by weight, especially from 12% to 25% by weight and better still from 14% to 22% by weight relative to the total weight of the polyester.

A polyester used according to the invention also comprises a linear or branched, saturated monocarboxylic acid containing from 9 to 23 carbon atoms and especially 12 to 22 carbon atoms.

The term "saturated monocarboxylic acid" means a compound of formula RCOOH in which R is a saturated linear or branched hydrocarbon-based radical containing from 8 to 22 carbon atoms and especially from 11 to 21 carbon atoms. Obviously, a mixture of such monocarboxylic acids may be used.

Among the saturated monocarboxylic acids that may be used, mention may be made, alone or as a mixture, of: nonanoic acid, isononanoic acid (or pelargonic acid), decanoic acid (or capric acid), lauric acid, tridecanoic acid (or tridecylic acid), myristic acid, palmitic acid, stearic acid, isostearic acid, arachidic acid and behenic acid.

Preferably, lauric acid, myristic acid, isononanoic acid, nonanoic acid, palmitic acid, isostearic acid, stearic acid or behenic acid, and mixtures thereof, may be used.

Preferentially, isostearic acid or stearic acid is used.

When the saturated monocarboxylic acid is liquid at room temperature, it generally leads to a polyester that is liquid at room temperature.

Liquid monocarboxylic acids that may be mentioned include nonanoic acid, isononanoic acid and isostearic acid.

When the saturated monocarboxylic acid is solid at room temperature, it generally leads to a polyester that is solid at room temperature.

Solid monocarboxylic acids that may be mentioned include decanoic acid, lauric acid, tridecanoic acid, myristic acid, palmitic acid, stearic acid, arachidic acid and behenic acid.

The content of saturated monocarboxylic acid, or the mixture of the said acids, represents from 40% to 80% by weight, especially from 42% to 75% by weight, or even 45% to 70% by weight and better still 50% to 65% by weight relative to the total weight of the polyester.

The polyester used according to the invention also comprises a cyclic dicarboxylic acid containing from 6 to 12 carbon atoms and especially containing 8 carbon atoms. The cyclic dicarboxylic acid may be aromatic or non-aromatic. The cyclic dicarboxylic acid is preferably aromatic.

Obviously, a mixture of such cyclic dicarboxylic acids may be used.

A cyclic dicarboxylic acid may be chosen from cyclopropanedicarboxylic acid, cyclohexanedicarboxylic acid, cyclobutanedicarboxylic acid, phthalic acid, terephthalic acid, isophthalic acid, tetrahydrophthalic acid, naphthalene-2,3-dicarboxylic acid and naphthalene-2,6-dicarboxylic acid, or mixtures thereof.

Preferably, the cyclic dicarboxylic acid is chosen from phthalic acid, terephthalic acid and isophthalic acid. Phthalic acid may be advantageously used in its anhydride form.

Preferentially, the cyclic dicarboxylic acid is isophthalic acid.

A cyclic dicarboxylic acid, or a mixture of such diacids, may represent from 5% to 30% by weight and preferably from 15% to 25% by weight relative to the total weight of the polyester.

A polyester used according to the invention also comprises an aromatic monocarboxylic acid containing from 7 to 11 carbon atoms.

The term "aromatic monocarboxylic acid" means a compound of formula R'COOH, in which R' is an aromatic hydrocarbon-based radical containing 6 to 10 carbon atoms; R' is in particular a phenyl radical, optionally substituted with 1 to 3 alkyl radicals containing from 1 to 4 carbon atoms.

Obviously, a mixture of such aromatic monocarboxylic acids may be used.

The aromatic monocarboxylic acid may be chosen from benzoic acid and 4-tert-butylbenzoic acid.

The aromatic monocarboxylic acid is preferably benzoic acid.

The said aromatic monocarboxylic acid, or the mixture of the said acids, represents from 0.1% to 10% by weight, especially from 0.5% to 9.95% by weight and better still from 1% to 9.5% by weight, or even from 1.5% to 8% by weight relative to the total weight of the polyester.

According to one preferred embodiment, the said polyester is obtained by reacting:
- from 12% to 25% by weight of a tetraol containing from 4 to 10 carbon atoms;

from 40% to 75% by weight of a linear or branched saturated monocarboxylic acid containing from 9 to 23 carbon atoms;

from 15% to 25% by weight of a cyclic dicarboxylic acid containing from 6 to 12 carbon atoms;

from 0.5% to 9.95% by weight of an aromatic monocarboxylic acid containing from 7 to 11 carbon atoms, the contents being expressed as weight percentages relative to the total weight of the polyester.

According to another preferred embodiment, the said polyester is obtained by reacting:

from 14% to 22% by weight of a tetraol containing from 4 to 10 carbon atoms;

from 45% to 70% by weight of a linear or branched saturated monocarboxylic acid containing from 9 to 23 carbon atoms;

from 15% to 25% by weight of a cyclic dicarboxylic acid containing from 6 to 12 carbon atoms;

from 1% to 9.5% by weight of an aromatic monocarboxylic acid containing from 7 to 11 carbon atoms, the contents being expressed as weight percentages relative to the total weight of the polyester.

According to another preferred embodiment, the said polyester is obtained by reacting:

from 14% to 22% by weight of a tetraol containing from 4 to 10 carbon atoms;

from 50% to 65% by weight of a linear or branched, saturated monocarboxylic acid containing from 9 to 23 carbon atoms;

from 15% to 25% by weight of a cyclic dicarboxylic acid containing from 6 to 12 carbon atoms;

from 1.5% to 8% by weight of an aromatic monocarboxylic acid containing from 7 to 11 carbon atoms, the contents being expressed as weight percentages relative to the total weight of the polyester.

In one preferred embodiment of the polyester used according to the invention, the aromatic monocarboxylic acid is present in a molar amount of less than or equal to that of the linear or branched saturated monocarboxylic acid; in particular, the ratio between the number of moles of aromatic monocarboxylic acid and the number of moles of linear or branched saturated monocarboxylic acid ranges from 0.08 to 0.70. The said weight ratio preferably ranges between 0.10 and 0.60 and more preferentially from 0.12 to 0.40.

According to one embodiment of the invention, a polyester described previously may be chosen from benzoic acid/isophthalic acid/isostearic acid/penta-erythritol polyesters and benzoic acid/isophthalic acid/stearic acid/pentaerythritol polyesters, and mixtures thereof.

These monomers are especially used in the monomer concentration ranges described previously.

Preferably, the polyester has:

an acid number, expressed as mg of potassium hydroxide per g of polyester, of greater than or equal to 1; especially between 2 and 30 and even better still between 2.5 and 15; and/or a hydroxyl number, expressed in mg of potassium hydroxide per g of polyester, of greater than or equal to 40; especially between 40 and 120 and better still between 40 and 80.

These acid and hydroxyl numbers may be readily determined by a person skilled in the art via the usual analytical methods.

Preferably, a polyester of the invention has a weight-average molecular mass (Mw) of between 3000 and 1 000 000, or even between 3000 and 300 000.

The average molecular weight may be determined by gel permeation chromatography or by light scattering, depending on the solubility of the polymer under consideration.

Preferably, a polyester of the invention has a viscosity, measured at 110° C., of between 20 and 4000 mPa·s, especially between 30 and 3500 mPa·s or even between 40 and 3000 mPa·s and better still between and 2500 mPa·s. This viscosity is measured in the manner described hereinbelow.

According to one preferred embodiment, the polyester may be in liquid form at room temperature. A liquid polyester may have a weight-average molecular mass (Mw) ranging from 40 000 to 1 000 000 and preferably ranging from 50 000 to 300 000.

A liquid polyester may have a viscosity, measured at 110° C., ranging from 1000 to 4000 mPa·s and preferably ranging from 1500 to 3000 mPa·s.

In particular, a liquid polyester may be a benzoic acid/isophthalic acid/isostearic acid/pentaerythritol polyester, these monomers especially being present in the monomer concentration ranges described previously.

According to another embodiment, the polyester may also be in solid form at room temperature. A solid polyester may have a weight-average molecular mass (Mw) ranging from 3000 to 30 000 and preferably ranging from 8000 to 15 000.

The solid polyester may have a viscosity, measured at 80° C., ranging from 20 to 1000 mPa·s and preferably ranging from 50 to 600 mPa·s.

In particular, a solid polyester is a benzoic acid/isophthalic acid/stearic acid/pentaerythritol polyester, these monomers being present especially in the monomer concentration ranges described previously.

A polyester of the invention may be prepared according to the synthetic process described in patent application EP-A-1 870 082.

The viscosity of a polyester of the invention may be measured in the manner described hereinbelow.

The viscosity at 80° C. or at 110° C. of a polyester is measured using a cone-plate viscometer of Brookfield CAP 1000+ type.

The appropriate cone-plate is determined by a person skilled in the art on the basis of his knowledge; especially:

between 50 and 500 mPa·s, a 02 cone may be used,
between 500 and 1000 mPa·s: 03 cone,
between 1000 and 4000 mPa·s: 05 cone, and
between 4000 and 10 000 mPa·s: 06 cone.

The amount of polyester, also known as polycondensate, present in a composition of the invention may range from 1% to 60% by weight, preferably from 2% to 50% by weight, especially from 3% to 45% by weight, or even from 4% to 35% by weight and better still from 5% to 30% by weight relative to the total weight of the composition.

A polyester that is suitable for use in the invention may be readily conveyed in cosmetic oily or solvent media, especially oils, fatty alcohols and/or fatty esters.

A polyester of the invention may be readily prepared, in a single synthetic step, without producing waste, and at low cost.

A polyester that is suitable for use in the invention may be advantageously branched so as to generate a network by entanglement of polymer chains, and thus to obtain the desired properties, especially in terms of improved remanence and improved gloss, and in terms of solubility.

According to one embodiment, a composition of the invention may comprise at least two polymers that are different from each other.

Film-forming Agents:

The composition according to the invention may comprise, combined with the said compound A described previously, at least one film-forming agent (other than the said compound A) as additional ingredient, chosen from silicone resins and film-forming polymers.

In the present invention, the term "film-forming agent" means a compound that is capable of forming, by itself or in the presence of an auxiliary film-forming agent, a macroscopically continuous film that adheres to keratin materials, preferably a cohesive film, and better still a film whose cohesion and mechanical properties are such that the said film can be isolated and manipulated in isolation, for example when the said film is made by pouring onto a non-stick surface, for instance a Teflon-coated or silicone-coated surface.

The combination of a supramolecular compound as described previously with a film-forming agent (other than the supramolecular compound) makes it possible especially, in particular in compositions for making up or caring for keratin materials, and in particular the skin or the lips, to obtain uniform mixing and a glossy deposit on the keratin materials, which shows good remanence of the colour of the deposit and is non-tacky.

Silicone Resins

According to a first embodiment, the film-forming agent combined with the said compound A described previously is a silicone resin.

The combination of a supramolecular compound as described previously with a silicone resin makes it especially possible, in particular in compositions for making up or caring for keratin materials, and particularly the skin or the lips, to obtain uniform mixing and a glossy deposit on the keratin materials, which shows good remanence of the colour and is non-tacky.

More generally, the term "resin" means a compound of three-dimensional structure. "Silicone resins" are also referred to as "siloxane resins". Thus, for the purposes of the present invention, a polydimethylsiloxane is not a silicone resin.

The nomenclature of silicone resins (also known as siloxane resins) is known under the name "MDTQ", the resin being described as a function of the various siloxane monomer units it comprises, each of the letters M, D, T and Q characterizing a type of unit.

The letter M represents the monofunctional unit of formula $R1R2R3SiO_{1/2}$, the silicon atom being bonded to only one oxygen atom in the polymer comprising this unit.

The letter D means a difunctional unit $R1R2SiO_{2/2}$ in which the silicon atom is bonded to two oxygen atoms.

The letter T represents a trifunctional unit of formula $R1SiO_{3/2}$.

Such resins are described, for example, in the *Encyclopaedia of Polymer Science and Engineering*, vol. 15, John Wiley & Sons, New York (1989), pp. 265-270 and U.S. Pat. Nos. 2,676,182, 3,627,851, 3,772,247, 5,248,739 or U.S. Pat. Nos. 5,082,706, 5,319,040, 5,302,685 and 4,935,484.

In the units M, D and T defined previously, R, i.e. R1 and R2, represents a hydrocarbon-based radical (especially alkyl) containing from 1 to 10 carbon atoms, a phenyl group, a phenylalkyl group or a hydroxyl group.

Finally, the letter Q means a tetrafunctional unit $SiO_{4/2}$ in which the silicon atom is bonded to four hydrogen atoms, which are themselves bonded to the rest of the polymer.

Various silicone resins with different properties may be obtained from these various units, the properties of these polymers varying as a function of the type of monomer (or unit), of the nature and number of the radical R, of the length of the polymer chain, of the degree of branching and of the size of the side chains.

As silicone resins that may be used in the compositions according to the invention, silicone resins of MQ type, of T type or of MQT type may be used, for example.

MQ Resins:

As examples of silicone resins of MQ type, mention may be made of the alkyl siloxysilicates of formula $[(R1)_3SiO_{1/2}]_x$ $(SiO_{4/2})_y$ (MQ units) in which x and y are integers ranging from 50 to 80, and such that the group R1 represents a radical as defined previously, and is preferably an alkyl group containing from 1 to 8 carbon atoms or a hydroxyl group, preferably a methyl group.

As examples of solid silicone resins of MQ type of the trimethyl siloxysilicate type, mention may be made of those sold under the reference SR1000 by the company General Electric, under the reference TMS 803 by the company Wacker, under the name KF-7312J by the company Shin-Etsu, or DC 749 and DC 593 by the company Dow Corning.

As silicone resins comprising siloxysilicate MQ units, mention may also be made of phenylalkyl siloxysilicate resins, such as phenylpropyl dimethylsiloxysilicate (Silshine 151 sold by the company General Electric). The preparation of such resins is especially described in U.S. Pat. No. 5,817,302.

T Resins:

As examples of silicone resins of T type, mention may be made of polysilsesquioxanes of formula $(RSiO_{3/2})_x$ (T units) in which x is greater than 100 and such that the group R is an alkyl group containing from 1 to 10 carbon atoms, said polysilsesquioxanes also possibly comprising Si—OH end groups.

Use may preferably be made of polymethylsil-sesquioxane resins in which R represents a methyl group, for instance those sold:

by the company Wacker under the reference Resin MK such as Belsil PMS MK: polymer comprising $CH_3SiO_{3/2}$ repeating units (T units), which may also comprise up to 1% by weight of $(CH_3)_2SiO_{2/2}$ units (D units) and with an average molecular weight of about 10 000 g/mol, or by the company Shin-Etsu under the reference KR-220L, which are compounds of T units of formula $CH_3SiO_{3/2}$ and contain Si—OH (silanol) end groups, under the reference KR-242A, which comprise 98% of T units and 2% of dimethyl D units and contain Si—OH end groups, or under the reference KR-251 comprising 88% of T units and 12% of dimethyl D units and containing Si—OH end groups.

MQT Resins:

Resins comprising MQT units that are especially known are those mentioned in document U.S. Pat. No. 5,110,890.

A preferred form of resins of MQT type are MQT-propyl resins (also known as MQTPr). Such resins that may be used in the compositions according to the invention are especially those described and prepared in patent application WO 2005/075 542, the content of which is incorporated herein by reference.

The MQ-T-propyl resin preferably comprises the following units:

(i) $(R1_3SiO_{1/2})_a$ (ii) $(R2_2SiO_{2/2})_b$ (iii) $(R3SiO_{3/2})_c$ and
(iv) $(SiO_{4/2})_d$
with
R1, R2 and R3 independently representing a hydrocarbon-based radical (especially alkyl) containing from 1 to 10 carbon atoms, a phenyl group, a phenylalkyl group or a hydroxyl group, and preferably an alkyl radical containing from 1 to 8 carbon atoms or a phenyl group,
a being between 0.05 and 0.5,
b being between 0 and 0.3,
c being greater than 0,
d being between 0.05 and 0.6,
a+b+c+d=1, and a, b, c and d being mole fractions,
on condition that more than 40 mol % of the groups R3 of the siloxane resin are propyl groups.

Preferably, the siloxane resin comprises the following units:
(i) $(R1_3SiO_{1/2})_a$
(iii) $(R3SiO_{3/2})_c$ and
(iv) $(SiO_{4/2})_d$
with
R1 and R3 independently representing an alkyl group containing from 1 to 8 carbon atoms, R1 preferably being a methyl group and R3 preferably being a propyl group,
a being between 0.05 and 0.5, preferably between 0.15 and 0.4,
c being greater than 0, preferably between 0.15 and 0.4,
d being between 0.05 and 0.6, preferably between 0.2 and 0.6, or between 0.2 and 0.55,
a+b+c+d=1, and a, b, c and d being mole fractions,
on condition that more than 40 mol % of the groups R3 of the siloxane resin are propyl groups.

The siloxane resins that may be used according to the invention may be obtained via a process comprising the reaction of:
A) an MQ resin comprising at least 80 mol % of units $(R1_3SiO_{1/2})_a$ and $(SiO_{4/2})_d$,
R1 representing an alkyl group containing from 1 to 8 carbon atoms, an aryl group, a carbinol group or an amino group,
a and d being greater than 0,
the ratio a/d being between 0.5 and 1.5;
and
B) a T-propyl resin comprising at least 80 mol % of units $(R3SiO_{3/2})_c$,
R3 representing an alkyl group containing from 1 to 8 carbon atoms, an aryl group, a carbinol group or an amino group,
c being greater than 0,
on condition that at least 40 mol % of the groups R3 are propyl groups,
in which the mass ratio A/B is between 95/5 and 15/85, and the mass ratio A/B is preferably 30/70.

Advantageously, the mass ratio A/B is between 95/5 and 15/85. Preferably, the ratio A/B is less than or equal to 70/30. These preferred ratios have been found to afford comfortable deposits due to the absence of percolation of the rigid particles of MQ resin in the deposit.

Thus, preferably, the silicone resin is chosen from the group comprising:
a) a resin of MQ type, chosen especially from (i) alkyl siloxysilicates, which may be trimethyl siloxysilicates, of formula $[(R1)_3SiO_{1/2}]_x(SiO_{4/2})_y$, in which x and y are integers ranging from 50 to 80, and such that the group R1 represents a hydrocarbon-based radical containing from 1 to 10 carbon atoms, a phenyl group, a phenylalkyl group or a hydroxyl group, and preferably is an alkyl group containing from 1 to 8 carbon atoms, preferably a methyl group, and (ii) phenylalkyl siloxysilicate resins, such as phenylpropyldimethyl siloxysilicate, and/or
b) a resin of T type, chosen especially from the polysilsesquioxanes of formula $(RSiO_{3/2})_x$, in which x is greater than 100 and the group R is an alkyl group containing from 1 to 10 carbon atoms, for example a methyl group, the said polysilsesquioxanes also possibly comprising Si—OH end groups, and/or
c) a resin of MQT type, especially of MQT-propyl type, which may comprise units (i) $(R1_3SiO_{1/2})_a$, and (ii) $(R2_2SiO_{2/2})_b$, (iii) $(R3SiO_{3/2})_c$ and (iv) $(SiO_{4/2})_d$,
with $R^1$, $R^2$ and $R^3$ independently representing a hydrocarbon-based radical, especially alkyl, containing from 1 to 10 carbon atoms, a phenyl group, a phenylalkyl group or a hydroxyl group and preferably an alkyl radical containing from 1 to 8 carbon atoms or a phenyl group,
a being between 0.05 and 0.5,
b being between 0 and 0.3,
c being greater than 0,
d being between 0.05 and 0.6,
a+b+c+d=1, and a, b, c and d being mole fractions,
on condition that more than 40 mol % of the groups $R^3$ of the siloxane resin are propyl groups.

Preferably, the silicone resin is present in the composition according to the invention in a total resin solids content ranging from 1% to 40% by weight, preferably ranging from 2% to 30% by weight and better still ranging from 3% to 25% by weight relative to the total weight of the composition.

Film-forming Polymers

According to a second embodiment, the film-forming agent combined with the said compound A described previously is a film-forming polymer.

Preferably, the film-forming polymer is chosen from the group comprising:
a film-forming block ethylenic copolymer,
a vinyl polymer comprising at least one carbosiloxane dendrimer-based unit,
a dispersion of acrylic or vinyl radical homopolymer or copolymer particles dispersed in the said liquid fatty phase.

In the present invention, the term "film-forming polymer" means a polymer that is capable of forming, by itself or in the presence of an auxiliary film-forming agent, a macroscopically continuous film that adheres to keratin materials, and preferably a cohesive film, and better still a film whose cohesion and mechanical properties are such that the said film can be isolated and manipulated in isolation, for example when the said film is prepared by pouring onto a non-stick surface such as a Teflon-coated or silicone-coated surface.

The combination of a supramolecular compound as described previously with a film-forming polymer makes it possible especially, in particular in compositions for making up or caring for keratin materials, particularly the skin or the lips, to obtain uniform mixing and a glossy deposit on the keratin materials, which shows good colour remanence and is non-tacky.

1. Block Ethylenic Copolymer:

According to a first embodiment of the invention, the film-forming polymer is a block ethylenic copolymer, containing at least a first block with a glass transition temperature (Tg) of greater than or equal to 40° C. and being derived totally or partly from one or more first monomers, which are such that the homopolymer prepared from these monomers has a glass transition temperature of greater than or equal to 40° C., and at least a second block with a glass transition temperature of less than or equal to 20° C. and being derived totally or partly from one or more second monomers, which are such that the homopolymer prepared from these monomers has a glass transition temperature of less than or equal to 20° C., the said first block and the said second block being linked together via a random intermediate segment comprising at least one of the said first constituent monomers of the first block and at least one of the said second constituent monomers of the second block, and the said block copolymer having a polydispersity index I of greater than 2.

The block polymer used according to the invention thus comprises at least a first block and at least a second block.

The term "at least one block" means one or more blocks.

The term "block polymer" means a polymer comprising at least two different blocks and preferably at least three different blocks.

The term "ethylenic polymer" means a polymer obtained by polymerization of ethylenically unsaturated monomers.

The block ethylenic polymer used according to the invention is prepared exclusively from monofunctional monomers.

This means that the block ethylenic polymer used according to the present invention does not contain any multifunctional monomers, which can break the linearity of a polymer so as to obtain a branched or even crosslinked polymer, depending on the content of multifunctional monomer. The polymer used according to the invention does not contain any macromonomers either (the term "macromonomer" means a monofunctional monomer containing a pendent group of polymeric nature, and preferably having a molecular mass of greater than 500 g/mol, or alternatively a polymer comprising on only one of its ends a polymerizable end group (or an ethylenically unsaturated group)), which are used in the preparation of a grafted polymer.

It is pointed out that, in the text hereinabove and hereinbelow, the terms "first block" and "second block" do not in any way condition the order of the said blocks in the structure of the polymer.

The first block and the second block of the polymer used in the invention may advantageously be mutually incompatible.

The expression "mutually incompatible blocks" means that the mixture formed from a polymer corresponding to the first block and from a polymer corresponding to the second block is immiscible in the polymerization solvent present in weight majority for the block polymer, at room temperature (25° C.) and atmospheric pressure ($10^5$ Pa), for a content of the polymer mixture of greater than or equal to 5% by weight, relative to the total weight of the mixture of the said polymers and of the said polymerization solvent, it being understood that:

i) the said polymers are present in the mixture in a content such that the respective weight ratio ranges from 10/90 to 90/10, and that ii) each of the polymers corresponding to the first and second blocks has an average (weight-average or number-average) molecular mass equal to that of the block polymer ±15%.

In the case of a mixture of polymerization solvents, should two or more solvents be present in identical mass proportions, the said polymer mixture is immiscible in at least one of them.

Needless to say, in the case of a polymerization performed in a single solvent, this solvent is the majority solvent.

The block polymer according to the invention comprises at least a first block and at least a second block linked together via an intermediate segment comprising at least one constituent monomer of the first block and at least one constituent monomer of the second block. The intermediate segment (also known as the intermediate block) has a glass transition temperature Tg that is between the glass transition temperatures of the first and second blocks.

The intermediate segment is a block comprising at least one constituent monomer of the first block and at least one constituent monomer of the second block of the polymer, which enables these blocks to be "compatibilized".

Advantageously, the intermediate segment comprising at least one constituent monomer of the first block and at least one constituent monomer of the second block of the polymer is a random polymer.

Preferably, the intermediate block is derived essentially from constituent monomers of the first block and of the second block.

The term "essentially" means at least 85%, preferably at least 90%, better still 95% and even better still 100%.

The block polymer according to the invention is advantageously a film-forming block ethylenic polymer.

The term "ethylenic polymer" means a polymer obtained by polymerization of ethylenically unsaturated monomers.

The term "film-forming polymer" means a polymer that is capable of forming, by itself or in the presence of a film-forming auxiliary agent, a continuous film that adheres to a support, especially to keratin materials.

Preferentially, the polymer according to the invention comprises no silicon atoms in its backbone. The term "backbone" means the main chain of the polymer, as opposed to the pendent side chains.

Preferably, the polymer according to the invention is not water-soluble, i.e. the polymer is not soluble in water or in a mixture of water and of linear or branched lower monoalcohols containing from 2 to 5 carbon atoms, for instance ethanol, isopropanol or n-propanol, without pH modification, at an active material content of at least 1% by weight, at room temperature (25° C.)

Preferably, the polymer according to the invention is not an elastomer.

The term "non-elastomeric polymer" means a polymer which, when it is subjected to a constraint intended to pull it (for example by 30% relative to its initial length), does not return to a length substantially identical to its initial length when the constraint ceases.

More specifically, the term "non-elastomeric polymer" denotes a polymer with an instantaneous recovery $R_i$<50% and a delayed recovery $R_{2h}$<70% after having been subjected to a 30% elongation. Preferably, $R_i$ is <30% and $R_{2h}$<50%.

More specifically, the non-elastomeric nature of the polymer is determined according to the following protocol:

A polymer film is prepared by pouring a solution of the polymer into a Teflon-coated mould, followed by drying for 7 days in an environment conditioned at 23±5° C. and 50±10% relative humidity.

A film about 100 μm thick is thus obtained, from which are cut rectangular specimens (for example using a punch) 15 mm wide and 80 mm long.

This sample is subjected to a tensile stress using a machine sold under the reference Zwick, under the same temperature and humidity conditions as for the drying.

The specimens are pulled at a speed of 50 mm/min and the distance between the jaws is 50 mm, which corresponds to the initial length ($l_0$) of the specimen.

The instantaneous recovery $R_i$ is determined in the following manner:

the specimen is pulled by 30% ($\epsilon_{max}$), i.e. about 0.3 times its initial length ($l_0$)

the constraint is released by applying a return speed equal to the tensile speed, i.e. 50 mm/min, and the residual elongation of the specimen is measured as a percentage, after returning to zero load stress ($\epsilon_i$).

The percentage instantaneous recovery ($R_i$) is given by the following formula:

$$R_i=(\epsilon_{max}-\epsilon_i)/\epsilon_{max}\times 100$$

To determine the delayed recovery, the percentage residual elongation of the specimen ($\epsilon_{2h}$) is measured after 2 hours (2 hours after returning to zero load stress).

The percentage delayed recovery ($R_{2h}$) is given by the following formula:

$$R_{2h}=(\epsilon_{max}-\epsilon_{2h})/\epsilon_{max}\times 100$$

Purely as a guide, a polymer according to one embodiment of the invention has an instantaneous recovery $R_i$ of 10% and a delayed recovery $R_{2h}$ of 30%.

The polydispersity index of the polymer of the invention is greater than 2.

Advantageously, the block polymer used in the compositions according to the invention has a polydispersity index I of greater than 2, for example ranging from 2 to 9, preferably greater than or equal to 2.5, for example ranging from 2.5 to 8 and better still greater than or equal to 2.8, especially ranging from 2.8 to 6.

The polydispersity index I of the polymer is equal to the ratio of the weight-average mass Mw to the number-average mass Mn.

The weight-average molar mass (Mw) and number-average molar mass (Mn) are determined by gel permeation liquid chromatography (THF solvent, calibration curve established with linear polystyrene standards, refractometric detector).

The weight-average mass (Mw) of the polymer according to the invention is preferably less than or equal to 300 000; it ranges, for example, from 35 000 to 200 000 and better still from 45 000 to 150 000 g/mol.

The number-average mass (Mn) of the polymer according to the invention is preferably less than or equal to 70 000; it ranges, for example, from 10 000 to 60 000 and better still from 12 000 to 50 000 g/mol.

Preferably, the polydispersity index of the polymer according to the invention is greater than 2, for example ranging from 2 to 9, preferably greater than or equal to 2.5, for example ranging from 2.5 to 8, and better still greater than or equal to 2.8, especially from 2.8 to 6.

First Block with a Tg of Greater than or Equal to 40° C.

The block with a Tg of greater than or equal to 40° C. has, for example, a Tg ranging from 40 to 150° C., preferably greater than or equal to 50° C., for example ranging from 50° C. to 120° C., and better still greater than or equal to 60° C., for example ranging from 60° C. to 120° C.

The glass transition temperatures indicated for the first and second blocks may be theoretical Tg values determined from the theoretical Tg values of the constituent monomers of each of the blocks, which may be found in a reference manual such as the *Polymer Handbook*, 3rd Edition, 1989, John Wiley, according to the following relationship, known as Fox's law:

$$1/Tg = \sum_i (\varpi_i/Tg_i),$$

$\varpi_i$ being the mass fraction of the monomer i in the block under consideration and $Tg_i$ being the glass transition temperature of the homopolymer of the monomer i.

Unless otherwise indicated, the Tg values indicated for the first and second blocks in the present patent application are theoretical Tg values.

The difference between the glass transition temperatures of the first and second blocks is generally greater than 10° C., preferably greater than 20° C. and better still greater than 30° C.

In the present invention, the expression "between . . . and . . . " is intended to denote a range of values for which the limits mentioned are excluded, and "from . . . to . . . " and "ranging from . . . to . . . " are intended to denote a range of values for which the limits are included.

The block with a Tg of greater than or equal to 40° C. may be a homopolymer or a copolymer.

The block with a Tg of greater than or equal to 40° C. may be derived totally or partly from one or more monomers which are such that the homopolymer prepared from these monomers has a glass transition temperature of greater than or equal to 40° C. This block may also be referred to as a "rigid block".

When this block is a homopolymer, it is derived from monomers which are such that the homopolymers prepared from these monomers have glass transition temperatures of greater than or equal to 40° C. This first block may be a homopolymer, formed from only one type of monomer (the Tg of the corresponding homopolymer of which is greater than or equal to 40° C.)

In the case where the first block is a copolymer, it may be totally or partly derived from one or more monomers whose nature and concentration are chosen such that the Tg of the resulting copolymer is greater than or equal to 40° C. The copolymer may comprise, for example:

monomers which are such that the homopolymers prepared from these monomers have Tg values of greater than or equal to 40° C., for example a Tg ranging from 40 to 150° C., preferably greater than or equal to 50° C., for example ranging from 50° C. to 120° C. and better still greater than or equal to 60° C., for example ranging from 60° C. to 120° C., and monomers which are such that the homopolymers prepared from these monomers have Tg values of less than 40° C., chosen from monomers with a Tg of between 20° C. and 40° C. and/or monomers with a Tg of less than or equal to 20° C., for example a Tg ranging from −100° C. to 20° C., preferably less than 15° C., especially ranging from −80° C. to 15° C. and better still less than 10° C., for example ranging from −50° C. to 0° C., as described later.

The first monomers whose homopolymers have a glass transition temperature of greater than or equal to 40° C. are preferably chosen from the following monomers, also known as the main monomers:

methacrylates of formula $CH_2=C(CH_3)-COOR_1$ in which $R_1$ represents a linear or branched unsubstituted alkyl group containing from 1 to 4 carbon atoms, such as a methyl, ethyl, propyl or isobutyl group or $R_8$ represents a $C_4$ to $C_{12}$ cycloalkyl group, preferably a $C_8$ to $C_{12}$ cycloalkyl group, such as isobornyl methacrylate, acrylates of formula $CH_2=CH-COOR_2$ in which $R_2$ represents a $C_4$ to $C_{12}$ cycloalkyl group such as an isobornyl group or a tert-butyl group, (meth)acrylamides of formula:

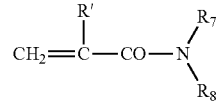

in which $R_7$ and $R_8$, which may be identical or different, each represent a hydrogen atom or a linear or branched $C_1$ to $C_{12}$ alkyl group such as an n-butyl, t-butyl, isopropyl, isohexyl, isooctyl or isononyl group; or $R_7$ represents H and $R_8$ represents a 1,1-dimethyl-3-oxobutyl group, and R' denotes H or methyl. Examples of monomers that may be mentioned include N-butylacrylamide, N-t-butylacrylamide, N-isopropylacrylamide, N,N-dimethylacrylamide and N,N-dibutylacrylamide, and mixtures thereof.

The first block is advantageously obtained from at least one acrylate monomer of formula $CH_2=CH-COOR_2$ and from at least one methacrylate monomer formula $CH_2=C(CH_3)-COOR_2$ in which $R_2$ represents a $C_4$ to $C_{12}$ cycloalkyl group, preferably a $C_8$ to $C_{12}$ cycloalkyl, such as isobornyl. The monomers and the proportions thereof are preferably chosen such that the glass transition temperature of the first block is greater than or equal to 40° C.

According to one embodiment, the first block is obtained from:
 i) at least one acrylate monomer of formula $CH_2=CH-COOR_2$ in which $R_2$ represents a $C_4$ to $C_{12}$ cycloalkyl group, preferably a $C_8$ to $C_{12}$ cycloalkyl, such as isobornyl,
 ii) and at least one methacrylate monomer of formula $CH_2=C(CH_3)-COOR'_2$ in which $R'_2$ represents a $C_4$ to $C_{12}$ cycloalkyl group, preferably a $C_8$ to $C_{12}$ cycloalkyl, such as isobornyl.

According to one embodiment, the first block is obtained from at least one acrylate monomer of formula $CH_2=CH-COOR_2$ in which $R_2$ represents a $C_8$ to $C_{12}$ cycloalkyl, such as isobornyl, and from at least one methacrylate monomer of formula $CH_2=C(CH_3)-COOR'_2$ in which $R'_2$ represents a $C_8$ to $C_{12}$ cycloalkyl, such as isobornyl.

Preferably, $R_2$ and $R'_2$ simultaneously or independently represent an isobornyl group.

Preferably, the block copolymer comprises from 50% to 80% by weight of isobornyl methacrylate/acrylate, from 10% to 30% by weight of isobutyl acrylate and from 2% to 10% by weight of acrylic acid.

The first block may be obtained exclusively from the said acrylate monomer and from the said methacrylate monomer.

The acrylate monomer and the methacrylate monomer are preferably in mass proportions of between 30/70 and 70/30, preferably between 40/60 and 60/40 and especially of about 50/50.

The proportion of the first block advantageously ranges from 20% to 90%, better still from 30% to 80% and even better still from 60% to 80% by weight of the polymer.

According to one embodiment, the first block is obtained by polymerization of isobornyl methacrylate and isobornyl acrylate.

Second Block with a Glass Transition Temperature of Less than 20° C.

The second block advantageously has a glass transition temperature Tg of less than or equal to 20° C., for example a Tg ranging from −100° C. to 20° C., preferably less than or equal to 15° C., especially ranging from −80° C. to 15° C., and better still less than or equal to 10° C., for example ranging from −100° C. to 10° C. and especially ranging from −30° C. to 10° C.

The second block is totally or partly derived from one or more second monomers, which are such that the homopolymer prepared from these monomers has a glass transition temperature of less than or equal to 20° C.

This block may also be referred to as a "flexible block".

The monomer with a Tg of less than or equal to 20° C. (known as the second monomer) is preferably chosen from the following monomers:
 the acrylates of formula $CH_2=CHCOOR_3$,
 $R_3$ representing a linear or branched, unsubstituted $C_1$-$C_{12}$ alkyl group, with the exception of a tert-butyl group, in which is (are) optionally intercalated one or more heteroatoms chosen from O, N and S;
 the methacrylates of formula $CH_2=C(CH_3)-COOR_4$,
 $R_4$ representing a linear or branched, unsubstituted $C_6$-$C_{12}$ alkyl group, in which is (are) optionally intercalated one or more heteroatoms chosen from O, N and S;
 vinyl esters of formula $R_5-CO-O-CH=CH_2$, in which $R_5$ represents a linear or branched $C_4$-$C_{12}$ alkyl group;
 ethers of vinyl alcohol and of a $C_4$ to $C_{12}$ alcohol;
 N—($C_4$-$C_{12}$ alkyl)acrylamides, such as N-octylacrylamide;
 and mixtures thereof.

The preferred monomers with a Tg of less than or equal to 20° C. are isobutyl acrylate and 2-ethylhexyl acrylate, or mixtures thereof in all proportions.

Each of the first and second blocks may contain in minor proportion at least one constituent monomer of the other block.

Thus, the first block may contain at least one constituent monomer of the second block, and vice versa.

Each of the first and/or second blocks may comprise, in addition to the monomers indicated above, one or more other monomers, known as additional monomers, which are different from the main monomers mentioned previously.

The nature and amount of this or these additional monomer(s) are chosen such that the block in which they are present has the desired glass transition temperature.

This additional monomer is chosen, for example, from:
 ethylenically unsaturated monomers comprising at least one tertiary amine function, for instance 2-vinylpyridine, 4-vinylpyridine, dimethylaminoethyl methacrylate, diethylaminoethyl methacrylate and dimethylaminopropylmethacrylamide, and salts thereof,
 methacrylates of formula $CH_2=C(CH_3)-COOR_6$,
 in which $R_6$ represents a linear or branched alkyl group containing from 1 to 4 carbon atoms, such as a methyl, ethyl, propyl or isobutyl group, the said alkyl group being substituted with one or more substituents chosen from hydroxyl groups (for instance 2-hydroxypropyl methacrylate and 2-hydroxyethyl methacrylate) and halogen atoms (Cl, Br, I or F), such as trifluoroethyl methacrylate,
 methacrylates of formula $CH_2=C(CH_3)-COOR_9$,
 $R_9$ representing a linear or branched $C_6$ to $C_{12}$ alkyl group in which one or more heteroatoms chosen from O, N and S are optionally intercalated, the said alkyl group being substituted with one or more substituents chosen from hydroxyl groups and halogen atoms (Cl, Br, I or F);
 acrylates of formula $CH_2=CHCOOR_{10}$,
 $R_{10}$ representing a linear or branched $C_1$ to $C_{12}$ alkyl group substituted with one or more substituents chosen from hydroxyl groups and halogen atoms (Cl, Br, I or F), such as 2-hydroxypropyl acrylate and 2-hydroxyethyl acrylate, or $R_{10}$ represents a $C_1$ to $C_{12}$ alkyl-O—POE (polyoxyethylene) with repetition of the oxyethylene unit 5 to 10 times, for example methoxy-POE, or $R_{10}$ represents a polyoxyethylenated group comprising from 5 to 10 ethylene oxide units.

In particular, the first block may comprise as additional monomer:
 (meth)acrylic acid, preferably acrylic acid,
 tert-butyl acrylate, the methacrylates of formula $CH_2=C(CH_3)-COOR_1$ in which $R^1$ represents a linear or branched unsubstituted alkyl group, containing from 1 to 4 carbon atoms, such as a methyl, ethyl, propyl or isobutyl group, (meth)acrylamides of formula:

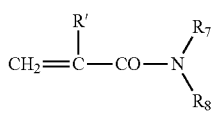

in which $R_7$ and $R_8$, which may be identical or different, each represent a hydrogen atom or a linear or branched $C_1$ to $C_{12}$ alkyl group such as an n-butyl, t-butyl, isopropyl, isohexyl, isooctyl or isononyl group; or $R_7$ represents H and $R_8$ represents a 1,1-dimethyl-3-oxobutyl group, and R' denotes H or methyl. Examples of monomers that may be mentioned include N-butylacrylamide, N-t-butylacrylamide, N-isopropylacrylamide, N,N-dimethylacrylamide and N,N-dibutylacrylamide, and mixtures thereof.

The additional monomer may represent 0.5% to 30% by weight relative to the weight of the polymer. According to one embodiment, the polymer of the invention does not contain any additional monomer.

Preferably, the polymer of the invention comprises at least isobornyl acrylate and isobornyl methacrylate monomers in the first block and isobutyl acrylate and acrylic acid monomers in the second block.

Preferably, the polymer comprises at least isobornyl acrylate and isobornyl methacrylate monomers in equivalent weight proportion in the first block and isobutyl acrylate and acrylic acid monomers in the second block.

Preferably, the polymer comprises at least isobornyl acrylate and isobornyl methacrylate monomers in equivalent weight proportion in the first block, and isobutyl acrylate and acrylic acid monomers in the second block, the first block representing 70% of the weight of the polymer.

Preferably, the polymer comprises at least isobornyl acrylate and isobornyl methacrylate monomers in equivalent weight proportion in the first block, and isobutyl acrylate and acrylic acid monomers in the second block. Preferably, the block with a Tg of greater than 40° C. represents 70% of the weight of the polymer, and acrylic acid represents 5% of the weight of the polymer.

According to one embodiment, the first block does not comprise any additional monomer.

According to one preferred embodiment, the second block comprises acrylic acid as additional monomer. In particular, the second block is advantageously obtained from an acrylic acid monomer and from at least one other monomer with a Tg of less than or equal to 20° C.

The block copolymer may advantageously comprise more than 2% by weight of acrylic acid monomers, especially from 2% to 15% by weight, for example from 3% to 15% by weight, in particular from 4% to 15% by weight or even from 4% to 10% by weight of acrylic acid monomers, relative to the total weight of the said copolymer.

The constituent monomers of the second block and the proportions thereof are chosen such that the glass transition temperature of the second block is less than or equal to 20° C.

Intermediate Segment

The intermediate segment (also known as the intermediate block) links the first block and the second block of the polymer used according to the present invention. The intermediate segment results from the polymerization:

i) of the first monomer(s), and optionally of the additional monomer(s), that are still available after their polymerization to a maximum degree of conversion of 90% to form the first block, ii) and of the second monomer(s), and optionally of the additional monomer(s), added to the reaction mixture.

The formation of the second block is initiated when the first monomers no longer react or are no longer incorporated into the polymer chain, either because they are all consumed or because their reactivity no longer allows them to be.

Thus, the intermediate segment comprises the available first monomers, resulting from a degree of conversion of these first monomers of less than or equal to 90%, during the introduction of the second monomer(s) during the synthesis of the polymer.

The intermediate segment of the block polymer is a random polymer (which may also be referred to as a random block). This means that it comprises a random distribution of the first monomer(s) and of the second monomer(s) and also of the additional monomer(s) optionally present.

Thus, the intermediate segment is a random block, as are the first block and the second block if they are not homopolymers (i.e. if they are both formed from at least two different monomers).

Process for Preparing the Copolymer:

The block ethylenic copolymer according to the invention is prepared by free-radical polymerization, according to the well-known techniques for this type of polymerization.

Free-radical polymerization is performed in the presence of an initiator whose nature is appropriate, in a known manner, as a function of the desired polymerization temperature and of the polymerization solvent. In particular, the initiator may be chosen from initiators containing a peroxide function, redox couples, or other radical polymerization initiators known to those skilled in the art.

In particular, examples of initiators containing a peroxide function that may be mentioned include:

a. peroxyesters, such as tert-butyl peroxyacetate, tert-butyl perbenzoate, tert-butyl peroxy-2-ethylhexanoate (Trigonox 21S from Akzo Nobel) and 2,5-bis(2-ethylhexanoylperoxy)-2,5-dimethyl-hexane (Trigonox 141 from Akzo Nobel);

b. peroxydicarbonates, such as diisopropyl peroxydicarbonate;

c. peroxy ketones, such as methyl ethyl ketone peroxide;

d. hydroperoxides, such as hydrogen peroxide ($H_2O_2$) and tert-butyl hydroperoxide;

e. diacyl peroxides, such as acetyl peroxide and benzoyl peroxide;

f. dialkyl peroxides, such as di-tert-butyl peroxide;

g. inorganic peroxides, such as potassium peroxodisulfate ($K_2S_2O_8$).

An example of an initiator in the form of a redox couple that may be mentioned is the potassium thiosulfate+potassium peroxodisulfate couple.

According to one preferred embodiment, the initiator is chosen from organic peroxides comprising from 8 to 30 carbon atoms. Preferably, the initiator used is 2,5-bis(2-ethylhexanoylperoxy)-2,5-dimethyl-hexane sold under the reference Trigonox® 141 by the company Akzo Nobel.

The block copolymer used according to the invention is prepared by free-radical polymerization rather than by controlled or living polymerization. In particular, the polymerization of the block ethylenic copolymer is performed in the absence of control agents, and in particular in the absence of control agents conventionally used in living or controlled polymerization processes, for instance nitroxides, alkoxyamines, dithioesters, dithiocarbamates, dithiocarbonates or xanthates, trithiocarbonates and copper-based catalysts.

As indicated previously, the intermediate segment is a random block, as are the first block and the second block if they are not homopolymers (i.e. if they are both formed from at least two different monomers).

The block copolymer may be prepared by free-radical polymerization, and in particular via a process that consists in mixing, in the same reactor, a polymerization solvent, an initiator, at least one monomer with a glass transition temperature of greater than or equal to 40° C. and at least one monomer with a glass transition temperature of less than or equal to 20° C., according to the following sequence:

some of the polymerization solvent and optionally some of the initiator and of the monomers of the first addition are placed in the reactor, and the mixture is heated to a reaction temperature of between 60 and 120° C., the said at least one first monomer with a Tg of greater than or equal to 40° C. and optionally some of the initiator are then introduced, in a first addition, and the mixture is left to react for a time T corresponding to a maximum degree of conversion of the said monomers of 90%, more polymerization initiator and the said at least one second monomer with a glass transition temperature of less than or equal to 20° C. are then placed in the reactor, in a second addition, and the mixture is left to react for a time T' after which the degree of conversion of the said monomers reaches a plateau, the reaction mixture is cooled to room temperature.

Preferably, the copolymer may be prepared by free-radical polymerization, in particular via a process that consists in mixing, in the same reactor, a polymerization solvent, an initiator, an acrylic acid monomer, at least one monomer with a glass transition temperature of less than or equal to 20° C., at least one acrylate monomer of formula $CH_2=CH-COOR_2$ in which $R_2$ represents a $C_4$ to $C_{12}$ cycloalkyl group, and at least one methacrylate monomer of formula $CH_2=C(CH_3)-COOR'_2$ in which $R'_2$ represents a $C_4$ to $C_{12}$ cycloalkyl group, according to the following sequence of steps:

some of the polymerization solvent and optionally some of the initiator and of the monomers of the first addition are placed in the reactor, and the mixture is heated to a reaction temperature of between 60 and 120° C., the said at least one acrylate monomer of formula $CH_2=CH-COOR_2$ and the said at least one methacrylate monomer of formula $CH_2=C(CH_3)-COOR'_2$ as monomers with a Tg of greater than or equal to 40° C., and optionally some of the initiator, are then introduced, in a first addition, and the mixture is left to react for a time T corresponding to a maximum degree of conversion of the said monomers of 90%, more polymerization initiator, the acrylic acid monomer and the said at least one second monomer with a glass transition temperature of less than or equal to 20° C. are then placed in the reactor, in a second addition, and the mixture is left to react for a time T' after which the degree of conversion of the said monomers reaches a plateau, the reaction mixture is cooled to room temperature.

The term "polymerization solvent" means a solvent or a mixture of solvents. In particular, as polymerization solvents that may be used, mention may be made of:

ketones that are liquid at room temperature, such as methyl ethyl ketone, methyl isobutyl ketone, diisobutyl ketone, isophorone, cyclohexanone or acetone;

propylene glycol ethers that are liquid at room temperature, such as propylene glycol monomethyl ether, propylene glycol monomethyl ether acetate or dipropylene glycol mono-n-butyl ether;

short-chain esters (containing from 3 to 8 carbon atoms in total) such as ethyl acetate, methyl acetate, propyl acetate, n-butyl acetate or isopentyl acetate;

ethers that are liquid at room temperature, such as diethyl ether, dimethyl ether or dichlorodiethyl ether;

alkanes that are liquid at room temperature, such as decane, heptane, dodecane, isododecane, cyclohexane or isohexadecane;

cyclic aromatic compounds that are liquid at room temperature, such as toluene or xylene;

aldehydes that are liquid at room temperature, such as benzaldehyde or acetaldehyde;

and mixtures thereof.

Conventionally, the polymerization solvent is a volatile oil with a flash point of less than 80° C. The flash point is measured in particular according to standard ISO 3679.

The polymerization solvent may be chosen especially from ethyl acetate, butyl acetate, alcohols such as isopropanol or ethanol, and aliphatic alkanes such as isododecane, and mixtures thereof. Preferably, the polymerization solvent is a mixture of butyl acetate and isopropanol or isododecane.

According to another embodiment, the copolymer may be prepared by free-radical polymerization according to the preparation process that consists in mixing, in the same reactor, a polymerization solvent, an initiator, at least one monomer with a glass transition temperature of less than or equal to 20° C., and at least one monomer with a Tg of greater than or equal to 40° C., according to the following sequence of steps:

some of the polymerization solvent and optionally some of the initiator and of the monomers of the first addition are placed in the reactor, and the mixture is heated to a reaction temperature of between 60 and 120° C., the said at least one monomer with a glass transition temperature of less than or equal to 20° C. and optionally some of the initiator are then introduced, in a first addition, and the mixture is left to react for a time T corresponding to a maximum degree of conversion of the said monomers of 90%, more polymerization initiator and the said at least one monomer with a Tg of greater than or equal to 40° C. are then placed in the reactor, in a second addition, and the mixture is left to react for a time T' after which the degree of conversion of the said monomers reaches a plateau, the reaction mixture is cooled to room temperature.

According to one preferred embodiment, the copolymer may be prepared by free-radical polymerization according to a preparation process that consists in mixing, in the same reactor, a polymerization solvent, an initiator, an acrylic acid monomer, at least one monomer with a glass transition temperature of less than or equal to 20° C., at least one monomer with a Tg of greater than or equal to 40° C., and, in particular as monomers with a Tg of greater than or equal to 40° C., at least one acrylate monomer of formula $CH_2=CH-COOR_2$ in which $R_2$ represents a $C_4$ to $C_{12}$ cycloalkyl group, and at least one methacrylate monomer of formula $CH_2=C(CH_3)-COOR'_2$ in which $R'_2$ represents a $C_4$ to $C_{12}$ cycloalkyl group, according to the following sequence of steps:

some of the polymerization solvent and optionally some of the initiator and of the monomers of the first addition are placed in the reactor, and the mixture is heated to a reaction temperature of between 60 and 120° C., the acrylic acid monomer and the said at least one monomer with a glass transition temperature of less than or equal to 20° C. and optionally some of the initiator are then introduced, in a first addition, and the mixture is left to react for a time T corresponding to a maximum degree of conversion of the said monomers of 90%, more polymerization initiator, the said at least one acrylate monomer of formula $CH_2=CH—COOR_2$ and the said at least one methacrylate monomer of formula $CH_2=C(CH_3)—COOR'_2$ as monomers with a Tg of greater than or equal to 40° C. are then placed in the reactor, in a second addition, and the mixture is left to react for a time T' after which the degree of conversion of the said monomers reaches a plateau, the reaction mixture is cooled to room temperature.

The polymerization temperature is preferably about 90° C.

The reaction time after the second addition is preferably between 3 and 6 hours.

Preferably, the block ethylenic copolymer is present in the composition in an active material content ranging from 0.1% to 60%, better still from 0.5% to 50%, better still from 1% to 30% and even better still from 1% to 40% by weight relative to the total weight of the composition.

Distillation of the Synthesis Solvent

It is possible to perform a step of total or partial removal of the said volatile oil or solvent (conventionally isododecane). This is then performed in particular by distillation, optionally under vacuum, and optional addition of non-volatile hydrocarbon-based ester oil comprising at least 16 carbon atoms and having a molar mass of less than 650 g/mol, such as octyldodecyl neopentanoate (especially 2-octyldodecyl neopentanoate).

This step is performed at elevated temperature and optionally under vacuum to distil off a maximum amount of volatile synthesis solvent, and is known to those skilled in the art.

2. Vinyl Polymer Comprising at Least One Carbosiloxane Dendrimer-based Unit

According to a second embodiment of the invention, the film-forming polymer present in the composition according to the invention is a vinyl polymer comprising at least one carbosiloxane dendrimer-based unit.

The vinyl polymer may especially have a backbone and at least one side chain, which comprises a carbosiloxane dendrimer structure. The term "carbosiloxane dendrimer structure" in the context of the present invention represents a molecular structure with branched groups of high molecular masses with high regularity in the radial direction starting from the bond to the backbone. Such carbosiloxane dendrimer structures are described in the form of a highly branched siloxane-silylalkylene copolymer in the laid-open Japanese patent application Kokai 9-171 154.

The vinyl polymer contains carbosiloxane dendrimer-based units that may be represented by the following general formula:

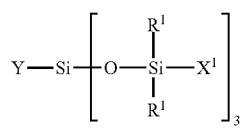

in which $R^1$ represents an aryl group or an alkyl group containing from 1 to 10 carbon atoms, and $X^1$ represents a silylalkyl group which, when i=1, is represented by the formula:

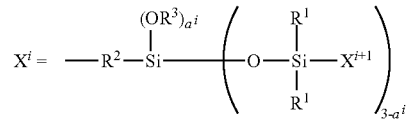

in which $R^1$ is the same as defined above, $R^2$ represents an alkylene group containing from 2 to 10 carbon atoms, $R^3$ represents an alkyl group containing from 1 to 10 carbon atoms, $X^{i+1}$ represents a hydrogen atom, an alkyl group containing from 1 to 10 carbon atoms, an aryl group or the silylalkyl group defined above with i=i+1; i is an integer from 1 to 10 which represents the generation of the said silylalkyl group, and $a^i$ is an integer from 0 to 3; Y represents an organic group that may be polymerized using radicals chosen from the group consisting of an organic group that contains a methacrylic group or an acrylic group and that is represented by the formulae:

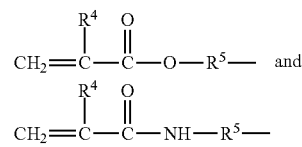

in which $R^4$ represents a hydrogen atom or an alkyl group, $R^5$ represents an alkylene group containing from 1 to 10 carbon atoms, such as a methylene group, an ethylene group, a propylene group or a butylene group, the methylene group and the propylene group being preferred; and an organic group that contains a styryl group and that is represented by the formula:

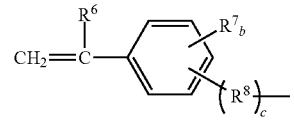

in which $R^6$ represents a hydrogen atom or an alkyl group, $R^7$ represents an alkyl group containing from 1 to 10 carbon atoms, such as a methyl group, ethyl group, a propyl group or a butyl group, the methyl group being preferred, $R^8$ represents an alkylene group containing from 1 to 10 carbon atoms, such as a methylene group, an ethylene group, a propylene group or a butylene group, the ethylene group being preferred, b is an integer from 0 to 4, and c is 0 or 1 such that if c is 0, $—(R^8)_c—$ represents a bond, $R^1$ represents an aryl group or an alkyl group containing from 1 to 10 carbon atoms, in which the alkyl group is preferably represented by a methyl group, an ethyl group, a propyl group, a butyl group, a pentyl group, an isopropyl group, an isobutyl group, a cyclopentyl group or a cyclohexyl group, and in which the aryl group is preferably represented by a phenyl group and a naphthyl group, in which the methyl and phenyl groups are more particularly preferred, and the methyl group is preferred among all.

The vinyl polymer that contains a carbosiloxane dendrimer structure may be the product of polymerization of (A) from 0 to 99.9 parts by weight of a monomer of vinyl type; and (B) from 100 to 0.1 part by weight of a carbosiloxane dendrimer containing an organic group that may be polymerized using radicals, represented by the general formula:

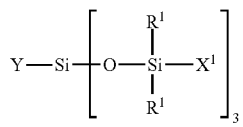

in which Y represents an organic group that may be polymerized using radicals, $R^1$ represents an aryl group or an alkyl group containing from 1 to 10 carbon atoms, and $X^1$ represents a silylalkyl group which, when i=1, is represented by the formula:

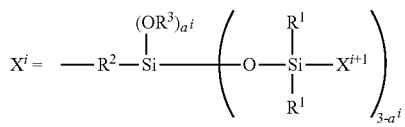

in which $R^1$ is the same as defined above, $R^2$ represents an alkylene group containing from 2 to 10 carbon atoms, $R^3$ represents an alkyl group containing from 1 to 10 carbon atoms, $X^{i+1}$ represents a hydrogen atom, an alkyl group containing from 1 to 10 carbon atoms, an aryl group, or the silylalkyl group defined above with i=i+1; i is an integer from 1 to 10 that represents the generation of the said silylalkyl group, and $a^i$ is an integer from 0 to 3; in which the said organic group that may be polymerized with radicals contained in the component (B) is chosen from the group consisting of an organic group that contains a methacrylic group or an acrylic group and that is represented by the formulae:

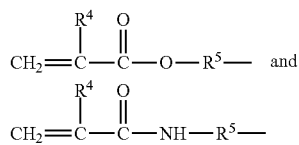

in which $R^4$ represents a hydrogen atom or an alkyl group, $R^5$ represents an alkylene group containing from 1 to 10 carbon atoms; and an organic group that contains a styryl group and that is represented by the formula:

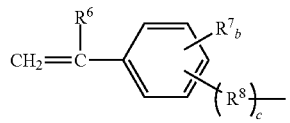

in which $R^6$ represents a hydrogen atom or an alkyl group, $R^7$ represents an alkyl group containing from 1 to 10 carbon atoms, $R^8$ represents an alkylene group containing from 1 to 10 carbon atoms, b is an integer from 0 to 4, and c is 0 or 1. When c is 0, $-(R^8)_c-$ represents a bond.

The monomer of vinyl type that is component (A) in the vinyl polymer is a monomer of vinyl type that contains a radical-polymerizable vinyl group. There is no particular limitation as regards the type of such a monomer. The following are examples of this type of vinyl monomer: methyl methacrylate, ethyl methacrylate, n-propyl methacrylate, isopropyl methacrylate or a methacrylate of a lower alkyl analogue; glycidyl methacrylate; n-butyl methacrylate, isobutyl methacrylate, tert-butyl methacrylate, n-hexyl methacrylate, methacrylic acid, cyclohexyl methacrylate, 2-ethylhexyl methacrylate, octyl methacrylate, lauryl methacrylate, stearyl methacrylate or a higher-analogue methacrylate; vinyl acetate, vinyl propionate or a vinyl ester of a lower fatty acid analogue; vinyl caproate, vinyl 2-ethylhexoate, vinyl laurate, vinyl stearate or an ester of a higher fatty acid analogue; styrene, vinyltoluene, benzyl methacrylate, phenoxyethyl methacrylate, vinyl-pyrrolidone or similar vinylaromatic monomers; methacrylamide, N-methylolmethacrylamide, N-methoxy-methylmethacrylamide, isobutoxymethoxymethacrylamide, N,N-dimethylmethacrylamide or similar monomers of vinyl type containing amide groups; hydroxyethyl methacrylate, hydroxypropyl methacrylate or similar monomers of vinyl type containing hydroxyl groups; methacrylic acid, itaconic acid, crotonic acid, fumaric acid, maleic acid or similar monomers of vinyl type containing a carboxylic acid group; tetrahydrofurfuryl methacrylate, butoxyethyl methacrylate, ethoxydiethylene glycol methacrylate, polyethylene glycol methacrylate, polypropylene glycol monomethacrylate, hydroxybutyl vinyl ether, cetyl vinyl ether, 2-ethylhexyl vinyl ether or a similar monomer of vinyl type with ether bonds; methacryloxypropyl-trimethoxysilane, polydimethylsiloxane containing a methacrylic group on one of its molecular ends, polydimethylsiloxane containing a styryl group on one of its molecular ends, or a similar silicone compound containing unsaturated groups; butadiene; vinyl chloride; vinylidene chloride; methacrylonitrile; dibutyl fumarate; anhydrous maleic acid; anhydrous succinic acid; methacryl glycidyl ether; an organic salt of an amine, an ammonium salt, and an alkali metal salt of methacrylic acid, of itaconic acid, of crotonic acid, of maleic acid or of fumaric acid; a radical-polymerizable unsaturated monomer containing a sulfonic acid group such as a styrene-sulfonic acid group; a quaternary ammonium salt derived from methacrylic acid, such as 2-hydroxy-3-methacryloxypropyltrimethylammonium chloride; and a methacrylic acid ester of an alcohol containing a tertiary amine group, such as a methacrylic acid ester of diethylamine.

Multifunctional monomers of vinyl type may also be used. The following represent examples of such compounds: trimethylolpropane trimethacrylate, pentaerythrityl trimethacrylate, ethylene glycol dimethacrylate, tetraethylene glycol dimethacrylate, polyethylene glycol dimethacrylate, 1,4-butanediol dimethacrylate, 1,6-hexanediol dimethacrylate, neopentyl glycol dimethacrylate, trimethylolpropane-trioxyethyl methacrylate, tris(2-hydroxyethyl)-isocyanurate dimethacrylate, tris(2-hydroxyethyl)-isocyanurate trimethacrylate, polydimethylsiloxane capped with styryl groups containing divinylbenzene groups on both ends, or similar silicone compounds containing unsaturated groups.

The carbosiloxane dendrimer, which is component (B), is represented by the following formula:

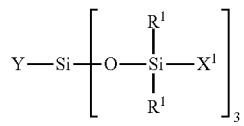

The following represent the preferred examples of radical-polymerizable organic group Y: an acryloxymethyl group, a 3-acryloxypropyl group, a methacryloxymethyl group, a 3-methacryloxypropyl group, a 4-vinylphenyl group, a 3-vinylphenyl group, a 4-(2-propenyl)phenyl group, a 3-(2-propenyl)phenyl group, a 2-(4-vinylphenyl)ethyl group, a 2-(3-vinyl-phenyl)ethyl group, a vinyl group, an allyl group, a methallyl group and a 5-hexenyl group.

$R^1$ represents an alkyl group or an aryl group containing from 1 to 10 carbon atoms, in which the alkyl group may be a methyl group, an ethyl group, a propyl group, a butyl group, a pentyl group, an isopropyl group, an isobutyl group, a cyclopentyl group or a cyclohexyl group; and the aryl group may be a phenyl group or a naphthyl group. The methyl and phenyl groups are particularly preferred, the methyl group being preferred among all. $X^1$ represents a silylalkyl group that is represented by the following formula, when i is equal to 1:

in which $R^2$ represents an alkylene group containing from 2 to 10 carbon atoms, such as an ethylene group, a propylene group, a butylene group, a hexylene group or a similar linear alkylene group; a methylmethylene group, a methylethylene group, a 1-methylpentylene group, a 1,4-dimethylbutylene group or a similar branched alkylene group. The ethylene, methylethylene, hexylene, 1-methylpentylene and 1,4-dimethylbutylene groups are preferred among all. $R^3$ represents an alkyl group containing from 1 to 10 carbon atoms, such as methyl, ethyl, propyl, butyl and isopropyl groups. $R^1$ is the same as defined above. $X^{i+1}$ represents a hydrogen atom, an alkyl group containing from 1 to 10 carbon atoms, an aryl group or the silylalkyl group with i=i+1. $a^i$ is an integer from 0 to 3, and i is an integer from 1 to 10 that indicates the generation number, which represents the number of repetitions of the silylalkyl group.

For example, when the generation number is equal to 1, the carbosiloxane dendrimer may be represented by the first general formula shown below, in which Y, $R^2$ and $R^3$ are the same as defined above, $R^{12}$ represents a hydrogen atom or is identical to $R^1$; $a^1$ is identical to $a^i$. Preferably, the mean total number of groups $OR^3$ in a molecule is within the range from 0 to 7. When the generation number is equal to 2, the carbosiloxane dendrimer may be represented by the second general formula shown below, in which Y, $R^1$, $R^2$, $R^3$ and $R^{12}$ are the same as defined above; $a^1$ and $a^2$ represent the $a^i$ of the indicated generation. Preferably, the mean total number of groups $OR^3$ in a molecule is within the range from 0 to 25. When the generation number is equal to 3, the carbosiloxane dendrimer is represented by the third general formula shown below, in which Y, $R^1$, $R^2$, $R^3$ and $R^{12}$ are the same as defined above; $a^1$, $a^2$ and $a^3$ represent the $a^i$ of the indicated generation. Preferably, the total mean number of groups $OR^3$ in a molecule is within the range from 0 to 79.

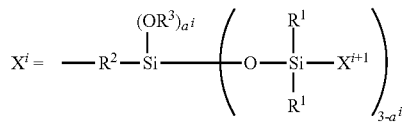

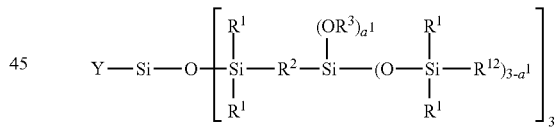

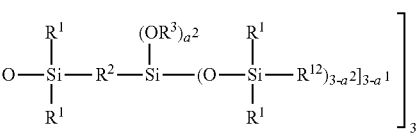

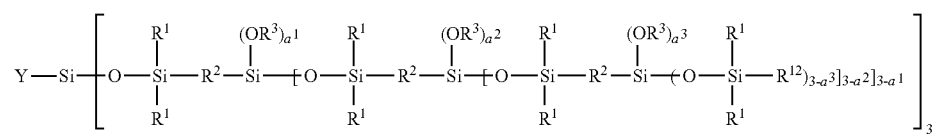

A carbosiloxane dendrimer that contains a radical-polymerizable organic group may be represented by the following mean structural formulae:
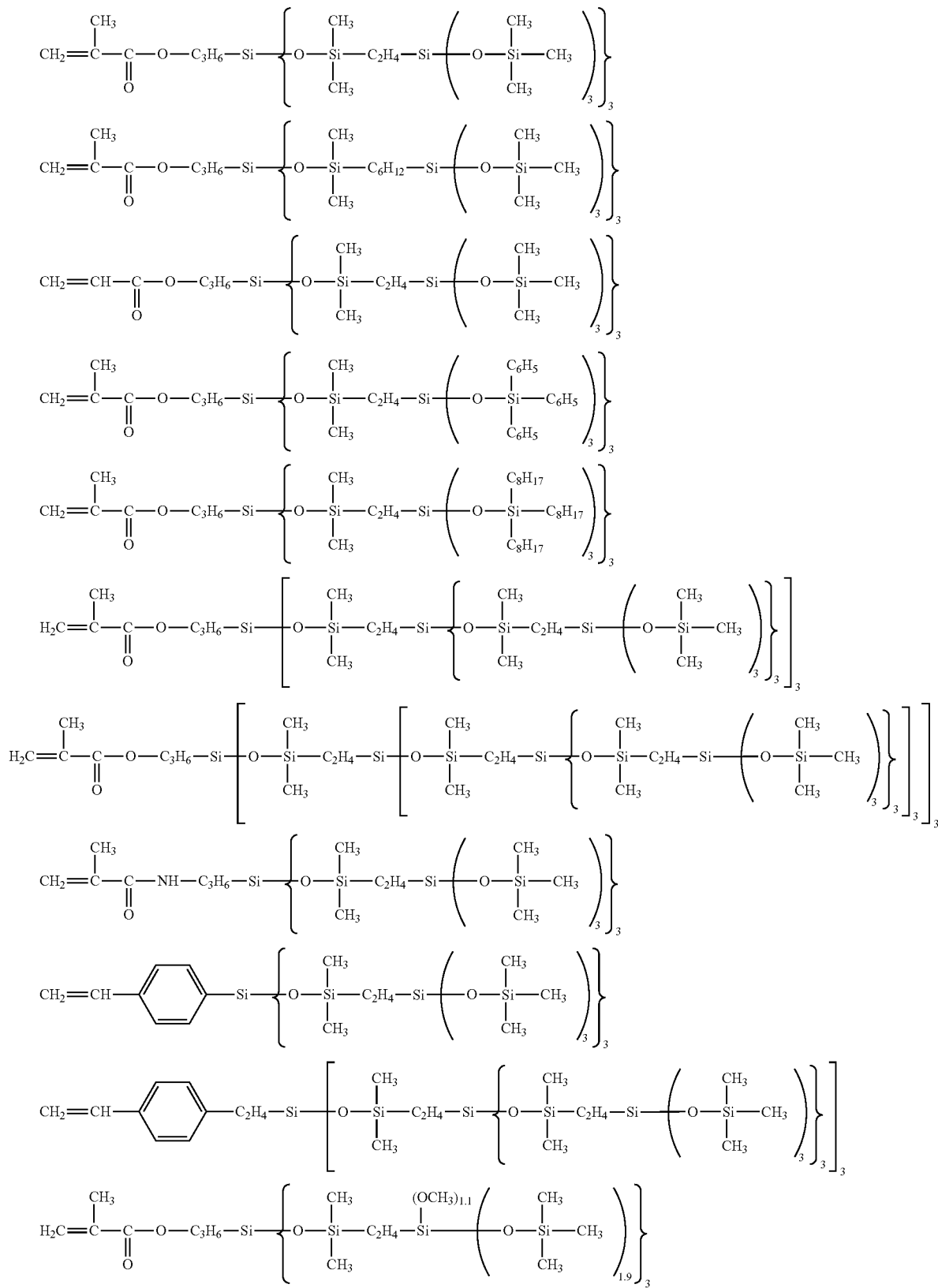

-continued

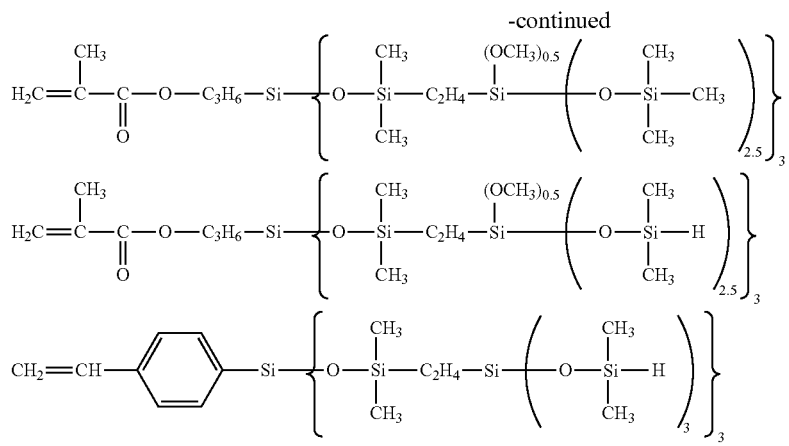

The carbosiloxane dendrimer may be manufactured according to the process for manufacturing a branched silalkylene siloxane described in Japanese patent application Hei 9-171 154. For example, it may be produced by subjecting an organosilicon compound containing a hydrogen atom linked to a silicon atom, represented by the following general formula:

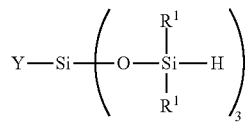

and an organosilicon compound containing an alkenyl group, to a hydrosilylation reaction. In the above formula, the organosilicon compound may be represented by 3-methacryloxypropyltris(dimethyl-siloxy)silane, 3-acryloxypropyltris(dimethylsiloxy)-silane and 4-vinylphenyltris(dimethylsiloxy)silane. The organosilicon compound that contains an alkenyl group may be represented by vinyltris(trimethylsiloxy)silane, vinyltris(dimethylphenylsiloxy)silane, and 5-hexenyl-tris(trimethylsiloxy)silane. The hydrosilylation reaction is performed in the presence of a chloroplatinic acid, a complex of vinylsiloxane and of platinum, or a similar transition metal catalyst.

In the vinyl polymer that contains a dendrimer structure, the polymerization ratio between the components (A) and (B), in terms of the weight ratio between (A) and (B), may be within the range from 0/100 to 99.9/0.1 and preferably within the range from 1/99 to 99/1. A ratio between the components (A) and (B) of 0/100 means that the compound becomes a homopolymer of component (B).

The vinyl polymer contains a carbosiloxane dendrimer structure and this polymer may be obtained by copolymerization of the components (A) and (B), or by polymerization of the component (B) alone. The polymerization may be a free-radical polymerization or an ionic polymerization, but free-radical polymerization is preferred. The polymerization may be performed by bringing about a reaction between the components (A) and (B) in a solution for a period of from 3 to 20 hours in the presence of a radical initiator at a temperature of from 50° C. to 150° C. A suitable solvent for this purpose is hexane, octane, decane, cyclohexane or a similar aliphatic hydrocarbon; benzene, toluene, xylene or a similar aromatic hydrocarbon; diethyl ether, dibutyl ether, tetrahydrofuran, dioxane or similar ethers; acetone, methyl ethyl ketone, methyl isobutyl ketone, diisobutyl ketone or similar ketones; methyl acetate, ethyl acetate, butyl acetate, isobutyl acetate or similar esters; methanol, ethanol, isopropanol, butanol or similar alcohols; octamethylcyclotetrasiloxane, decamethylcyclopentasiloxane, hexamethyldisiloxane, octamethyltrisiloxane or a similar organosiloxane oligomer. A radical initiator may be any compound known in the art for standard free-radical polymerization reactions. The specific examples of such radical initiators are 2,2'-azobis(isobutyronitrile), 2,2'-azobis(2-methylbutyronitrile), 2,2'-azobis(2,4-dimethylvaleronitrile) or similar compounds of azobis type; benzoyl peroxide, lauroyl peroxide, tert-butyl peroxybenzoate, tert-butyl peroxy-2-ethylhexanoate or a similar organic peroxide. These radical initiators may be used alone or in a combination of two or more. The radical initiators may be used in an amount of from 0.1 to 5 parts by weight per 100 parts by weight of the components (A) and (B). A chain-transfer agent may be added. The chain-transfer agent may be 2-mercaptoethanol, butyl mercaptan, n-dodecyl mercaptan, 3-mercaptopropyltrimethoxysilane, a polydimethyl-siloxane containing a mercaptopropyl group or a similar compound of mercapto type; methylene chloride, chloroform, carbon tetrachloride, butyl bromide, 3-chloropropyltrimethoxysilane or a similar halogenated compound. In the manufacture of the polymer of vinyl type, after the polymerization, the residual unreacted vinyl monomer may be removed under conditions of heating under vacuum.

To facilitate the preparation of the mixture of the starting material of cosmetic products, the number-average molecular mass of the vinyl polymer containing a carbosiloxane dendrimer may be chosen within the range between 3000 and 2 000 000 and preferably between 5000 and 800 000. It may be a liquid, a gum, a paste, a solid, a powder or any other form. The preferred forms are solutions consisting of the dilution of a dispersion or of a powder in solvents.

The vinyl polymer may be a dispersion of a polymer of vinyl type having a carbosiloxane dendrimer structure in its side molecular chain, in a liquid such as a silicone oil, an organic oil, an alcohol or water.

The vinyl polymer having a carbosiloxane dendrimer structure in its side molecular chain, in this embodiment, is the same as that described above. The liquid may be a silicone oil, an organic oil, an alcohol or water. The silicone oil may be a dimethylpolysiloxane with the two molecular ends capped with trimethylsiloxy groups, a copolymer of methylphenylsiloxane and of dimethylsiloxane having the two molecular ends capped with trimethylsiloxy groups, a copolymer of methyl-3,3,3-trifluoropropylsiloxane and of dimethylsiloxane having the two molecular ends capped with trimethylsiloxy groups, or similar unreactive linear silicone oils, and also hexamethyl-cyclotrisiloxane, octamethylcyclotetrasiloxane, decamethylcyclopentasiloxane, dodecamethylcyclo-hexasiloxane or a similar cyclic compound. In addition to the unreactive silicone oils, modified polysiloxanes containing functional groups such as silanol groups, amino groups and polyether groups on the ends or within the side molecular chains may be used.

The organic oils may be liquid paraffin, isoparaffin, hexyl laurate, isopropyl myristate, myristyl myristate, cetyl myristate, 2-octyldodecyl myristate; isopropyl palmitate, 2-ethylhexyl palmitate, butyl stearate, decyl oleate, 2-octyldodecyl oleate, myristyl lactate, cetyl lactate, lanolin acetate, stearyl alcohol, cetostearyl alcohol, oleyl alcohol, avocado oil, almond oil, olive oil, cocoa oil, jojoba oil, gum oil, sunflower oil, soybean oil, camellia oil, squalane, castor oil, mink oil, cottonseed oil, coconut oil, egg yolk oil, beef tallow, lard, polypropylene glycol monooleate, neopentyl glycol 2-ethylhexanoate or a similar glycol ester oil; triglyceryl isostearate, the triglyceride of a fatty acid of coconut oil, or a similar oil of a polyhydric alcohol ester; polyoxyethylene lauryl ether, polyoxypropylene cetyl ether or a similar polyoxyalkylene ether.

The alcohol may be any type that is suitable for use in combination with a cosmetic product starting material. For example, it may be methanol, ethanol, butanol, isopropanol or similar lower alcohols. A solution or a dispersion of the alcohol should have a viscosity within the range from 10 to $10^9$ mPa at 25° C. To improve the sensory use properties in a cosmetic product, the viscosity should be within the range from 100 to $5 \times 10^8$ mPa·s.

The solutions and dispersions may be readily prepared by mixing the vinyl polymer having a carbosiloxane dendrimer structure with a silicone oil, an organic oil, an alcohol or water. The liquids may be present in the step of polymerization of the polymer of vinyl type having a carbosiloxane dendrimer structure. In this case, the unreacted residual vinyl monomer should be completely removed by heat treatment of the solution or dispersion under atmospheric pressure or reduced pressure. In the case of a dispersion, the dispersity of the polymer of vinyl type may be improved by adding a surfactant. Such an agent may be hexyl-benzenesulfonic acid, octylbenzenesulfonic acid, decylbenzenesulfonic acid, dodecylbenzenesulfonic acid, cetylbenzenesulfonic acid, myristylbenzenesulfonic acid or anionic surfactants of the sodium salts of these acids; octyltrimethylammonium hydroxide, dodecyltrimethylammonium hydroxide, hexadecyltrimethylammonium hydroxide, octyldimethylbenzylammonium hydroxide, decyldimethylbenzylammonium hydroxide, dioctadecyldimethylammonium hydroxide, beef tallow-trimethylammonium hydroxide, coconut oil-trimethylammonium hydroxide, or a similar cationic surfactant; a polyoxyalkylene alkyl ether, a polyoxyalkylenealkylphenol, a polyoxyalkylene alkyl ester, the sorbitol ester of polyoxyalkylene, polyethylene glycol, polypropylene glycol, an ethylene oxide additive of diethylene glycol trimethylnonanol, and nonionic surfactants of polyester type, and also mixtures. In addition, the solvents and dispersions may be combined with iron oxide suitable for use with cosmetic products, or a similar pigment, and also zinc oxide, titanium oxide, silicon oxide, mica, talc or similar mineral oxides in powder form. In the dispersion, a mean particle diameter of the polymer of vinyl type may be within a range of between 0.001 and 100 microns and preferably between 0.01 and 50 microns. The reason for this is that, outside the recommended range, a cosmetic product mixed with the emulsion will not have a nice enough feel on the skin or to the touch, or sufficient spreading properties or a pleasant feel.

The vinyl polymer contained in the dispersion or the solution may have a concentration in the range between 0.1% and 95% by weight and preferably between 5% and 85% by weight. However, to facilitate the handling and the preparation of the mixture, the range should preferably be between 10% and 75% by weight.

The vinyl polymer may be one of the polymers described in the examples of patent application EP 0 963 751 or, for example, the product TIB-4-200 sold by Dow Corning.

According to one embodiment, the vinyl polymer also comprises at least one organofluorine group.

Structures in which the polymerized vinyl units constitute the backbone and carbosiloxane dendritic structures and also organofluorine groups are attached to side chains are particularly preferred.

The organofluorine groups may be obtained by replacing with fluorine atoms all or some of the hydrogen atoms of methyl, ethyl, propyl, isopropyl, butyl, isobutyl, tert-butyl, pentyl, neopentyl, hexyl, cyclohexyl, heptyl, octyl, nonyl, decyl, undecyl, dodecyl, tridecyl, tetradecyl, hexadecyl and octadecyl groups and other alkyl groups of 1 to 20 carbon atoms, and also alkyloxyalkylene groups of 6 to 22 carbon atoms.

The groups represented by the formula: —$(CH_2)_x$—$(CF_2)_y$—$R^{13}$ are suggested as examples of fluoroalkyl groups obtained by substituting fluorine atoms for hydrogen atoms of alkyl groups. In the formula, the index "x" is 0, 1, 2 or 3 and "y" is an integer from 1 to 20. $R^{13}$ is an atom or a group chosen from a hydrogen atom, a fluorine atom, —$CH(CF_3)_2$— and $CF(CF_3)_2$. Such fluorine-substituted alkyl groups are exemplified by linear or branched polyfluoroalkyl or perfluoroalkyl groups represented by the formulae presented below.

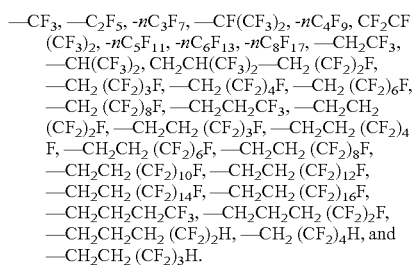

The groups represented by —$CH_2CH_2$—$(CF_2)_m$—$CFR^{14}$-$[OCF_2CF(CF_3)]_n$—$OC_3F_7$ are suggested as fluoroalkyloxyfluoroalkylene groups obtained by substituting fluorine atoms for hydrogen atoms of alkyloxyalkylene groups. In the formula, the index "m" is 0 or 1, "n" is 0, 1, 2, 3, 4 or 5, and $R^{14}$ is a fluorine atom $CF_3$. Such fluoroalkyloxyfluoroalkylene groups are exemplified by the perfluoroalkyloxy-fluoroalkylene groups represented by the formulae presented below:

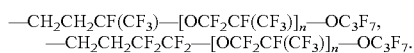

The number-average molecular weight of the vinyl polymer used in the present invention may be between 3000 and 2 000 000 and more preferably between 5000 and 800 000.

This type of fluorinated vinyl polymer may be obtained by addition of
- a vinyl monomer (B) not containing any organofluorine groups in the molecule
- to a vinyl monomer containing organofluorine groups in the molecule (A), and
- a carbosiloxane dendrimer (C) containing radical-polymerizable organic groups represented by the general formula (III):

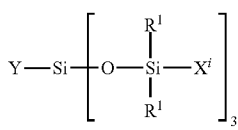

in which Y is a radical-polymerizable organic group and $R^1$ and $X^i$ are as above, and by subjecting them to a copolymerization.

The vinyl monomers (A) containing organofluorine groups in the molecule are preferably monomers represented by the general formula: $-(CH_2)=CR^{15}COOR^f$. In the formula, $R^{15}$ is a hydrogen atom or a methyl group and $R^f$ is an organofluorine group exemplified by the fluoroalkyl and fluoroalkyloxyfluoroalkylene groups described above. The compounds represented by the formulae presented below are suggested as specific examples of the component (A). In the formulae presented below "z" is an integer from 1 to 4.

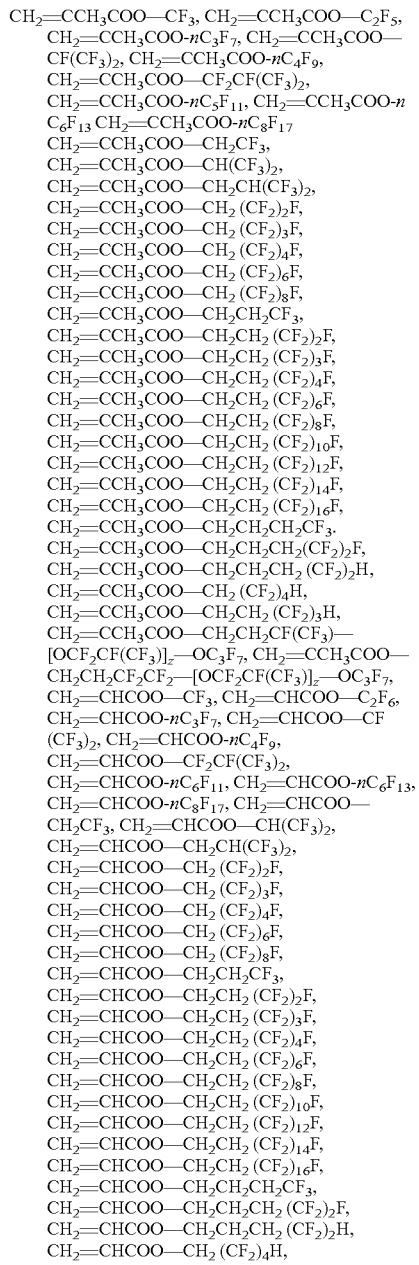

Among these, the vinyl polymers represented by the formulae presented below are preferable:

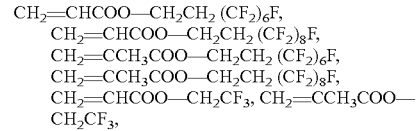

The vinyl polymers represented by the formulae presented below are particularly preferable.

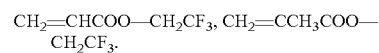

The vinyl monomers (B) not containing any organofluorine groups in the molecule may be any monomer containing radical-polymerizable vinyl groups illustrated, for example, by methyl acrylate, methyl methacrylate, ethyl acrylate, ethyl methacrylate, n-propyl acrylate, n-propyl methacrylate, isopropyl acrylate, isopropyl methacrylate, and other lower alkyl acrylates or methacrylates; glycidyl acrylate, glycidyl methacrylate; n-butyl acrylate, n-butyl methacrylate, isobutyl acrylate, isobutyl methacrylate, tert-butyl acrylate, tert-butyl methacrylate, n-hexyl acrylate, n-hexyl methacrylate, n-hexyl acrylate, n-hexyl methacrylate, cyclohexyl acrylate, cyclohexyl methacrylate, 2-ethylhexyl acrylate, 2-ethylhexyl methacrylate, octyl acrylate, octyl methacrylate, lauryl acrylate, lauryl methacrylate, stearyl acrylate, stearyl methacrylate, and other higher acrylates and methacrylates; vinyl acetate, vinyl propionate and other lower fatty acid vinyl esters; vinyl butyrate, vinyl caproate, vinyl 2-ethylhexanoate, vinyl laurate, vinyl stearate, and other higher fatty acid esters; styrene, vinyltoluene, benzyl acrylate, benzyl methacrylate, phenoxyethyl acrylate, phenoxyethyl methacrylate, vinylpyrrolidone, and other vinylaromatic monomers; dimethylaminoethyl acrylate, dimethylamino-ethyl methacrylate, diethylaminoethyl acrylate, diethylaminoethyl methacrylate, and other aminovinyl monomers, acrylamide, methacrylamide, N-methylolacryl-amide, N-methylolmethacrylamide, N-methoxymethylacryl-amide, N-methoxymethylmethacrylamide, isobutoxymethoxy-acrylamide, isobutoxymethoxymethacrylamide, N,N-dimethylacrylamide, N,N-dimethylmethacrylamide, and other vinylamide monomers; hydroxyethyl acrylate, hydroxyethyl methacrylate, acrylic acid hydroxypropyl alcohol, methacrylic acid hydroxypropyl alcohol, and other hydroxyvinyl monomers; acrylic acid, methacrylic acid, itaconic acid, crotonic acid, fumaric acid, maleic acid, and other vinylcarboxylic acid monomers; tetrahydrofurfuryl acrylate, tetrahydrofurfuryl methacrylate, butoxyethyl acrylate, butoxyethyl methacrylate, ethoxydiethylene glycol acrylate, ethoxy-diethylene glycol methacrylate, polyethylene glycol acrylate, polyethylene glycol methacrylate, polypropylene glycol monoacrylate, polypropylene glycol monomethacrylate, hydroxybutyl vinyl ether, cetyl vinyl ether, 2-ethylhexyl vinyl ether, and other vinyl monomers containing an ether bond; acryloxypropyl-trimethoxysilane, methacryloxypropyltrimethoxysilane, polydimethylsiloxanes containing acryl or methacryl groups at one of the ends, polydimethylsiloxanes containing alkenylaryl groups at one of the ends and other silicone compounds containing unsaturated groups; butadiene; vinyl chloride; vinylidene chloride; acrylonitrile, methacrylonitrile; dibutyl fumarate; maleic anhydride; dodecylsuccinic anhydride; acryl glycidyl ether, methacryl glycidyl ether, 3,4-epoxy-cyclohexylmethyl acrylate, 3,4-epoxycyclohexylmethyl methacrylate, alkali metal salts, ammonium salts and organic amine salts of acrylic acid, of methacrylic acid, of itaconic acid, of crotonic acid, of fumaric acid, of maleic acid and of other radical-polymerizable unsaturated carboxylic acids, radical-polymerizable unsaturated monomers containing sulfonic acid groups, such as styrene sulfonic acid and also the alkali metal salts thereof, the ammonium salts thereof and the organic amine salts thereof; the quaternary ammonium salts derived from acrylic acid or methacrylic acid, such as 2-hydroxy-3-methacryloxypropyltrimethylammonium chloride, methacrylic acid esters of a tertiary amine alcohol, such as the diethylamine ester of methacrylic acid and quaternary ammonium salts thereof.

In addition, it is also possible to use as vinyl monomers (B) the polyfunctional vinyl monomers illustrated, for example, by trimethylolpropane triacrylate, trimethylolpropane trimethacrylate, pentaerythrityl triacrylate, pentaerythrityl trimethacrylate, ethylene glycol diacrylate, ethylene glycol dimethacrylate, tetraethylene glycol diacrylate, tetraethylene glycol dimethacrylate, polyethylene glycol diacrylate, polyethylene glycol dimethacrylate, 1,4-butanediol diacrylate, 1,4-butanediol dimethacrylate, 1,6-hexanediol diacrylate, 1,6-hexane-diol dimethacrylate, neopentyl glycol diacrylate, neopentyl glycol dimethacrylate, trimethylolpropane-trioxyethyl acrylate, trimethylolpropanetrioxyethyl methacrylate, tris(2-hydroxyethyl)isocyanurate diacrylate, tris(2-hydroxyethyl)isocyanurate dimethacrylate, tris(2-hydroxyethyl)isocyanurate triacrylate, tris(2-hydroxyethyl)isocyanurate trimethacrylate, polydimethylsiloxane in which the two ends of the molecular chain are blocked with alkenylaryl groups, and other silicone compounds containing unsaturated groups.

As regards the ratio mentioned above in which the component (A) and the component (B) are copolymerized, the weight ratio of compound (A) to compound (B) should be within the range from 0.1:99.9 to 100:0 and preferably within the range 1:99 to 100:0.

The carbosiloxane dendrimer (C) is represented by the general formula (III) indicated above. In formula (III), Y is a radical-polymerizable organic group, the type of which is not subject to any special limitations provided that it is an organic group capable of undergoing a radical addition reaction. Organic groups containing acryl and methacryl, organic groups containing alkenylaryl, or alkenyl groups of 2 to 10 carbon atoms represented by the general formulae presented below are suggested as specific examples.

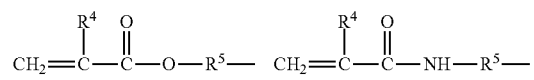

In the formulae, $R^4$ and $R^6$ are hydrogen atoms or methyl groups, $R^5$ and $R^8$ are alkylene groups of 1 to 10 carbon atoms, and $R^7$ is an alkyl group of 1 to 10 carbon atoms. The index "b" is an integer from 0 to 4 and "c" is 0 or 1. Acryloxymethyl, 3-acryloxypropyl, methacryloxymethyl, 3-methacryloxypropyl, 4-vinylphenyl, 3-vinylphenyl, 4-(2-propenyl)phenyl, 3-(2-propenyl)phenyl, 2-(4-vinylphenyl) ethyl, 2-(3-vinylphenyl)enyl, vinyl, allyl, methallyl, and 5-hexenyl are suggested as examples of such radical-polymerizable organic groups. The index "i" in formula (II), which is an integer from 1 to 10, is the number of generations of the said silylalkyl group, in other words the number of times that the silylalkyl group is repeated. Thus, the carbosiloxane dendrimer of this component with a generation number of 1 is represented by the general formula:

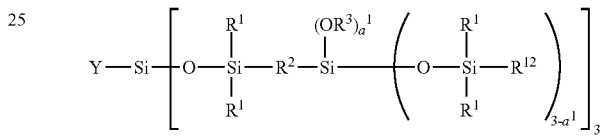

(in which Y, $R^1$, $R^2$ and $R^3$ are as above and $R^{12}$ is a hydrogen atom or such as $R^1$ described above. The index "$a^1$" is an integer from 0 to 3, the total mean of "$a^1$" per molecule being from 0 to 7). The carbosiloxane dendrimers of this component with a generation number of 2 are represented by the general formula:

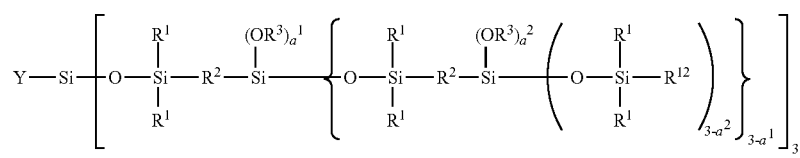

(in which Y, $R^1$, $R^2$, $R^3$ and $R^{12}$ are as above and the indices "$a^1$" and "$a^2$" are integers from 0 to 3, the total mean of "$a^1$" and of "$a^2$" per molecule being from 0 to 25).

The carbosiloxane dendrimers of this component with a generation number of 3 are represented by the general formula:

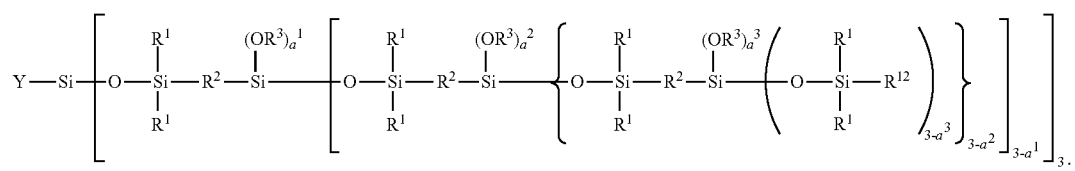

(in which Y, $R^1$, $R^2$, $R^3$ and $R^{12}$ are as above and the indices "$a^1$" and "$a^2$" and "$a^3$" are integers from 0 to 3, the total mean of "$a^1$", "$a^2$" and "$a^3$" per molecule being from 0 to 79).

The component (C) is illustrated by carbosiloxane dendrimers represented by formulae of mean composition represented below.
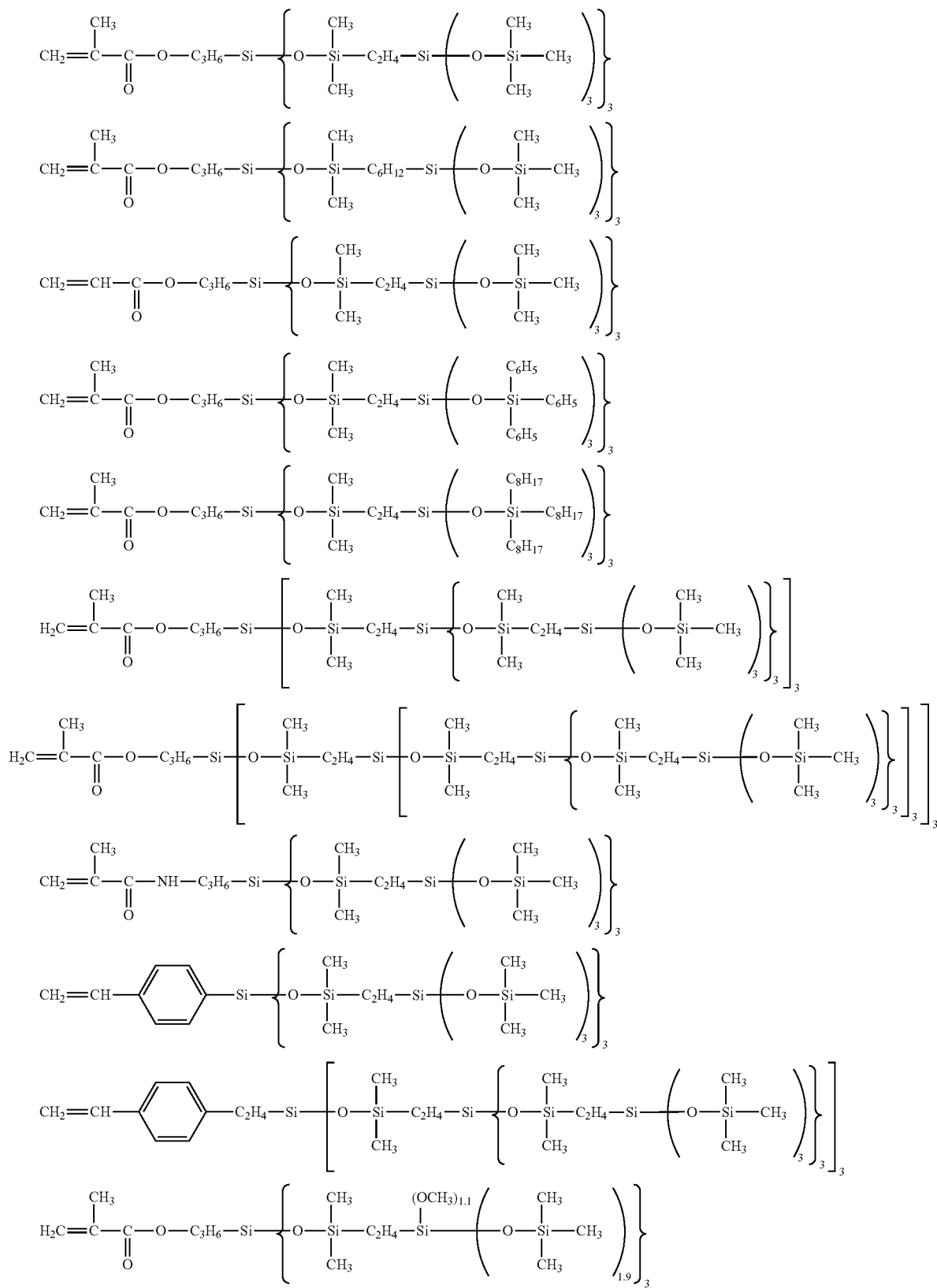

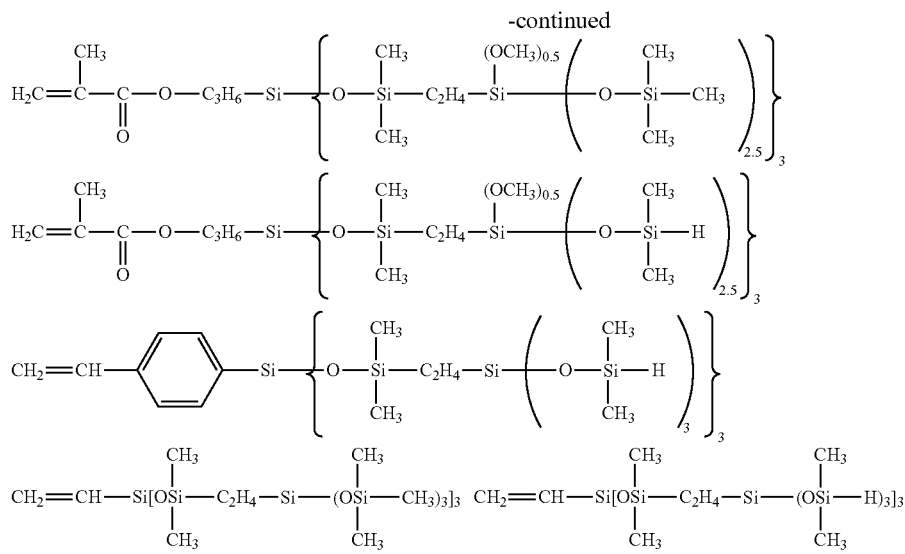

The carbosiloxane dendrimers of the component (C) may be prepared using the process for preparing siloxane/silylalkylene branched copolymers described in document EP 1 055 674. For example, they may be prepared by subjecting organic alkenyl silicones and silicone compounds comprising hydrogen atoms linked to silicon, represented by the general formula:

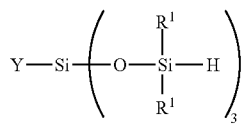

(in which $R^1$ and Y are as above) to a hydrosilylation reaction. For example, 3-methacryloxypropyltris(dimethylsiloxy)silane, 3-acryloxypropyltris(dimethylsiloxy)silane and 4-vinylphenyltris(dimethylsiloxy)silane are used as silicon compounds represented by the above formula. Vinyltris (trimethylsiloxy)silane, vinyltris(dimethyl-phenylsiloxy)silane and 5-hexenyltris(trimethylsiloxy)-silane are used as organosilicon alkenyl compounds. In addition, it is preferable to perform the hydrosilylation reaction in the presence of a transition metal catalyst such as chloroplatinic acid and the platinum/vinylsiloxane complex.

The copolymerization ratio of the component (C), in terms of its weight ratio relative to the total weight of compound (A) and (B) should be within the range from 0.1:99.9 to 99.9:0.1, preferably within the range from 1:99 to 99:1 and even more preferably within the range from 5:95 to 95:5.

Amino groups may be introduced into the side chains of the vinyl polymer using, included in the component (B), vinyl monomers containing amino groups, such as dimethylaminoethyl acrylate, dimethylaminoethyl methacrylate, diethylaminoethyl acrylate and diethyl-aminoethyl methacrylate, followed by performing a modification with potassium acetate monochloride, ammonium acetate monochloride, the aminomethylpropanol salt of monochloroacetic acid, the triethanolamine salt of monobromoacetic acid, sodium monochloropropionate, and other alkali metal salts of halogenated fatty acids; otherwise, carboxylic acid groups may be introduced into the side chains of the vinyl polymer using, included in the component (B), vinyl monomers containing carboxylic acids, such as acrylic acid, methacrylic acid, itaconic acid, crotonic acid, fumaric acid and maleic acid, and the like, followed by neutralizing the product with triethylamine, diethylamine, triethanolamine and other amines.

The fluorinated vinyl polymer may be one of the polymers described in the examples of patent application WO 03/045 337 or, for example, the product TIB-4-100 sold by Dow Corning.

The vinyl polymer may be present in a content ranging from 0.1% to 70% by weight, relative to the total weight of the composition, preferably ranging from 0.5% to 50% by weight, preferentially ranging from 1% to 40% by weight and more preferably ranging from 5% to 15% by weight.

The vinyl polymer may be present in the composition in a proportion of at least 3% by weight in the composition, preferably between 5% and 25% by weight, more preferably between 5% and 15% by weight and especially about 10% by weight.

3. Dispersion of Acrylic or Vinyl Radical Homopolymer or Copolymer Particles Dispersed in the Said Liquid Fatty Phase According to a third embodiment of the invention, the film-forming polymer present in the composition according to the invention is a dispersion of acrylic or vinyl radical homopolymer or copolymer particles dispersed in the liquid fatty phase of the composition.

According to the invention, the polymer in the form of particles dispersed in the volatile liquid fatty phase is a solid that is insoluble in the liquid fatty phase of the composition even at its softening point, unlike a wax even of polymeric origin, which is itself soluble in the liquid organic phase (or fatty phase) at its melting point.

The composition according to the invention advantageously comprises at least one stable dispersion of generally spherical polymer particles of one or more polymers, in a volatile liquid fatty phase. These dispersions may especially be in the form of polymer nanoparticles in stable dispersion in the said liquid organic phase. The nanoparticles preferably have a mean size of between 5 and 800 nm and better still between and 500 nm. However, it is possible to obtain polymer particles ranging up to 1 μm in size.

Preferably, the polymer particles in dispersion are insoluble in water-soluble alcohols, for instance ethanol.

The polymers in dispersion that may be used in the composition of the invention preferably have a molecular weight of about from 2000 to 10 000 000 g/mol and a Tg of from −100° C. to 300° C., better still from −50° C. to 100° C. and preferably from −10° C. to 50° C.

It is possible to use film-forming polymers preferably having a low Tg, of less than or equal to skin temperature and especially less than or equal to 40° C.

Preferably, the polymer used is film-forming, i.e. it is capable of forming an isolable film, by itself or in combination with a plasticizer. It is, however, possible to use a non-film-forming polymer.

The term "non-film-forming polymer" means a polymer that is incapable of forming an isolable film by itself. This polymer can, in combination with a non-volatile compound of the oil type, form a continuous, uniform deposit on the skin and/or the lips.

Among the film-forming polymers that may be mentioned are acrylic or vinyl radical homopolymers or copolymers, preferably with a Tg of less than or equal to 40° C. and especially ranging from −10° C. to 30° C., used alone or as a mixture.

Among the non-film-forming polymers that may be mentioned are optionally crosslinked vinyl or acrylic radical homopolymers or copolymers preferably with a Tg of greater than 40° C. and especially ranging from 45° C. to 150° C., used alone or as a mixture.

The term "radical polymer" means a polymer obtained by polymerization of unsaturated and especially ethylenic monomers, each monomer being capable of homopolymerizing (unlike polycondensates). The radical polymers may especially be vinyl polymers or copolymers, especially acrylic polymers.

The acrylic polymers may result from the polymerization of ethylenically unsaturated monomers containing at least one acid group and/or esters of these acid monomers and/or amides of these acids.

Monomers bearing an acid group that may be used include α,β-ethylenic unsaturated carboxylic acids such as acrylic acid, (meth)acrylic acid, crotonic acid, maleic acid or itaconic acid. (Meth)acrylic acid and crotonic acid are preferably used, and more preferably (meth)acrylic acid.

The acid monomer esters are advantageously chosen from (meth)acrylic acid esters (also known as (meth)acrylates), for instance alkyl (meth)acrylates, in particular of a $C_1$-$C_{20}$ and preferably $C_1$-$C_8$ alkyl, aryl (meth)acrylates, in particular of a $C_6$-$C_{10}$ aryl, and hydroxyalkyl (meth)acrylates, in particular of a $C_2$-$C_6$ hydroxyalkyl. Alkyl (meth)acrylates that may be mentioned include methyl, ethyl, butyl, isobutyl, 2-ethylhexyl and lauryl (meth)acrylate. Hydroxyalkyl (meth)acrylates that may be mentioned include hydroxy-ethyl (meth)acrylate and 2-hydroxypropyl (meth)-acrylate. Aryl (meth) acrylates that may be mentioned include benzyl or phenyl acrylate.

The (meth)acrylic acid esters that are particularly preferred are the alkyl (meth)acrylates.

Radical polymers that are preferably used include copolymers of (meth)acrylic acid and of alkyl (meth)acrylate, especially of a $C_1$-$C_4$ alkyl. Methyl acrylates optionally copolymerized with acrylic acid may more preferentially be used.

Amides of the acid monomers that may be mentioned include (meth)acrylamides, especially N-alkyl(meth)-acrylamides, in particular of a $C_2$-$C_{12}$ alkyl, such as N-ethylacrylamide, N-t-butylacrylamide and N-octylacrylamide; N-di($C_1$-$C_4$)alkyl(meth)acrylamides.

The acrylic polymers may also result from the polymerization of ethylenically unsaturated monomers containing at least one amine group, in free form or in partially or totally neutralized form, or alternatively in partially or totally quaternized form. Such monomers may be, for example, dimethylaminoethyl (meth)acrylate, dimethylaminoethyl(meth)acrylamide, vinylamine, vinylpyridine or diallyldimethylammonium chloride.

The vinyl polymers may also result from the homopolymerization or copolymerization of at least one monomer chosen from vinyl esters and styrene monomers. In particular, these monomers may be polymerized with acid monomers and/or esters thereof and/or amides thereof, such as those mentioned previously. Examples of vinyl esters that may be mentioned include vinyl acetate, vinyl propionate, vinyl neodecanoate, vinyl pivalate, vinyl benzoate and vinyl t-butylbenzoate. Styrene monomers that may be mentioned include styrene and α-methylstyrene.

The list of monomers given is not limiting, and it is possible to use any monomer known to those skilled in the art included in the categories of acrylic and vinyl monomers (including monomers modified with a silicone chain).

As other vinyl monomers that may be used, mention may also be made of:

N-vinylpyrrolidone, N-vinylcaprolactam, vinyl-N—($C_1$-$C_6$)alkylpyrroles, vinyloxazoles, vinylthiazoles, vinylpyrimidines and vinylimidazoles, olefins such as ethylene, propylene, butylene, isoprene or butadiene.

The vinyl polymer may be crosslinked with one or more difunctional monomers especially comprising at least two ethylenic unsaturations, such as ethylene glycol di(meth) acrylate or diallyl phthalate.

The polymer(s) in dispersion in the organic liquid phase may represent, as solids, from 1% to 60%, preferably from 2% to 50% and better still from 5% to 40% of the weight of the composition.

It is preferably chosen to use a dispersion of film-forming polymer particles, the particles being dispersed in a volatile oil.

According to one embodiment, the composition contains a stabilizer that is solid at room temperature. The polymer particles are preferably surface-stabilized by means of a stabilizer that may be a block polymer, a grafted polymer and/or a random polymer, alone or as a mixture. The stabilization may take place by any known means, and in particular by direct addition of the block polymer, grafted polymer and/or random polymer during the polymerization.

The stabilizer is preferably also present in the mixture before polymerization of the polymer. However, it is also possible to add it continuously, especially when the monomers are also added continuously.

2-30% by weight and preferably 5-20% by weight of stabilizer may be used relative to the initial monomer mixture.

Among the grafted polymers that may be mentioned are silicone polymers grafted with a hydrocarbon-based chain; hydrocarbon-based polymers grafted with a silicone chain.

Thus, grafted-block or block copolymers comprising at least one block of polyorganosiloxane type and at least one block of a radical polymer, for instance grafted copolymers of acrylic/silicone type, may thus be used, which may be used especially when the non-aqueous medium is silicone-based.

It is also possible to use grafted-block or block copolymers comprising at least one block of polyorganosiloxane type and at least one block of a polyether. The polyorganosiloxane block may especially be a polydimethylsiloxane or a poly($C_2$-$C_{18}$)alkylmethyl-siloxane; the polyether block may be a poly ($C_2$-$C_{18}$)-alkylene, in particular polyoxyethylene and/or polyoxy-propylene. In particular, dimethicone copolyols or ($C_2$-$C_{18}$) alkyldimethicone copolyols such as those sold under the name Dow Corning 3225C by the company Dow Corning, and lauryl methicones such as those sold under the name Dow Corning Q2-5200 by the company Dow Corning, may be used.

Grafted-block or block copolymers that may also be mentioned include those comprising at least one block resulting from the polymerization of at least one ethylenic monomer containing one or more optionally conjugated ethylenic bonds, for instance ethylene or dienes such as butadiene and isoprene, and of at least one block of a vinyl polymer and better still a styrene polymer. When the ethylenic monomer comprises several optionally conjugated ethylenic bonds, the residual ethylenic unsaturations after the polymerization are generally hydrogenated. Thus, in a known manner, the polymerization of isoprene leads, after hydrogenation, to the formation of an ethylene-propylene block, and the polymerization of butadiene leads, after hydrogenation, to the formation of an ethylene-butylene block. Among these polymers that may be mentioned are block copolymers, especially of "diblock" or "triblock" type such as polystyrene/polyisoprene (SI), polystyrene/polybutadiene (SB) such as those sold under the name Luvitol HSB by BASF, of the type such as polystyrene/copoly(ethylene-propylene) (SEP) such as those sold under the name Kraton by Shell Chemical Co. or of the type such as polystyrene/copoly(ethylene-butylene) (SEB). Kraton G1650 (SEBS), Kraton G1651 (SEBS), Kraton G1652 (SEBS), Kraton G1657X (SEBS), Kraton G1701X (SEP), Kraton G1702X (SEP), Kraton G1726X (SEB), Kraton D-1101 (SBS), Kraton D-1102 (SBS) and Kraton D-1107 (SIS) may be used in particular. The polymers are generally known as hydrogenated or non-hydrogenated diene copolymers.

Gelled Permethyl 99A-750, 99A-753-59 and 99A-753- (mixture of triblock and of star polymer), Versagel 5960 from Penreco (triblock+star polymer); OS129880, OS129881 and OS84383 from Lubrizol (styrene/methacrylate copolymer) may also be used.

As grafted-block or block copolymers comprising at least one block resulting from the polymerization of at least one ethylenic monomer containing one or more ethylenic bonds and of at least one block of an acrylic polymer, mention may be made of poly(methyl methacrylate)/polyisobutylene diblock or triblock copolymers or grafted copolymers containing a poly(methyl methacrylate) skeleton and polyisobutylene grafts.

As grafted-block or block copolymers comprising at least one block resulting from the polymerization of at least one ethylenic monomer containing one or more ethylenic bonds and of at least one block of a polyether such as a $C_2$-$C_{18}$ polyalkylene (especially polyethylene and/or polyoxypropylene), mention may be made of polyoxyethylene/polybutadiene or polyoxyethylene/polyisobutylene diblock or triblock copolymers.

Copolymers based on alkyl acrylates or (meth)acrylates derived from $C_1$-$C_4$ alcohols and on alkyl acrylates or (meth)acrylates derived from $C_8$-$C_{30}$ alcohols may thus be used. Mention may be made in particular of stearyl (meth)acrylate/methyl methacrylate copolymer.

When the liquid synthesis solvent comprises at least one silicone oil, the stabilizer is preferably chosen from the group consisting of grafted-block or block copolymers comprising at least one block of polyorganosiloxane type and at least one block of a free-radical polymer or of a polyether or of a polyester, for instance polyoxypropylene and/or polyoxyethylene blocks.

When the liquid organic phase does not comprise any silicone oil, the stabilizer is preferably chosen from the group formed by:
(a) grafted-block or block copolymers comprising at least one block of polyorganosiloxane type and at least one block of a radical polymer or of a polyether or a polyester,
(b) copolymers of alkyl acrylates or methacrylates derived from $C_1$-$C_4$ alcohols and of alkyl acrylates or methacrylates derived from $C_8$-$C_{30}$ alcohols,
(c) grafted-block or block copolymers comprising at least one block resulting from the polymerization of at least one ethylenic monomer containing conjugated ethylenic bonds, and at least one block of a vinyl or acrylic polymer or of a polyether or of a polyester, or mixtures thereof.

Diblock polymers are preferably used as stabilizer.

When the polymer has a glass transition temperature that is too high for the intended application, a plasticizer may be combined therewith. The plasticizer may be chosen from the plasticizers usually used in the field of application and especially from compounds liable to be solvents for the polymer. Coalescers may also be used in order to aid the polymer to form a continuous and homogeneous deposit.

The coalescers or plasticizers that may be used in the invention are especially those mentioned in document FR-A-2 782 917.

The composition may contain a polymer plasticizer, so as to lower the Tg of the polymer film and to improve the adhesion of the polymer film to its support, in particular to keratin materials. The plasticizer especially lowers the glass transition temperature of the polymer by at least 2, 3 or 4° C. and preferably from 5° C. to 20° C. In one preferred embodiment, the plasticizer especially lowers the glass transition temperature of the polymer by at least 2, 3 or 4° C. and preferably from 5° C. to 20° C., when the plasticizer represents not more than 10% by weight of the polymer.

According to one embodiment, the compound may be chosen from esters of at least one carboxylic acid comprising 1 to 7 carbon atoms and of a polyol comprising at least four hydroxyl groups.

The polyol according to the invention may be a saccharide or a saccharide-based polyol, such as erythritol, xylitol or sorbitol. The polymer may be a monosaccharide or a polysaccharide comprising 1 to 10 saccharides, preferably from 1 to 4 and more preferably or 2 saccharides. The polyol may be chosen from erythritol, xylitol, sorbitol, glucose and sucrose.

The polyol according to the invention is preferably a disaccharide. Among the disaccharides that may be mentioned are sucrose (α-D-glucopyranosyl-(1-2)-β-D-fructofuranose), lactose (β-D-galactopyranosyl-(1-4)-β-D-glucopyranose) and maltose (α-D-glucopyranosyl-(1-4)-β-D-glucopyranose).

The plasticizer may be formed from a polyol substituted with at least two different monocarboxylic acids, or with at least three different monocarboxylic acids. The acid is preferably a monocarboxylic acid chosen in particular from acids comprising 1 to 7 carbon atoms and preferably 1 to 5 carbon atoms, for example acetic acid, n-propanoic acid, isopropanoic acid, n-butanoic acid, isobutanoic acid, tert-butanoic acid, n-pentanoic acid and benzoic acid.

According to one preferred embodiment, the ester is sucrose diacetate hexakis(2-methylpropanoate).

Synthesis Solvent for the Polymer Particles

The polymer dispersion may be manufactured as described in document EP-A-749 747.

A mixture comprising the initial monomers and also a radical initiator is prepared. This mixture is dissolved in a solvent referred to hereinbelow in the present description as the "synthesis solvent". When the fatty phase is a non-volatile oil, the polymerization may be performed in an apolar organic solvent (synthesis solvent), followed by adding the non-volatile oil (which should be miscible with the said synthesis solvent) and selectively distilling off the synthesis solvent.

A synthesis solvent which is such that the initial monomers and the radical initiator are soluble therein, and the polymer particles obtained are insoluble therein, so that they precipitate during their formation, is chosen. In particular, the synthesis solvent may be chosen from alkanes such as heptane, isododecane and cyclohexane.

When the chosen fatty phase is a volatile oil, the polymerization may be performed directly in the said oil, which thus also acts as synthesis solvent. The monomers should also be soluble therein, as should the radical initiator, and the polymer obtained should be insoluble therein.

The monomers are preferably present in the synthesis solvent, before polymerization, in a proportion of 5-20% by weight of the reaction mixture. The total amount of monomers may be present in the solvent before the start of the reaction, or part of the monomers may be added gradually as the polymerization reaction proceeds.

The radical initiator may especially be azobisisobutyronitrile or tert-butylperoxy-2-ethyl hexanoate.

The volatile phase of the composition may be formed from or comprise the synthesis solvent for the dispersed polymer particles.

Structuring Agent

The composition according to the invention may comprise as additional ingredient, combined with the said compound A described previously, at least one structuring agent chosen from semicrystalline polymers and thickeners comprising at least one group and preferably at least two groups capable of establishing hydrogen interactions, chosen from polymeric thickeners and organogelling agents. The presence of such a structuring agent may especially make it possible to improve the application qualities of the composition and the comfort of the deposit when it is applied to keratin materials.

Semicrystalline Polymer

According to a first embodiment, the structuring agent is a semicrystalline polymer.

The combination of a supramolecular compound as described previously with a semicrystalline polymer especially makes it possible, in particular in compositions for making up or caring for keratin materials, and particularly the skin or the lips, to obtain uniform mixing and a glossy, non-tacky deposit on the keratin materials.

Preferably, the total amount of semicrystalline polymer(s) represents from 0.1% to 50%, better still from 0.5% to 40% and even better still from 1% to 20% of the total weight of the composition.

For the purposes of the invention, the term "polymers" means compounds containing at least two repeating units, preferably at least three repeating units and more especially at least ten repeating units.

For the purposes of the invention, the term "semicrystalline polymers" means polymers comprising a crystallizable portion and an amorphous portion in the backbone and having a first-order reversible change of phase temperature, in particular of melting (solid-liquid transition). The crystallizable portion is either a side chain (or pendent chain) or a block in the backbone.

When the crystallizable portion of the semicrystalline polymer is a block of the polymer backbone, this crystallizable block has a different chemical nature from that of the amorphous blocks; in this case, the semicrystalline polymer is a block copolymer, for example of the diblock, triblock or multiblock type. When the crystallizable portion is a chain that is pendent on the backbone, the semicrystalline polymer may be a homopolymer or a copolymer.

The terms "organic compound" and "having an organic structure" mean compounds containing carbon atoms and hydrogen atoms and optionally heteroatoms such as S, O, N or P, alone or in combination.

The melting point of the semicrystalline polymer is preferably less than 150° C.

The melting point of the semicrystalline polymer is preferably greater than or equal to 30° C. and less than 100° C. More preferably, the melting point of the semicrystalline polymer is preferably greater than or equal to 30° C. and less than 60° C.

The semicrystalline polymer(s) according to the invention are solid at room temperature (25° C.) and atmospheric pressure (760 mmHg), with a melting point of greater than or equal to 30° C. The melting point values correspond to the melting point measured using a differential scanning calorimeter (DSC), such as the calorimeter sold under the name DSC 30 by the company Mettler, with a temperature rise of 5 or 10° C. per minute. (The melting point under consideration is the point corresponding to the temperature of the most endothermic peak of the thermogram).

The semicrystalline polymer(s) according to the invention preferably have a melting point that is higher than the temperature of the keratinous support intended to receive said composition, in particular the skin or the lips.

The semicrystalline polymer(s) according to the invention may be capable, alone or as a mixture, of structuring the composition without addition of a particular surfactant, or filler or wax.

According to the invention, the semicrystalline polymers are advantageously soluble in the fatty phase, especially to at least 1% by weight, at a temperature that is higher than their melting point. Besides the crystallizable chains or blocks, the blocks of the polymers are amorphous.

For the purposes of the invention, the expression "crystallizable chain or block" means a chain or block which, if it were obtained alone, would change from the amorphous state to the crystalline state reversibly, depending on whether one is above or below the melting point. For the purposes of the invention, a "chain" is a group of atoms, which are pendent or lateral relative to the polymer backbone. A "block" is a group of atoms belonging to the backbone, this group constituting one of the repeating units of the polymer.

Preferably, the polymer backbone of the semicrystalline polymers is soluble in the fatty phase.

Preferably, the crystallizable blocks or chains of the semicrystalline polymers represent at least 30% of the total weight of each polymer and better still at least 40%. The semicrystalline polymers containing crystallizable side chains are homopolymers or copolymers. The semicrystalline polymers of the invention containing crystallizable blocks are block or multiblock copolymers. They may be obtained by polymerizing a monomer containing reactive (or ethylenic) double bonds or by polycondensation. When the polymers of the invention are polymers containing crystallizable side chains, these side chains are advantageously in random or statistical form.

Preferably, the semicrystalline polymers of the invention are of synthetic origin. According to one preferred embodiment of the invention, the semicrystalline polymers of the invention do not comprise a polysaccharide backbone.

According to one preferred embodiment, the semicrystalline polymer is chosen from:

homopolymers and copolymers comprising units resulting from the polymerization of one or more monomers bearing crystallizable hydrophobic side chains, polymers bearing in the backbone at least one crystallizable block, polycondensates of aliphatic or aromatic or aliphatic/aromatic polyester type, ethylene and/or propylene homopolymers and/or copolymers prepared via metallocene catalysis.

The semicrystalline polymers that may be used in the invention may be chosen in particular from:

block copolymers of polyolefins of controlled crystallization, whose monomers are described in EP-A-0 951 897, polycondensates, especially of aliphatic or aromatic polyester type or of aliphatic/aromatic polyester type, ethylene and/or propylene homopolymers and/or copolymers prepared via metallocene catalysis, homopolymers or copolymers bearing at least one crystallizable side chain and homopolymers or copolymers bearing at least one crystallizable block in the backbone, for instance those described in document U.S. Pat. No. 5,156,911, homopolymers or copolymers bearing at least one crystallizable side chain, in particular bearing fluoro group(s), such as those described in document WO-A-01/19333, and mixtures thereof.

In the last two cases, the crystallizable side chain(s) or block(s) are hydrophobic.

A) Semi Crystalline Polymers Containing Crystallizable Side Chains

Mention may be made in particular of those defined in documents U.S. Pat. No. 5,156,911 and WO-A-01/19333.

They are homopolymers or copolymers comprising from 50% to 100% by weight of units resulting from the polymerization of one or more monomers bearing a crystallizable hydrophobic side chain.

These homopolymers or copolymers are of any nature, provided that they meet the conditions mentioned hereinbelow with, in particular, the characteristic of being soluble or dispersible in the fatty phase, by heating above their melting point mp. They can result:

from the polymerization, especially the free-radical polymerization, of one or more monomers containing reactive or ethylenic double bond(s) with respect to a polymerization, namely a vinyl, (meth)acrylic or allylic group, from the polycondensation of one or more monomers bearing co-reactive groups (carboxylic acid, sulfonic acid, alcohol, amine or isocyanate), for instance polyesters, polyurethanes, polyethers, polyureas or polyamides.

a) In general, the crystallizable units (chains or blocks) of the semicrystalline polymers according to the invention are derived from monomer(s) containing crystallizable block(s) or chain(s), used for manufacturing semicrystalline polymers. These polymers are chosen especially from homopolymers and copolymers resulting from the polymerization of at least one monomer containing crystallizable chain(s) that may be represented by formula X:

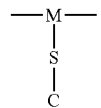

with M representing an atom of the polymer backbone,

S representing a spacer, and

C representing a crystallizable group.

The crystallizable chains "-S-C" may be aliphatic or aromatic, and optionally fluorinated or perfluorinated. "S" especially represents a group $(CH_2)_n$, $(CH_2CH_2O)_n$ or $(CH_2O)$, which may be linear or branched or cyclic, with n being an integer ranging from 0 to 22. Preferably, "S" is a linear group. Preferably, "S" and "C" are different.

When the crystallizable chains are hydrocarbon-based aliphatic chains, they comprise hydrocarbon-based alkyl chains containing at least 11 carbon atoms and not more than 40 carbon atoms and better still not more than 24 carbon atoms. They are especially aliphatic chains or alkyl chains containing at least 12 carbon atoms, and they are preferably $C_{14}$-$C_{24}$, preferably $C_{16}$-$C_{22}$ alkyl chains. When they are fluoroalkyl or perfluoroalkyl chains, they contain at least 11 carbon atoms, at least 6 of which carbon atoms are fluorinated.

As examples of semicrystalline homopolymers or copolymers containing crystallizable chain(s), mention may be made of those resulting from the polymerization of one or more of the following monomers: (meth)acrylates of saturated alkyls with the alkyl group being $C_{14}$-$C_{24}$, perfluoroalkyl (meth)acrylates with a $C_{11}$-$C_{15}$ perfluoroalkyl group, N-alkyl(meth)acrylamides with the alkyl group being $C_{14}$ to $C_{24}$ with or without a fluorine atom, vinyl esters containing alkyl or perfluoroalkyl chains with the alkyl group being $C_{14}$ to $C_{24}$ (with at least 6 fluorine atoms per perfluoroalkyl chain), vinyl ethers containing alkyl or perfluoroalkyl chains with the alkyl group being $C_{14}$ to $C_{24}$ and at least 6 fluorine atoms per perfluoroalkyl chain, $C_{14}$ to $C_{24}$ α-olefins such as, for example, octadecene, para-alkylstyrenes with an alkyl group containing from 12 to 24 carbon atoms, and mixtures thereof.

When the polymers result from a polycondensation, the hydrocarbon-based and/or fluorinated crystallizable chains as defined above are borne by a monomer that may be a diacid, a diol, a diamine or a diisocyanate.

When the polymers that are the subject of the invention are copolymers, they additionally contain from 0 to 50% of groups Y or Z resulting from the copolymerization:

α) of Y, which is a polar or non-polar monomer or a mixture of the two;

When Y is a polar monomer, it is either a monomer bearing polyoxyalkylenated groups (especially oxyethylenated and/or oxypropylenated groups), a hydroxyalkyl (meth)acrylate, for instance hydroxyethyl acrylate, (meth)acrylamide, an N-alkyl(meth)acrylamide, an N,N-dialkyl(meth)acrylamide such as, for example, N,N-diisopropylacrylamide or N-vinylpyrrolidone (NVP), N-vinylcaprolactam, a monomer bearing at least one carboxylic acid group, for instance (meth)acrylic acid, crotonic acid, itaconic acid, maleic acid or fumaric acid, or bearing a carboxylic acid anhydride group, for instance maleic anhydride, and mixtures thereof.

When Y is a non-polar monomer, it may be an ester of the linear, branched or cyclic alkyl (meth)acrylate type, a vinyl ester, an alkyl vinyl ether, an α-olefin, styrene or styrene substituted with a $C_1$ to $C_{10}$ alkyl group, for instance α-methylstyrene, or a macromonomer of the polyorganosiloxane type containing vinyl unsaturation.

For the purposes of the invention, the term "alkyl" means a saturated group especially of $C_8$ to $C_{24}$, except where otherwise mentioned.

β) of Z, which is a polar monomer or a mixture of polar monomers. In this case, Z has the same definition as the "polar Y" defined above.

Preferably, the semicrystalline polymers containing a crystallizable side chain are alkyl (meth)acrylate or alkyl(meth) acrylamide homopolymers with an alkyl group as defined above, and especially of $C_{14}$-$C_{24}$, copolymers of these monomers with a hydrophilic monomer preferably of different nature from (meth)acrylic acid, for instance N-vinylpyrrolidone or hydroxyethyl (meth)acrylate, and mixtures thereof.

Advantageously, the semicrystalline polymer(s) containing a crystallizable side chain has (have) a weight-average molecular mass Mp ranging from 5000 to 1 000 000, preferably from 10 000 to 800 000, preferentially from 15 000 to 500 000 and more preferably from 100 000 to 200 000.

As a particular example of a semicrystalline polymer that may be used in the composition according to the invention, mention may be made of the Intelimer® products from the company Landec described in the brochure "Intelimer® polymers", Landec IP22 (Rev. 4-97). These polymers are in solid form at room temperature (25° C.). They bear crystallizable side chains and have the preceding formula X.

For example, the product Intelimer® IPA 13-1 from the company Landec is chosen, which is a polystearyl acrylate with a molecular weight of about 145 000 and a melting point of 49° C.

The semicrystalline polymers may especially be those described in Examples 3, 4, 5, 7 and 9 of U.S. Pat. No. 5,156,911, containing a —COOH group, resulting from the copolymerization of acrylic acid and of a $C_5$ to $C_{16}$ alkyl (meth)acrylate with a melting point ranging from 20° C. to 35° C., and more particularly from the copolymerization:

of acrylic acid, of hexadecyl acrylate and of isodecyl acrylate in a 1/16/3 ratio, of acrylic acid and of pentadecyl acrylate in a 1/19 ratio, of acrylic acid, of hexadecyl acrylate and of ethyl acrylate in a 2.5/76.5/20 ratio, of acrylic acid, of hexadecyl acrylate and of methyl acrylate in a 5/85/10 ratio, of acrylic acid and of polyoctadecyl (meth)acrylate in a 2.5/97.5 ratio.

It is also possible to use the polymer Structure "O" from National Starch, such as the product described in document U.S. Pat. No. 5,736,125 with a melting point of 44° C.

The semicrystalline polymers may in particular be semicrystalline polymers with crystallizable pendent chains comprising fluoro groups, as described in Examples 1, 4, 6, 7 and 8 of document WO-A-01/19333.

It is also possible to use the semicrystalline polymers obtained by copolymerization of stearyl acrylate and of acrylic acid or of NVP, as described in document U.S. Pat. No. 5,519,063 or EP-A-550 745.

It is also possible to use the semicrystalline polymers obtained by copolymerization of behenyl acrylate and of acrylic acid or of NVP, as described in documents U.S. Pat. No. 5,519,063 and EP-A-550 745 and more especially those described in Examples 3 and 4 below, of polymer preparation.

B) Polymers Bearing at Least One Crystallizable Block in the Backbone

This is also a case of polymers that are soluble or dispersible in the fatty phase by heating above their melting point mp. These polymers are especially block copolymers consisting of at least two blocks of different chemical nature, one of which is crystallizable.

The polymer bearing at least one crystallizable block in the backbone may be chosen from block copolymers of olefin or of cycloolefin containing a crystallizable chain, for instance those derived from the block polymerization of:

cyclobutene, cyclohexene, cyclooctene, norbornene (i.e. bicyclo(2.2.1)-2-heptene), 5-methylnorbornene, 5-ethylnorbornene, 5,6-dimethylnorbornene, 5,5,6-trimethylnorbornene, 5-ethylidenenorbornene, 5-phenylnorbornene, 5-benzylnorbornene, 5-vinylnorbornene, 1,4,5,8-dimethano-1,2,3,4,4a,5,8a-octahydronaphthalene, dicyclopentadiene, or mixtures thereof, with ethylene, propylene, 1-butene, 3-methyl-1-butene, 1-hexene, 4-methyl-1-pentene, 1-octene, 1-decene or 1-eicosene, or mixtures thereof, and in particular copoly(ethylene/norbornene) blocks and (ethylene/propylene/ethylidene-norbornene) block terpolymers. Those resulting from the block copolymerization of at least two $C_2$-$C_{16}$, better still $C_2$-$C_{12}$ α-olefins such as those mentioned above and in particular block bipolymers of ethylene and of 1-octene may also be used.

The polymer bearing at least one crystallizable block in the backbone may be chosen from copolymers containing at least one crystallizable block, the rest of the copolymer being amorphous (at room temperature). These copolymers may also contain two crystallizable blocks of different chemical nature.

The preferred copolymers are those that simultaneously contain at room temperature a crystallizable block and an amorphous block that are both hydrophobic and lipophilic, sequentially distributed; mention may be made, for example, of polymers containing one of the crystallizable blocks and one of the amorphous blocks below:

Block that is crystallizable by nature, of polyester type, for instance poly(alkylene terephthalate), or of polyolefin type, for instance polyethylenes or polypropylenes.

Amorphous and lipophilic block, for instance: amorphous polyolefins or copoly(olefin)s such as poly(isobutylene), hydrogenated polybutadiene or hydrogenated poly(isoprene).

As examples of such copolymers containing a crystallizable block and an amorphous block, mention may be made of:

α) poly(ε-caprolactone)-b-poly(butadiene) block copolymers, preferably used hydrogenated, such as those described in the article D6 "Melting behavior of poly(-caprolactone)-block-polybutadiene copolymers" from S, Nojima, Macromolecules, 32, 3727-3734 (1999), β) the hydrogenated block or multiblock poly(butylene terephthalate)-b-poly(isoprene) block copolymers cited in the article D7 "Study of morphological and mechanical properties of PP/PBT" by B. Boutevin et al., Polymer Bulletin, 34, 117-123 (1995), γ) the poly(ethylene)-b-copoly(ethylene/propylene) block copolymers cited in the articles D8 "Morphology of semicrystalline block copolymers of ethylene-(ethylene-alt-propylene)" by P. Rangarajan et al., Macromolecules, 26, 4640-4645 (1993) and D9 "Polymer aggregates with crystalline cores: the system poly(ethylene)-poly(ethylene-propylene)" by P. Richter et al., Macromolecules, 30, 1053-1068 (1997), δ) the poly(ethylene)-b-poly(ethylethylene) block copolymers cited in the general article D10 "Crystallization in block copolymers" by I. W. Hamley, Advances in Polymer Science, Vol. 148, 113-137 (1999).

C) Polycondensates of Aliphatic or Aromatic or Aliphatic/Aromatic Polyester Type The polyester polycondensates may be chosen from aliphatic polyesters. Their molar mass is preferably greater than or equal to 200 and less than or equal to 10 000, and more preferably greater than or equal to 300 and less than or equal to 5000, preferably greater than or equal to 500 and greater than or equal to 2000 g/mol.

The polyester polycondensates are in particular chosen from polycaprolactones. In particular, the polycaprolactones may be chosen from ε-caprolactone homopolymers. The homopolymerization may be initiated with a diol, especially a diol containing from 2 to 10 atoms, such as diethylene glycol, 1,4-butanediol or neopentyl glycol.

Polycaprolactones may be used for example, especially those sold under the name CAPA® 240 (melting point of 68° C. and molecular weight of 4000), 223 (melting point of 48° C. and molecular weight of 2000), 222 (melting point of 48° C. and molecular weight of 2000), 217 (melting point of 44° C. and molecular weight of 1250), 2125 (melting point of 45° C. and molecular weight of 1250), 212 (melting point of 45° C. and molecular weight of 1000), 210 (melting point of 38° C. and molecular weight of 1000), 205 (melting point of 39° C. and molecular weight of 830) by the company Solvay, or PCL-300 and PCL-700 by the company Union Carbide.

CAPA® 2125 whose melting point is between 35 and 45° C. and whose molecular weight is equal to 1250 may be used in particular.

The semicrystalline polymers in the composition of the invention may or may not be partially crosslinked, provided that the degree of crosslinking does not interfere with their dissolution or dispersion in the fatty phase by heating above their melting point. It may then be a chemical crosslinking, by reaction with a multifunctional monomer during the polymerization. It may also be a physical crosslinking which may, in this case, be due either to the establishment of bonds of hydrogen or dipolar type between groups borne by the polymer, such as, for example, the dipolar interactions between carboxylate ionomers, these interactions being of small amount and borne by the polymer backbone; or to a phase separation between the crystallizable blocks and the amorphous blocks borne by the polymer.

Preferably, the semicrystalline polymers in the composition according to the invention are non-crosslinked.

D) Ethylene and/or Propylene Homopolymers and/or Copolymers Prepared Via Metallocene Catalysis The semicrystalline polymer of the composition of the invention may also be a waxy polymer obtained via metallocene catalysis, such as those described in patent US 2007/0 031 361, the content of which is incorporated herein by reference.

These polymers are ethylene and/or propylene homopolymers or copolymers prepared via metallocene catalysis, i.e. by polymerization at low pressure and in the presence of a metallocene catalyst.

The weight-average molecular mass (Mw) of the waxes obtained via metallocene catalysis described in this document is less than or equal to 25 000 g/mol and ranges, for example, from 2000 to 22 000 g/mol and better still from 4000 to 20 000 g/mol.

The number-average molecular mass (Mn) of the waxes obtained via metallocene catalysis described in this document is preferably less than or equal to 15 000 g/mol and ranges, for example, from 1000 to 12 000 g/mol and better still from 2000 to 10 000 g/mol.

The polydispersity index I of the polymer is equal to the ratio of the weight-average molecular mass Mw to the number-average molecular mass Mn.

Preferably, the polydispersity index of the waxy polymers is between 1.5 and 10, preferably between 1.5 and 5, preferably between 1.5 and 3 and better still between 2 and 2.5.

The waxy homopolymers and copolymers may be obtained in a known manner from ethylene and/or propylene monomers, for example via metallocene catalysis according to the process described in document EP 571 882, the content of which is incorporated herein by reference.

The ethylene and/or propylene homopolymers and copolymers prepared via metallocene catalysis may be unmodified or "polar"-modified (i.e. modified such that they contain polar groups). The polar-modified waxy homopolymers and copolymers may be prepared in a known manner from unmodified waxy homopolymers and copolymers such as those described previously by oxidation with gases containing oxygen, such as air, or by grafting with polar monomers such as maleic acid or acrylic acid or alternatively derivatives of these acids. These two routes enabling polar modification of the polyolefins obtained via metallocene catalysis are described, respectively, in documents EP 890 583 and U.S. Pat. No. 5,998,547, for example, the content of these two documents being incorporated herein by reference.

According to the present invention, the polar-modified ethylene and/or propylene homopolymers and copolymers prepared via metallocene catalysis that are particularly preferred are polymers modified such that they have hydrophilic properties. Examples that may be mentioned include ethylene and/or propylene homopolymers or copolymers modified by the presence of hydrophilic groups such as maleic anhydride, acrylate, methacrylate, polyvinylpyrrolidone (PVP), etc.

Waxy ethylene and/or propylene homopolymers or copolymers modified by the presence of hydrophilic groups such as maleic anhydride or acrylate are particularly preferred.

Examples that may be mentioned include:
polypropylene waxes modified with maleic anhydride (PPMA) sold by the company Clariant, or polypropylene-ethylene-maleic anhydride copolymers, such as those sold by the company Clariant under the name LicoCare, for instance LicoCare PP207 LP3349, LicoCare CM401 LP3345, LicoCare CA301 LP3346 and LicoCare CA302 LP3347, or
the unmodified polyethylene waxes sold by the company Clariant, such as the product LicoCare PE 102 LP3329.

In the context of a composition for the lips, a polar-modified waxy polymer with a low degree of crystallinity, preferably of less than 40%, will be preferred.

The use of these waxy polymers makes it possible especially to limit the loss of gloss of lipstick compositions.

Preferably, the total amount of modified or unmodified waxy polymers represents from 0.1% to 30%, better still from 0.5% to 20% and even better still from 1% to 15% of the total weight of the composition.

Thickeners Capable of Establishing Hydrogen Interactions

According to another embodiment, the composition according to the invention may comprise as structuring agent at least one thickener comprising at least one group and preferably at least two groups capable of establishing hydrogen interactions, chosen from:
polymeric thickeners, and
organogelling agents,
combined with the said compound A described previously.

Preferably, the composition according to the invention comprises at least one thickener comprising at least one group and preferably at least two groups capable of establishing hydrogen interactions, chosen from polymeric thickeners and organogelling agents.

The combination of a supramolecular compound as described previously with a thickener capable of establishing hydrogen interactions especially makes it possible, in particular in compositions for making up or caring for keratin materials, and particularly the skin or the lips, to obtain uniform mixing and a glossy and preferably non-tacky deposit on the keratin materials.

Preferably, the thickener is present in the composition in a total content:
- ranging from 0.1% to 70% by weight relative to the total weight of the composition, preferably ranging from 0.5% to 50% by weight and better still ranging from 1% to 45% by weight relative to the total weight of the said composition, when it is chosen from polymeric thickeners, or
- ranging from 0.1% to 20% by weight, especially from 0.5% to 15% by weight or even from 0.5% to 10% by weight, better still from 1% to 8% by weight and even better still from 2% to 5% by weight relative to the total weight of the said composition, when it is chosen from organogelling agents.

According to the invention, the polymeric thickeners used comprising at least one unit comprising at least one group and preferably at least two groups capable of establishing hydrogen interactions may belong to the following two families:

1) polymers comprising at least two groups capable of establishing hydrogen interactions, these two groups being located in the polymer chain, and/or 2) polymers comprising at least two groups capable of establishing hydrogen interactions, these two groups being located on grafts or branches.

For the purposes of the invention, the term "polymer" means a compound containing at least two repeating units and preferably at least three repeating units.

For the purposes of the invention, the term "hydrocarbon-based repeating unit" means a unit comprising from 2 to 80 carbon atoms and preferably from 2 to 60 carbon atoms, bearing hydrogen atoms and optionally oxygen atoms, which may be linear, branched or cyclic, and saturated or unsaturated. These units each also comprise one or more nonpendent heteroatoms that are in the polymer backbone. These heteroatoms are chosen from nitrogen, sulfur, phosphorus and silicon atoms and combinations thereof, optionally combined with one or more oxygen atoms.

Preferably, these groups are chosen from ester, amide, sulfonamide, carbamate, thiocarbamate, urea, urethane, thiourea, oxamido, guanidino and biguanidino groups, and combinations thereof.

As polymeric thickeners that may be used, comprising at least one unit comprising at least one group and preferably at least two groups capable of establishing hydrogen interactions, examples that may be mentioned include:
- polymers with a weight-average molecular mass of less than 100 000, comprising a) a polymer backbone with hydrocarbon-based repeating units containing at least one heteroatom, and optionally b) at least one pendent fatty chain and/or at least one terminal fatty chain, optionally functionalized, containing from 6 to 120 carbon atoms and being linked to these hydrocarbon-based units, as described in patent applications WO-A-02/056 847 and WO-A-02/47619, the content of which is incorporated herein by reference; in particular polyamide resins (especially comprising alkyl groups containing from 12 to 22 carbon atoms) such as those described in U.S. Pat. No. 5,783,657, the content of which is incorporated herein by reference,
- silicone polyamide resins as described in patent application EP-A-1 266 647, and in the French patent application filed under No. 0 216 039, the content of which is incorporated herein by reference,
- organopolysiloxanes comprising at least one carboxyl group, and preferably organopolysiloxanes comprising at least two carboxyl groups, per unit.

Such thickeners are described especially in patent application EP-A-1 400 234, the content of which is incorporated herein by reference, and are described in greater detail hereinbelow.

Silicone Polyamide

According to a first embodiment of the invention, the polymeric structuring agent comprising groups capable of establishing hydrogen bonds is a silicone polyamide.

The silicone polyamides are preferably solid at room temperature (25° C.) and atmospheric pressure (760 mmHg).

For the purposes of the invention, the term "polymer" means a compound containing at least two repeating units, preferably at least three repeating units and better still 10 repeating units.

The silicone polyamides of the composition of the invention may be polymers of the polyorganosiloxane type, for instance those described in documents U.S. Pat. Nos. 5,874,069, 5,919,441, 6,051,216 and 5,981,680. According to the invention, the silicone polymers may belong to the following two families:

(1) polyorganosiloxanes comprising at least two amide groups, these two groups being located in the polymer chain, and/or (2) polyorganosiloxanes comprising at least two amide groups, these two groups being located on grafts or branches.

A) According to a first variant, the silicone polymers are polyorganosiloxanes as defined above in which the amide units are located in the polymer chain.

The silicone polyamides may more particularly be polymers comprising at least one unit corresponding to the general formula I:

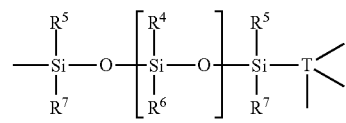

silicone polyamides, preferably comprising at least one unit corresponding to the general formula I:

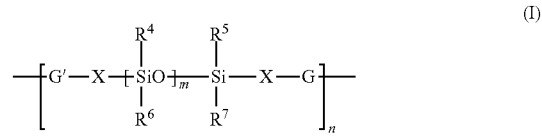

in which:

1) G' represents C(O) when G represents —C(O)—NH—Y—NH—, and G' represents —NH— when G represents —NH—C(O)—Y—C(O)—, 2) $R^4$, $R^5$, $R^6$ and $R^7$, which may be identical or different, represent a group chosen from:
- linear, branched or cyclic, saturated or unsaturated, $C_1$-$C_{40}$ hydrocarbon-based groups, possibly containing in their chain one or more oxygen, sulfur and/or nitrogen atoms, and possibly being partially or totally substituted with fluorine atoms,
- $C_6$-$C_{10}$ aryl groups, optionally substituted with one or more $C_1$-$C_4$ alkyl groups, polyorganosiloxane chains possibly containing one or more oxygen, sulfur and/or nitrogen atoms;

3) the groups X, which may be identical or different, represent a linear or branched $C_1$-$C_{30}$ alkylenediyl group, possibly containing in its chain one or more oxygen and/or nitrogen atoms;

4) Y is a saturated or unsaturated, $C_1$-$C_{50}$ linear or branched divalent alkylene, arylene, cycloalkylene, alkylarylene or arylalkylene group, possibly comprising one or more oxygen, sulfur and/or nitrogen atoms, and/or bearing as substituent one of the following atoms or groups of atoms: fluorine, hydroxyl, $C_3$-$C_8$ cycloalkyl, $C_1$-$C_{40}$ alkyl, $C_5$-$C_{10}$ aryl, phenyl optionally substituted with 1 to 3 $C_1$-$C_3$ alkyl, $C_1$-$C_3$ hydroxyalkyl and $C_1$-$C_6$ aminoalkyl groups; or 5) Y represents a group corresponding to the formula:

in which

T represents a linear or branched, saturated or unsaturated, $C_3$-$C_{24}$ trivalent or tetravalent hydrocarbon-based group optionally substituted with a polyorganosiloxane chain, and possibly containing one or more atoms chosen from O, N and S, or T represents a trivalent atom chosen from N, P and Al, and $R^8$ represents a linear or branched $C_1$-$C_{50}$ alkyl group or a polyorganosiloxane chain, possibly comprising one or more ester, amide, urethane, thiocarbamate, urea, thiourea and/or sulfonamide groups, which may possibly be linked to another chain of the polymer;

6) n is an integer ranging from 2 to 500 and preferably from 2 to 200, and m is an integer ranging from 1 to 1000, preferably from 1 to 700 and better still from 6 to 200.

Preferably, m is an integer ranging from 50 to 150.

According to the second variant, the polyorganosiloxanes may be polymers comprising at least one unit corresponding to formula (II):

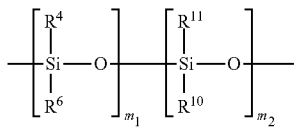

in which $R^4$ and $R^6$, which may be identical or different, are as defined above for formula (I), $R^{10}$ represents a group as defined above for $R^4$ and $R^6$, or represents a group of formula —X-G-$R^{12}$ in which X and G are as defined above for formula (I) and $R^{12}$ represents a hydrogen atom or a linear, branched or cyclic, saturated or unsaturated, $C_1$ to $C_{50}$ hydrocarbon-based group optionally comprising in its chain one or more atoms chosen from O, S and N, optionally substituted with one or more fluorine atoms and/or one or more hydroxyl groups, or a phenyl group optionally substituted with one or more $C_1$ to $C_4$ alkyl groups, $R^{11}$ represents a group of formula —X-G-$R^{12}$ in which X, G and $R^{12}$ are as defined above, $m_1$ is an integer ranging from 1 to 998, and $m_2$ is an integer ranging from 2 to 500.

According to the invention, the silicone polymer used as structuring agent may be a homopolymer, i.e. a polymer comprising several identical units, in particular units of formula (I) or of formula (II).

According to the invention, it is also possible to use a silicone polymer formed from a copolymer comprising several different units of formula (I), i.e. a polymer in which at least one of the groups $R^4$, $R^5$, $R^6$, $R^7$, X, G, Y, m and n is different in one of the units. The copolymer may also be formed from several units of formula (II), in which at least one of the groups $R^4$, $R^6$, $R^{10}$, $R^{11}$, $m_1$ and $m_2$ is different in at least one of the units.

It is also possible to use a polymer comprising at least one unit of formula (I) and at least one unit of formula (II), the units of formula (I) and the units of formula (II) possibly being identical to or different from each other.

According to one variant of the invention, it is also possible to use a polymer furthermore comprising at least one hydrocarbon-based unit comprising two groups capable of establishing hydrogen interactions, chosen from ester, amide, sulfonamide, carbamate, thiocarbamate, urea, urethane, thiourea, oxamido, guanidino and biguanidino groups, and combinations thereof.

These copolymers may be block polymers or grafted polymers.

According to one advantageous embodiment of the invention, the groups capable of establishing hydrogen interactions are amide groups of formulae —C(O)NH— and —HN—C(O)—. In this case, the structuring agent may be a polymer comprising at least one unit of formula (III) or (IV):

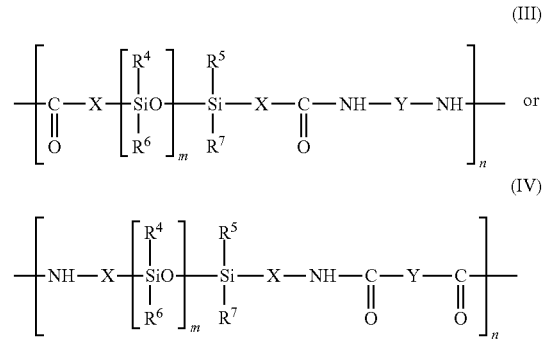

in which $R^4$, $R^5$, $R^6$, $R^7$, X, Y, m and n are as defined above. Such a unit may be obtained:

either via a condensation reaction between a silicone containing α,ω-carboxylic acid ends and one or more diamines, according to the following reaction scheme:

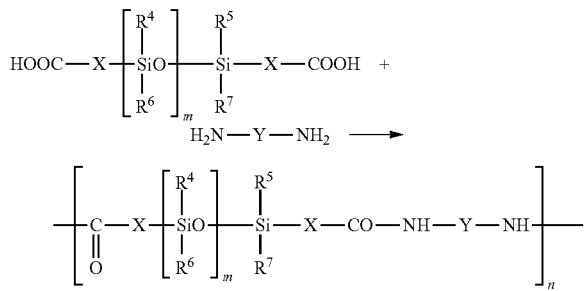

or via reaction of two molecules of α-unsaturated carboxylic acid with a diamine according to the following reaction scheme:

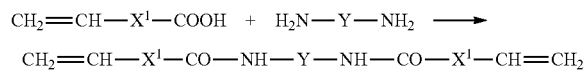

followed by the addition of a siloxane to the ethylenic unsaturations, according to the following scheme:

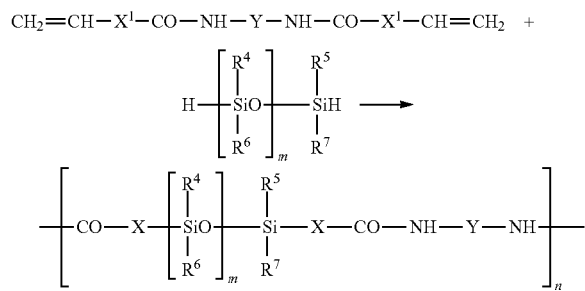

in which $X^1$—$(CH_2)_2$— corresponds to X defined above and Y, $R^4$, $R^5$, $R^6$, $R^7$ and m are as defined above;

or via reaction of a silicone containing α,ω-$NH_2$ ends and a diacid of formula HOOC—Y—COOH according to the following reaction scheme:

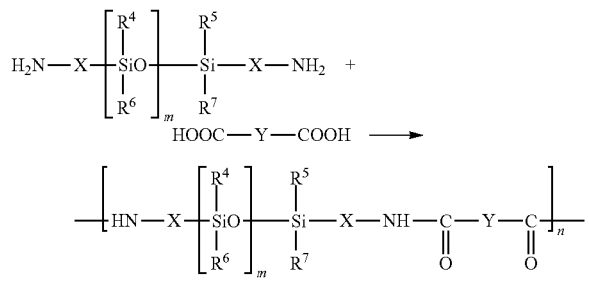

In these polyamides of formula (III) or (IV), m is in the range from 1 to 700, in particular from 15 to 500 and especially from 50 to 200, and n is in particular in the range from 1 to 500, preferably from 1 to 100 and better still from 4 to 25, X is preferably a linear or branched alkylene chain containing from 1 to 30 carbon atoms, in particular 1 to 20 carbon atoms, especially from 5 to 15 carbon atoms and more particularly 10 carbon atoms, and Y is preferably an alkylene chain that is linear or branched or that possibly comprises rings and/or unsaturations, containing from 1 to 40 carbon atoms, in particular from 1 to 20 carbon atoms and better still from 2 to 6 carbon atoms, in particular 6 carbon atoms.

In formulae (III) and (IV), the alkylene group representing X or Y can optionally contain in its alkylene portion at least one of the following members:
1) 1 to 5 amide, urea, urethane or carbamate groups,
2) a $C_5$ or $C_6$ cycloalkyl group, and
3) a phenylene group optionally substituted with 1 to 3 identical or different $C_1$ to $C_3$ alkyl groups.

In formulae (III) and (IV), the alkylene groups may also be substituted with at least one member chosen from the group consisting of:
a hydroxyl group,
a $C_3$ to $C_8$ cycloalkyl group,
one to three $C_1$ to $C_{40}$ alkyl groups,
a phenyl group optionally substituted with one to three $C_1$ to $C_3$ alkyl groups,
a $C_1$ to $C_3$ hydroxyalkyl group, and
a $C_1$ to $C_6$ aminoalkyl group.

In these formulae (III) and (IV), Y may also represent:

in which $R^8$ represents a polyorganosiloxane chain and T represents a group of formula:

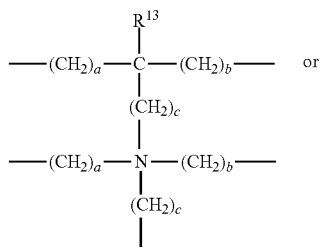

in which a, b and c are, independently, integers ranging from 1 to 10, and $R^{16}$ is a hydrogen atom or a group such as those defined for $R^4$, $R^5$, $R^6$ and $R^7$.

In formulae (III) and (IV), $R^4$, $R^5$, $R^6$ and $R^7$ preferably represent, independently, a linear or branched $C_1$ to $C_{40}$ alkyl group, preferably a $CH_3$, $C_2H_5$, n-$C_3H_7$ or isopropyl group, a polyorganosiloxane chain or a phenyl group optionally substituted with one to three methyl or ethyl groups.

As has been seen previously, the polymer may comprise identical or different units of formula (III) or (IV).

Thus, the polymer may be a polyamide containing several units of formula (III) or (IV) of different lengths, i.e. a polyamide corresponding to formula (V):

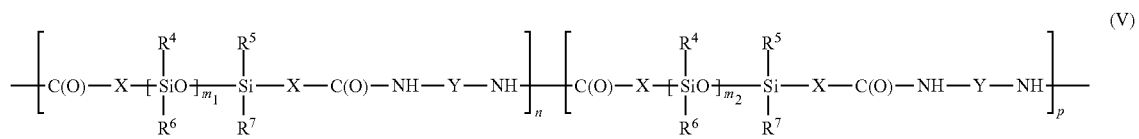

in which X, Y, n and $R^4$ to $R^7$ have the meanings given above, $m_1$ and $m_2$, which are different, are chosen in the range from 1 to 1000, and p is an integer ranging from 2 to 300.

In this formula, the units may be structured to form either a block copolymer, or a random copolymer or an alternating copolymer. In this copolymer, the units may be not only of different lengths, but also of different chemical structures, for example containing different groups Y. In this case, the polymer may correspond to formula VI:

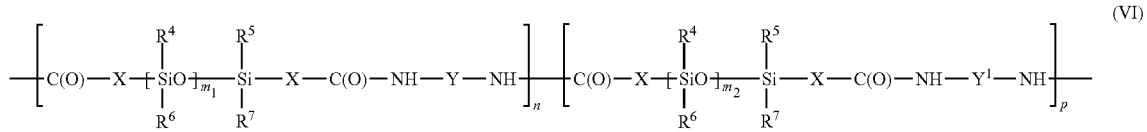

in which $R^4$ to $R^7$, X, Y, $m_1$, $m_2$, n and p have the meanings given above and $Y^1$ is different from Y but chosen from the groups defined for Y. As previously, the various units may be structured to form either a block copolymer, or a random copolymer or an alternating copolymer.

In this first embodiment of the invention, the structuring agent may also consist of a grafted copolymer. Thus, the polyamide containing silicone units may be grafted and optionally crosslinked with silicone chains containing amide groups. Such polymers may be synthesized with trifunctional amines.

In this case, the polymer may comprise at least one unit of formula (VII):

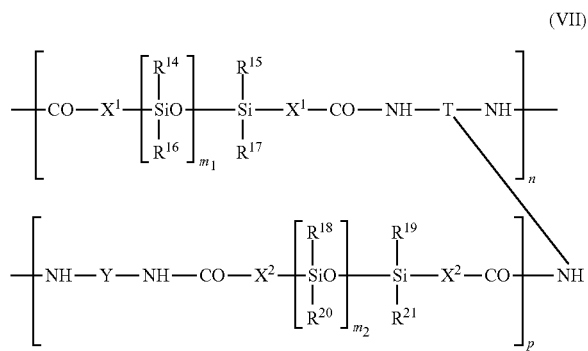

in which $X^1$ and $X^2$, which are identical or different, have the meaning given for X in formula (I), n is as defined in formula (I), Y and T are as defined in formula (I), $R^{14}$ to $R^{21}$ are groups chosen from the same group as $R^4$ to $R^7$, $m_1$ and $m_2$ are numbers in the range from 1 to 1000, and p is an integer ranging from 2 to 500.

In formula (VII), it is preferred that:

p is in the range from 1 to 25 and better still from 1 to 7, $R^{14}$ to $R^{21}$ are methyl groups, T corresponds to one of the following formulae:

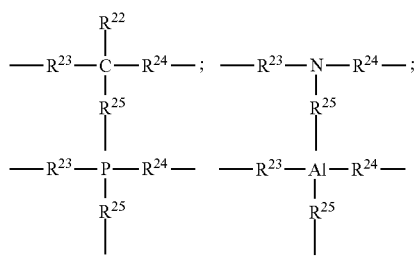

in which $R^{22}$ is a hydrogen atom or a group chosen from the groups defined for $R^4$ to $R^7$, and $R^{23}$, $R^{24}$ and $R^{25}$ are, independently, linear or branched alkylene groups, and more preferably correspond to the formula:

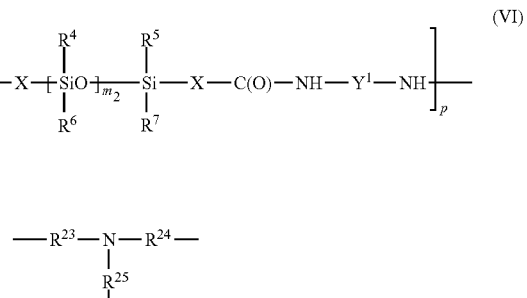

in particular with $R^{23}$, $R^{24}$ and $R^{25}$ representing —$CH_2$—$CH_2$—, $m_1$ and $m_2$ are in the range from 15 to 500 and better still from 15 to 45, $X^1$ and $X^2$ represent —$(CH_2)_{10}$—, and Y represents —$CH_2$—.

These polyamides containing a grafted silicone unit of formula (VII) may be copolymerized with polyamide-silicones of formula (II) to form block copolymers, alternating copolymers or random copolymers. The weight percentage of grafted silicone units (VII) in the copolymer may range from 0.5% to 30% by weight.

According to the invention, as has been seen previously, the siloxane units may be in the main chain or backbone of the polymer, but they may also be present in grafted or pendent chains. In the main chain, the siloxane units may be in the form of segments as described above. In the pendent or grafted chains, the siloxane units may appear individually or in segments.

According to one embodiment variant of the invention, a copolymer of silicone polyamide and of hydrocarbon-based polyamide, or a copolymer comprising units of formula (III) or (IV) and hydrocarbon-based polyamide units, may be used. In this case, the polyamide-silicone units may be located at the ends of the hydrocarbon-based polyamide.

According to one preferred embodiment, the silicone polyamide comprises units of formula III, preferably in which the groups $R^4$, $R^5$, $R^6$ and $R^7$ represent methyl groups, one from among X and Y represents an alkylene group of 6 carbon atoms and the other represents an alkylene group of 11 carbon atoms, n representing the degree of polymerization DP of the polymer.

Examples of such silicone polyamides that may be mentioned include the compounds sold by the company Dow Corning under the name DC 2-8179 (DP 100) and DC 2-8178 (DP 15), the INCI name of which is Nylon-611/dimethicone copolymers.

Advantageously, the composition according to the invention comprises at least one polydimethylsiloxane block polymer of general formula (I) with an index m of about 100. The index "m" corresponds to the degree of polymerization of the silicone part of the polymer.

More preferably, the composition according to the invention comprises at least one polymer comprising at least one unit of formula (III) in which m ranges from to 200, in particular from 75 to 150 and is more particularly about 100.

Preferably also, $R^4$, $R^5$, $R^6$ and $R^7$ independently represent, in formula (III), a linear or branched $C_1$-$C_{40}$ alkyl group, preferably a $CH_3$, $C_2H_5$, n-$C_3H_7$ or isopropyl group.

As examples of silicone polymers that may be used, mention may be made of one of the silicone polyamides obtained in accordance with Examples 1 to 3 of document U.S. Pat. No. 5,981,680.

According to one preferred mode, the polyamide silicone polymer sold by the company Dow Corning under the name DC 2-8179 (DP 100) is used.

According to one embodiment variant of the invention, the polymer is formed from a homopolymer or copolymer comprising urethane or urea groups. These polymers are described in detail in patent application WO 2003/106 614 published on 24 Dec. 2003, the content of which is incorporated into the present patent application by reference.

As previously, such a polymer may comprise polyorganosiloxane units containing two or more urethane and/or urea groups, either in the backbone of the polymer or on side chains or as pendent groups. The polymers comprising at least two urethane and/or urea groups in the backbone may be polymers comprising at least one unit corresponding to the following formula (VIII):

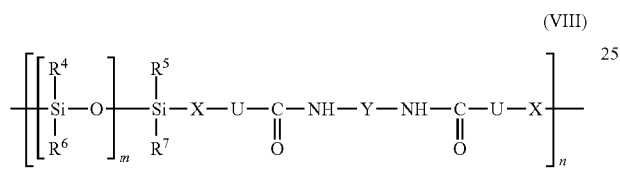

(VIII)

in which $R^4$, $R^5$, $R^6$, $R^7$, X, Y, m and n have the meanings given above for formula (I), and U represents —O— or —NH—, such that:

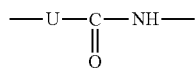

corresponds to a urethane or urea group.

In this formula (VIII), Y may be a linear or branched $C_1$ to $C_{40}$ alkylene group, optionally substituted with a $C_1$ to $C_{15}$ alkyl group or a $C_5$ to $C_{o1}$ aryl group. Preferably, a —(CH$_2$)$_6$— group is used.

Y may also represent a $C_5$ to $C_{12}$ cycloaliphatic or aromatic group that may be substituted with a $C_1$ to $C_{15}$ alkyl group or a $C_5$ to $C_{o1}$ aryl group, for example a radical chosen from the methylene-4,4-biscyclohexyl radical, the radical derived from isophorone diisocyanate, 2,4- and 2,6-tolylenes, 1,5-naphthylene, p-phenylene and 4,4'-biphenylenemethane. Generally, it is preferred for Y to represent a linear or branched $C_1$ to $C_{40}$ alkylene radical or a $C_4$ to $C_{12}$ cycloalkylene radical.

Y may also represent a polyurethane or polyurea block corresponding to the condensation of several diisocyanate molecules with one or more molecules of coupling agents of the diol or diamine type. In this case, Y comprises several urethane or urea groups in the alkylene chain.

It may correspond to formula (IX):

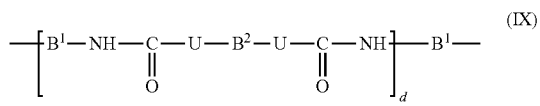

(IX)

in which $B^1$ is a group chosen from the groups given above for Y, U is —O— or —NH— and $B^2$ is chosen from:

linear or branched $C_1$ to $C_{40}$ alkylene groups, $C_5$ to $C_{12}$ cycloalkylene groups, optionally bearing alkyl substituents, for example one to three methyl or ethyl groups, or alkylene, for example the diol radical: cyclohexanedimethanol, phenylene groups that may optionally bear $C_1$ to $C_3$ alkyl substituents, and groups of formula:

in which T is a hydrocarbon-based trivalent radical possibly containing one or more heteroatoms such as oxygen, sulfur and nitrogen and $R^8$ is a polyorganosiloxane chain or a linear or branched $C_1$ to $C_{50}$ alkyl chain.

T can represent, for example:

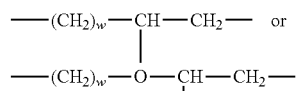

with w being an integer ranging from 1 to 10 and $R^8$ being a polyorganosiloxane chain.

When Y is a linear or branched $C_1$ to $C_{40}$ alkylene group, the —(CH$_2$)$_2$— and —(CH$_2$)$_6$— groups are preferred.

In the formula given above for Y, d may be an integer ranging from 0 to 5, preferably from 0 to 3 and more preferably equal to 1 or 2.

Preferably, $B^2$ is a linear or branched $C_1$ to $C_{40}$ alkylene group, in particular —(CH$_2$)$_2$— or —(CH$_2$)$_6$— or a group:

with $R^8$ being a polyorganosiloxane chain.

As previously, the silicone polymer may be formed from silicone urethane and/or silicone urea units of different length and/or constitution, and may be in the form of block or random copolymers.

The polymers of formula (VIII) comprising urea or urethane groups in the chain of the silicone polymer may be obtained by reaction between a silicone containing $\alpha,\omega$-NH$_2$ or —OH end groups, of formula:

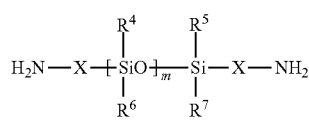

in which m, $R^4$, $R^5$, $R^6$, $R^7$ and X are as defined for formula (I), and a diisocyanate OCN—Y—NCO in which Y has the meaning given in formula (I); and optionally a diol or diamine coupling agent of formula H$_2$N—B$^2$—NH$_2$ or HO—B$^2$—OH, in which $B^2$ is as defined in formula (IX).

According to the stoichiometric proportions between the two reagents, diisocyanate and coupling agent, Y may have the formula (IX) with d equal to 0 or d equal to 1 to 5.

As in the case of the polyamide silicones of formula (IV), (II) or (III), it is possible to use in the invention polyurethane or polyurea silicones containing units of different length and structure, in particular units whose lengths differ by the number of silicone units. In this case, the copolymer may correspond, for example, to the formula:

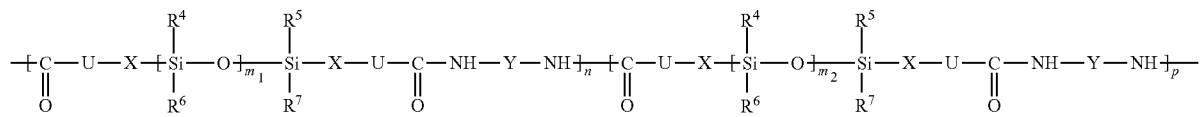

(XII)

in which $R^4$, $R^5$, $R^6$, $R^7$, X, Y and U are as defined for formula (VIII) and $m_1$, $m_2$, n and p are as defined for formula (V).

According to the invention, the silicone may also comprise urethane and/or urea groups no longer in the backbone but as side branches.

In this case, the polymer may comprise at least one unit of formula:

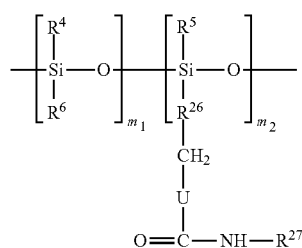

(X)

in which $R^4$, $R^6$, $R^5$, $m_1$ and $m_2$ have the meanings given above for formula (II), and $R^5$ for formula (I), U represents O or NH, $R^{26}$ represents a $C_1$ to $C_{40}$ alkylene group, optionally comprising one or more heteroatoms chosen from O and N, or a phenylene group, and $R^{27}$ is chosen from linear, branched or cyclic, saturated or unsaturated $C_1$ to $C_{50}$ alkyl groups, and phenyl groups optionally substituted with one to three $C_1$ to $C_3$ alkyl groups.

The polymers comprising at least one unit of formula (X) contain siloxane units and urea or urethane groups, and they may be used as structuring polymer in the compositions of the invention.

The siloxane polymers may have a single urea or urethane group by branching or may have branches containing two urea or urethane groups, or alternatively they may contain a mixture of branches containing one urea or urethane group and branches containing two urea or urethane groups.

They may be obtained from branched polysiloxanes, comprising one or two amino groups per branch, by reacting these polysiloxanes with monoisocyanates.

As examples of starting polymers of this type containing amino and diamino branches, mention may be made of the polymers corresponding to the following formulae:

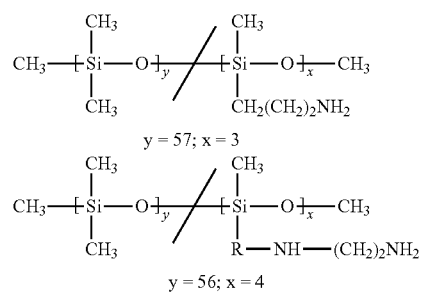

In these formulae, the symbol "/" indicates that the segments may be of different lengths and in a random order, and R represents a linear aliphatic group preferably containing 1 to 6 carbon atoms and better still 1 to 3 carbon atoms.

Such polymers containing branching may be formed by reacting a siloxane polymer, containing at least three amino groups per polymer molecule, with a compound containing only one monofunctional group (for example an acid, an isocyanate or an isothiocyanate) to react this monofunctional group with one of the amino groups and to form groups capable of establishing hydrogen interactions. The amino groups may be on side chains extending from the main chain of the siloxane polymer, such that the groups capable of establishing hydrogen interactions are formed on these side chains, or alternatively the amino groups may be at the ends of the main chain, such that the groups capable of hydrogen interaction will be end groups of the polymer.

As a procedure for forming a polymer containing siloxane units and groups capable of establishing hydrogen interactions, mention may be made of the reaction of a siloxane diamine and of a diisocyanate in a silicone solvent so as to provide a gel directly. The reaction may be performed in a silicone fluid, the resulting product being dissolved in the silicone fluid, at high temperature, the temperature of the system then being reduced to form the gel.

The polymers that are preferred for incorporation into the compositions according to the present invention are siloxane-urea copolymers that are linear and that contain urea groups as groups capable of establishing hydrogen interactions in the backbone of the polymer.

As an illustration of a polysiloxane ending with four urea groups, mention may be made of the polymer of formula:

(XI)

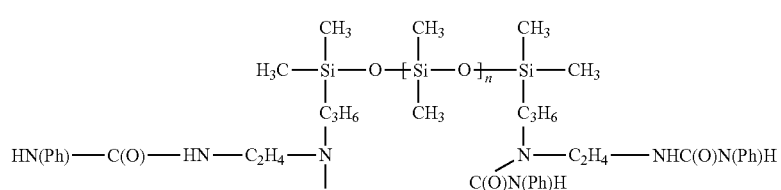

(Ph = Phenyl)

in which Ph is a phenyl group and n is a number from 0 to 300 and in particular from 0 to 100, for example 50.

This polymer is obtained by reacting the following polysiloxane containing amino groups:

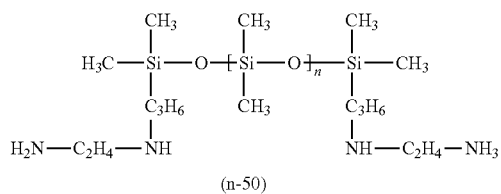

(n-50)

with phenyl isocyanate.

Branched polyurethane or polyurea silicones may also be obtained by using, instead of the diisocyanate OCN—Y—NCO, a triisocyanate of formula:

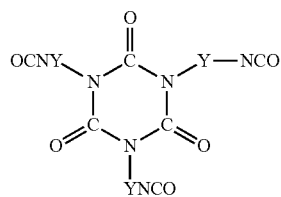

A polyurethane or polyurea silicone containing branches comprising an organosiloxane chain with groups capable of establishing hydrogen interactions is thus obtained. Such a polymer comprises, for example, a unit corresponding to the formula:

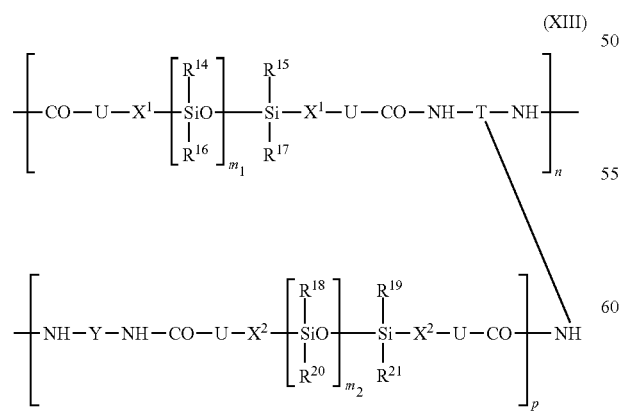

(XIII)

in which $X^1$ and $X^2$, which are identical or different, have the meaning given for X in formula (I), n is as defined in formula (I), Y and T are as defined in formula (I), $R^{14}$ to $R^{21}$ are groups chosen from the same group as $R^4$ to $R^7$, $m_1$ and $m_2$ are numbers in the range from 1 to 1000, and p is an integer ranging from 2 to 500.

As in the case of the polyamides, copolymers of polyurethane or polyurea silicone and of hydrocarbon-based polyurethane or polyurea may be used in the invention by performing the reaction for synthesizing the polymer in the presence of an α,ω-difunctional block of non-silicone nature, for example a polyester, a polyether or a polyolefin.

As has been seen previously, the copolymers of the invention may contain siloxane units in the main chain of the polymer and groups capable of establishing hydrogen interactions, either in the main chain of the polymer or at the ends thereof, or on side chains or branches of the main chain. This may correspond to the following five arrangements:

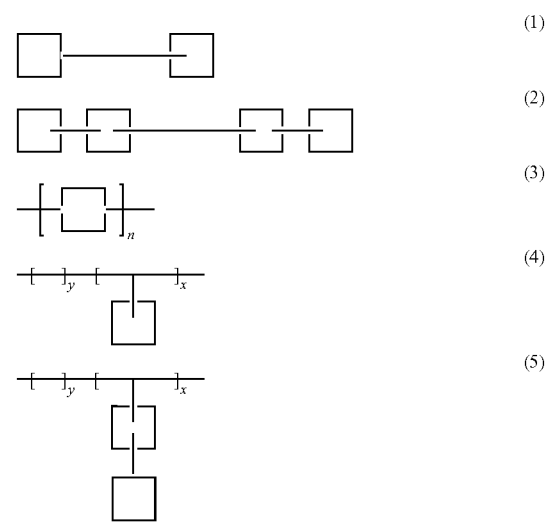

in which the continuous line is the main chain of the siloxane polymer and the squares represent the groups capable of establishing hydrogen interactions.

In case (1), the groups capable of establishing hydrogen interactions are located at the ends of the main chain. In case (2), two groups capable of establishing hydrogen interactions are located at each of the ends of the main chain.

In case (3), the groups capable of establishing hydrogen interactions are located within the main chain in repeating units.

In cases (4) and (5), these are copolymers in which the groups capable of establishing hydrogen interactions are located on branches of the main chain of a first series of units that are copolymerized with units not comprising groups capable of establishing hydrogen interactions.

The polymers and copolymers used in the composition of the invention advantageously have a transition temperature from the solid state to the liquid state ranging from 45° C. to 190° C. They preferably have a transition temperature from the solid state to the liquid state ranging from 70 to 130° C. and better still from 80° C. to 105° C.

The silicone polyamide may be present in the first composition in a total content ranging from 0.5% to 70% by weight relative to the total weight of the composition, preferably ranging from 2% to 50% by weight, better still ranging from 5% to 45% by weight and preferably ranging from 5% to 40% by weight relative to the total weight of the said composition.

The combination of a supramolecular compound as described previously with a silicone polyamide especially makes it possible, in particular in compositions for making up or caring for keratin materials, and particularly the skin or the lips, to obtain uniform mixing and a glossy, non-tacky deposit on the keratin materials.

Polyamide

According to a second embodiment of the invention, the polymeric structuring agent comprising groups capable of establishing hydrogen bonds is a polymer with a weight-average molecular mass of less than 100 000, comprising a) a polymer backbone with hydrocarbon-based repeating units containing at least one heteroatom, and optionally b) at least one pendent fatty chain and/or at least one terminal fatty chain, optionally functionalized, containing from 6 to 120 carbon atoms and being linked to these hydrocarbon-based units, as described in patent applications WO-A-02/056 847 and WO-A-02/47619, the content of which is incorporated herein by reference; in particular polyamide resins (especially comprising alkyl groups containing from 12 to 22 carbon atoms) such as those described in U.S. Pat. No. 5,783,657, the content of which is incorporated herein by reference.

The structuring polymer of the composition of the invention is an undeformable solid at room temperature (25° C.). It is capable of structuring the composition without opacifying it.

For the purposes of the invention, the term "functionalized chain" means an alkyl chain comprising one or more functional groups or reagents chosen especially from hydroxyl, ether, oxyalkylene or polyoxyalkylene, halogen, including fluoro or perfluoro groups, ester, siloxane and polysiloxane groups. In addition, the hydrogen atoms of one or more fatty chains may be at least partially replaced with fluorine atoms.

For the purposes of the invention, the term "polymer" means a compound containing at least two repeating units.

For the purposes of the invention, the term "hydrocarbon-based repeating unit" means a unit comprising from 2 to 80 carbon atoms and preferably from 2 to 60 carbon atoms, bearing hydrogen atoms and optionally oxygen atoms, which may be linear, branched or cyclic, and saturated or unsaturated. These units each also comprise one or more heteroatoms that are advantageously non-pendent and that are in the polymer backbone. These heteroatoms are chosen from nitrogen, sulfur and phosphorus atoms, and combinations thereof, optionally combined with one or more oxygen atoms. Preferably, the units comprise at least one nitrogen atom that in particular is non-pendent. These units also advantageously comprise a carbonyl group.

The units containing a heteroatom are, in particular, amide units forming a backbone of the polyamide type, carbamate and/or urea units forming a polyurethane, polyurea and/or polyurea-urethane backbone. These units are preferably amide units. The pendent chains are advantageously linked directly to at least one of the heteroatoms of the polymer backbone.

Between the hydrocarbon-based units, this polymer may comprise silicone units or oxyalkylene units.

In addition, this polymer of the composition of the invention advantageously comprises from 40% to 98% of fatty chains relative to the total number of units containing a heteroatom and of fatty chains, and better still from 50% to 95%. The nature and proportion of the units containing a heteroatom depends on the nature of the fatty phase and is, in particular, similar to the polar nature of the fatty phase. Thus, the more the units containing a heteroatom are polar and in high proportion in this first polymer, which corresponds to the presence of several heteroatoms, the greater the affinity of the first polymer for polar oils. On the other hand, the less polar or even apolar the units containing a heteroatom or the lower their proportion, the greater the affinity of the first polymer for apolar oils.

This polymer is advantageously a polyamide, preferably a polyamide polymer with a weight-average molecular mass of less than 100 000, comprising a) a polymer backbone containing amide repeating units, and b) optionally at least one pendent fatty chain and/or at least one terminal chain, which may be functionalized, containing from 8 to 120 carbon atoms and being linked to these amide units.

The pendent fatty chains are preferably linked to at least one of the nitrogen atoms of the amide units of this polymer.

In particular, the fatty chains of this polyamide represent from 40% to 98% and better still from 50% to 95% of the total number of amide units and of fatty chains.

Advantageously, this polymer, and in particular this polyamide, of the composition according to the invention has a weight-average molecular mass of less than 100 000 (especially ranging from 1000 to 100 000), in particular less than 50 000 (especially ranging from 1000 to 50 000) and more particularly ranging from 1000 to 30 000, preferably from 2000 to 20 000 and better still from 2000 to 10 000.

This polymer, and in particular this polyamide, is insoluble in water, especially at 25° C. In particular, it contains no ionic groups.

As preferred polymers that may be used in the invention, mention may be made of polyamides branched with pendent fatty chains and/or terminal fatty chains containing from 6 to 120 carbon atoms and better still from 8 to 120 and in particular from 12 to 68 carbon atoms, each terminal fatty chain being linked to the polyamide backbone via at least one bonding group, in particular an ester. These polymers preferably comprise a fatty chain at each end of the polymer backbone and in particular of the polyamide backbone. Other bonding groups which may be mentioned are ether, amine, urea, urethane, thioester, thiourea and thiourethane groups.

These polymers are preferably polymers resulting from a polycondensation between a dicarboxylic acid containing at least 32 carbon atoms (in particular containing from 32 to 44 carbon atoms) and an amine chosen from diamines containing at least 2 carbon atoms (in particular from 2 to 36 carbon atoms) and triamines containing at least 2 carbon atoms (in particular from 2 to 36 carbon atoms). The diacid is preferably a dimer of a fatty acid containing ethylenic unsaturation containing at least 16 carbon atoms, preferably from 16 to 24 carbon atoms, for instance oleic acid, linoleic acid or linolenic acid. The diamine is preferably ethylenediamine, hexylenediamine or hexamethylene-diamine. The triamine is, for example, ethylenetriamine. For the polymers comprising one or two terminal carboxylic acid groups, it is advantageous to esterify them with a monoalcohol containing at least four carbon atoms, preferably from 10 to 36 carbon atoms, better still from 12 to 24 and even better from 16 to 24, for example 18 carbon atoms.

These polymers are more especially those disclosed in document U.S. Pat. No. 5,783,657 from the company Union Camp. Each of these polymers in particular satisfies formula (I) below:

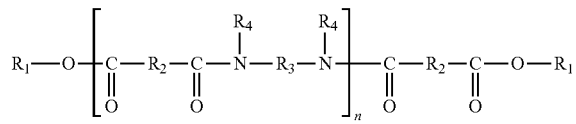
(I)

in which n denotes a number of amide units such that the number of ester groups represents from 10% to 50% of the total number of ester and amide groups; $R_1$ is, independently in each case, an alkyl or alkenyl group containing at least 4 carbon atoms and in particular from 4 to 24 carbon atoms; $R_2$ represents, independently in each case, a $C_4$ to $C_{42}$ hydrocarbon-based group, on condition that 50% of the groups $R_2$ represent a $C_{30}$ to $C_{42}$ hydrocarbon-based group; $R_3$ represents, independently in each case, an organic group containing at least 2 carbon atoms, hydrogen atoms and optionally one or more oxygen or nitrogen atoms; and $R_4$ represents, independently in each case, a hydrogen atom, a $C_1$ to $C_{10}$ alkyl group or a direct bond to $R_3$ or to another $R_4$, such that the nitrogen atom to which $R_3$ and $R_4$ are both attached forms part of a heterocyclic structure defined by $R_4$—N—$R_3$, with at least 50% of the groups $R_4$ representing a hydrogen atom.

In the particular case of formula (I), the terminal fatty chains that are optionally functionalized for the purposes of the invention are terminal chains linked to the last heteroatom, in this case nitrogen, of the polyamide backbone.

In particular, the ester groups of formula (I), which form part of the terminal and/or pendent fatty chains for the purposes of the invention, represent from 15% to 40% of the total number of ester and amide groups and better still from 20% to 35%. Furthermore, n is advantageously an integer ranging from 1 to 5 and better still greater than 2. Preferably, $R_1$ is a $C_{12}$ to $C_{22}$ and preferably $C_{16}$ to $C_{22}$ alkyl group. Advantageously, $R_2$ can be a $C_{10}$ to $C_{42}$ hydrocarbon-based (alkylene) group. Preferably, at least 50% and better still at least 75% of the groups $R_2$ are groups containing from 30 to 42 carbon atoms. The other groups $R_2$ are $C_4$ to $C_{19}$ and better still $C_4$ to $C_{12}$ hydrogen-containing groups. Preferably, $R_3$ represents a $C_2$ to $C_{36}$ hydrocarbon-based group or a polyoxyalkylene group and $R_4$ represents a hydrogen atom. Preferably, $R_3$ represents a $C_2$ to $C_{12}$ hydrocarbon-based group.

The hydrocarbon-based groups may be linear, cyclic or branched, and saturated or unsaturated groups. Moreover, the alkyl and alkylene groups may be linear or branched, and saturated or unsaturated groups.

In general, the polymers of formula (I) are in the form of mixtures of polymers, these mixtures also possibly containing a synthetic product corresponding to a compound of formula (I) in which n is 0, i.e. a diester.

As examples of polymers that may be used in the compositions according to the invention, mention may be made of the commercial products sold by the company Arizona Chemical under the names Uniclear 80 and Uniclear 100, the INCI name of which is ethylenediamine/stearyl dimer dilinoleate copolymer, or Uniclear 80 V, Uniclear 100 V and Uniclear 100 VG, the INCI name of which is ethylenediamine/stearyl dimer tallate copolymer. They are sold, respectively, in the form of an 80% (in terms of active material) gel in a mineral oil and a 100% (in terms of active material) gel.

They have a softening point of from 88 to 94° C. These commercial products are a mixture of copolymers of a $C_{36}$ diacid condensed with ethylenediamine, having a weight-average molecular mass of about 6000. The terminal ester groups result from the esterification of the remaining acid endings with cetyl alcohol, stearyl alcohol or mixtures thereof (also known as cetylstearyl alcohol).

As polymers that may be used in the compositions according to the invention, mention may also be made of polyamide resins resulting from the condensation of an aliphatic dicarboxylic acid and a diamine (including compounds containing more than 2 carbonyl groups and 2 amine groups), the carbonyl and amine groups of adjacent individual units being condensed via an amide bond. These polyamide resins are, in particular, those sold under the brand name Versamid® by the companies General Mills Inc. and Henkel Corp. (Versamid 930, 744 or 1655) or by the company Olin Mathieson Chemical Corp. under the brand name Onamid®, in particular Onamid S or C. These resins have a weight-average molecular mass ranging from 6000 to 9000. For further information regarding these polyamides, reference may be made to the documents U.S. Pat. Nos. 3,645,705 and 3,148,125. More especially, Versamid® 930 or 744 is used.

The polyamides sold by the company Arizona Chemical under the references Uni-Rez (2658, 2931, 2970, 2621, 2613, 2624, 2665, 1554, 2623 and 2662) and the product sold under the reference Macromelt 6212 by the company Henkel may also be used. For further information regarding these polyamides, reference may be made to document U.S. Pat. No. 5,500,209.

It is also possible to use polyamide resins, such as those disclosed in U.S. Pat. Nos. 5,783,657 and 5,998,570.

The polymer present in the composition according to the invention advantageously has a softening point of greater than 65° C., which may be up to 190° C. It preferably has a softening point ranging from 70° C. to 130° C. and better still from 80° C. to 105° C. The first polymer is in particular a non-waxy polymer.

The polymer(s) that may be used according to the invention have, as a result of their fatty chain(s), good solubility in oils and thus lead to macroscopically homogeneous compositions, even with a high content (at least 25%) of polymer.

This copolymer may be present in the composition according to the invention in a content ranging from 0.5% to 70% by weight relative to the total weight of the composition, preferably ranging from 2% to 50% by weight, better still ranging from 5% to 45% by weight and preferably ranging from 5% to 40% by weight relative to the total weight of the said composition.

The combination of a supramolecular compound as described previously with a polyamide especially makes it possible, in particular in compositions for making up or caring for keratin materials, and particularly the skin or the lips, to obtain uniform mixing and a glossy deposit on the keratin materials.

Organogelling Agents:

According to a second embodiment of the invention, the thickener comprising groups capable of establishing hydrogen bonds is non-polymeric, combined with the said compound A described previously.

According to this embodiment, the non-polymeric thickener is preferably an organogelling agent.

Organogelling agents are oily-medium thickeners, and in particular non-polymeric molecular organic gelling agents. Organogelling agents are compounds whose molecules are capable of establishing physical interactions with each other, in particular H bonds in the context of the present invention, leading to self-aggregation of the molecules with formation of a supramolecular 3D network that is responsible for the gelation of the oil(s) (also known as the liquid fatty phase).

The supramolecular network may result from the formation of a network of fibrils (caused by the stacking or aggregation of organogelling molecules), which immobilizes the molecules of the liquid fatty phase.

The ability to form this network of fibrils, and thus to gel, depends on the nature (or chemical class) of the organogelling agent, on the nature of the substituents borne by its molecules for a given chemical class, and on the nature of the liquid fatty phase.

The physical interactions are of diverse nature but exclude co-crystallization. These physical interactions are in particular interactions of self-complementary hydrogen interaction type, in the context of the present invention. Other types of interaction may also be involved, such as R interactions between unsaturated rings, dipolar interactions, coordination bonds with organometallic derivatives, and combinations thereof. In general, each molecule of an organogelling agent can establish several types of physical interaction with a neighbouring molecule.

According to the invention, the molecules of the organogelling agents according to the invention comprise at least one group capable of establishing hydrogen bonds and better still at least two groups, at least one aromatic ring and better still at least two aromatic rings, at least one or more ethylenically unsaturated bonds and/or at least one or more asymmetric carbons. Preferably, the groups capable of forming hydrogen bonds are chosen from hydroxyl, carbonyl, amine, carboxylic acid, amide, urea and benzyl groups, and combinations thereof.

The organogelling agent(s) according to the invention are soluble in the liquid fatty phase after heating to obtain a transparent uniform liquid phase. They may be solid or liquid at room temperature and atmospheric pressure.

The molecular organogelling agent(s) that may be used in the composition according to the invention is (are) especially those described in the document "Specialist Surfactants" edited by D. Robb, 1997, pp. 209-263, Chapter 8 by P. Terech, European patent applications EP-A-1 068 854 and EP-A-1 086 945, or alternatively in patent application WO-A-02/47031.

Mention may be made especially, among these organogelling agents, of amides of carboxylic acids, in particular of tricarboxylic acids, for instance cyclohexanetricarboxamides (see European patent application EP-A-1 068 854), diamides with hydrocarbon-based chains each containing from 1 to 22 carbon atoms, for example from 6 to 18 carbon atoms, the said chains being unsubstituted or substituted with at least one substituent chosen from ester, urea and fluoro groups (see patent application EP-A-1 086 945) and especially diamides resulting from the reaction of diamino-cyclohexane, in particular diaminocyclohexane in trans form, and of an acid chloride, for instance N,N'-bis-(dodecanoyl)-1,2-diaminocyclohexane, N-acylamino acid amides, for instance the diamides resulting from the action of an N-acylamino acid with amines containing from 1 to 22 carbon atoms, for instance those described in document WO-93/23008 and especially N-acylglutamic acid amides in which the acyl group represents a $C_8$ to $C_{22}$ alkyl chain, such as N-lauroyl-L-glutamic acid dibutylamide, manufactured or sold by the company Ajinomoto under the name GP-1, and mixtures thereof.

In particular, it may be advantageous to combine the resins according to the invention with particular organogelling agents, and especially the compounds of bis-urea type.

Advantageously, the thickener used in the composition according to the invention is an organogelling agent of bis-urea type.

In particular, the organogelling agent of bis-urea type may be chosen from:

the bis-ureas of general formula (I):

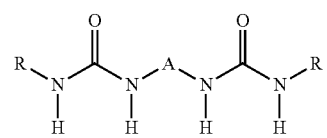

(I)

in which:

A is a group of formula:

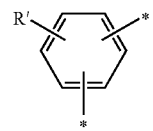

with R' being a linear or branched $C_1$-$C_4$ alkyl radical, and the *s symbolizing the points of attachment of the group A to each of the two nitrogen atoms of the rest of the compound of general formula (I), and R is a saturated or unsaturated, non-cyclic, mono-branched $C_6$ to $C_{15}$ alkyl radical, the hydrocarbon-based chain of which is optionally interrupted with 1 to 3 heteroatoms chosen from O, S and N, or a salt or isomer thereof described especially in patent application FR-A-2 892 303.

The silicone bis-urea derivatives of general formula (I) or a salt and/or isomer thereof:

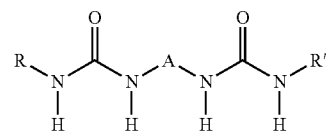

(I)

in which:

A is a group of formula (II):

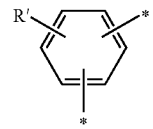

with $R_1$ being a linear or branched $C_1$-$C_4$ alkyl radical, and the *s symbolizing the points of attachment of the group A to each of the two nitrogen atoms of the rest of the compound of general formula (I), and R and R', which may be identical or different, are chosen from:
i) the radicals of formula (III):

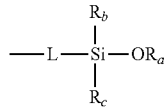
(III)

in which:

L is a single bond or a divalent carbon-based radical, especially a linear, branched and/or cyclic, saturated or unsaturated hydrocarbon-based radical (alkylene), containing 1 to 18 carbon atoms, and possibly comprising 1 to 4 heteroatoms chosen from N, O and S;

$R_a$ is:

a) a carbon-based radical, especially a linear, branched and/or cyclic, saturated or unsaturated hydrocarbon-based radical (alkyl), containing 1 to 18 carbon atoms, and possibly comprising 1 to 8 heteroatoms chosen from N, O, Si and S; or b) a silicone radical of formula:

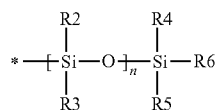

with n being between 0 and 100, especially between 1 and 80, or even 2 to 20;

and $R_2$ to $R_6$ being, independently of each other, carbon-based radicals, especially linear or branched hydrocarbon-based radicals (alkyl) containing 1 to 12 and especially 1 to 6 carbon atoms, and possibly comprising 1 to 4 heteroatoms, especially O;

$R_b$ and $R_c$ are, independently of each other, chosen from:

a) carbon-based radicals, especially linear, branched and/or cyclic, saturated or unsaturated hydrocarbon-based radicals (alkyl), containing 1 to 18 carbon atoms, and possibly comprising 1 to 4 heteroatoms chosen from N, O, Si and S;

b) the radicals of formula:

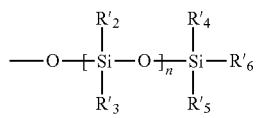

with n being between 0 and 100, especially between 1 and 80, or even 2 to 20;

and $R'_2$ to $R'_6$ being, independently of each other, carbon-based radicals, especially linear or branched hydrocarbon-based radicals (alkyl), containing 1 to 12 and especially 1 to 6 carbon atoms, and possibly comprising 1 to 4 heteroatoms, especially O; and ii) linear, branched and/or cyclic, saturated or unsaturated $C_1$-$C_{30}$ alkyl radicals, optionally comprising 1 to 3 heteroatoms chosen from O, S, F and N;

it being understood that at least one of the radicals R and/or R' is of formula (III), such as those described in patent application FR-A-2 900 819.

The bis-urea derivatives described in patent application FR-A-28994476.

Preferably, the organogelling agent of bis-urea type is silicone-based.

Thus, the compositions according to the invention may comprise from 0.01% to 20% by weight, especially from 0.05% to 15% by weight, or even from 0.1% to 10% by weight, better still from 1% to 8% by weight and even better still from 2% to 5% by weight of organogelling agents, for instance bis-urea compounds, relative to the total weight of the composition.

It is clear that this effective amount can vary significantly depending, inter alia, on the nature of the bis-urea derivative compound, on whether it is used in pure form or as a mixture with other bis-urea derivatives, and on the nature of the liquid fatty phase.

The mixture of bis-ureas is advantageously soluble at a temperature of less than or equal to 50° C., or even less than or equal to 30° C., and especially at room temperature, in the liquid fatty phase to be texturized.

According to one preferred embodiment, the composition according to the invention also comprises at least one additive chosen from volatile oils, non-volatile oils, dyestuffs, pasty fatty substances, waxes and fillers, and a mixture thereof.

Dyestuffs

The composition according to the invention preferably comprises at least one dyestuff, preferably in a content of at least 0.1% by weight relative to the total weight of the composition. The dyestuff may be chosen from pulverulent dyestuffs (especially pigments and nacres), and water-soluble or liposoluble dyestuffs.

For the purposes of the invention, the term "pigments" means white or coloured, mineral or organic particles, which are insoluble in an aqueous solution, and which are intended to colour and/or opacify the resulting makeup film. The pigments also include nacres or nacreous pigments.

The pigments may be present in a proportion of from 0.1% to 15% by weight, especially from 1% to 10% by weight and in particular from 2% to 8% by weight relative to the total weight of the cosmetic composition.

As mineral pigments that may be used in the invention, mention may be made of titanium oxide, zirconium oxide or cerium oxide, and also zinc oxide, iron oxide or chromium oxide, ferric blue, manganese violet, ultramarine blue and chromium hydrate.

According to one embodiment, titanium oxides and iron oxides are more particularly considered in the invention.

According to one embodiment, a pigment that is suitable for use in the invention may in particular be based on titanium dioxide and iron oxide.

It may also be a pigment with a structure that may be, for example, of sericite/brown iron oxide/titanium dioxide/silica type. Such a pigment is sold, for example, under the reference Coverleaf NS or JS by the company Chemicals and Catalysts, and has a contrast ratio in the region of 30.

A pigment that is suitable for use in the invention may comprise a structure that may be, for example, of silica microsphere type containing iron oxide. An example of a pigment having this structure is the product sold by the company Miyoshi under the reference PC Ball PC-LL-100 P, this pigment consisting of silica microspheres containing yellow iron oxide.

Among the organic pigments that may be used in the invention, mention may be made of carbon black, pigments of D&C type, lakes based on cochineal carmine or on barium, strontium, calcium or aluminium, or alternatively the diketopyrrolopyrroles (DPP) described in documents EP-A-542 669, EP-A-787 730, EP-A-787 731 and WO-A-96/08537.

The terms "nacres" and "nacreous pigments" should be understood as meaning iridescent or non-iridescent coloured particles of any form, especially produced by certain molluscs in their shell, or else synthesized, and which have a colour effect by optical interference.

The nacres may be chosen from nacreous pigments such as titanium mica coated with an iron oxide, titanium mica coated with bismuth oxychloride, titanium mica coated with chromium oxide, titanium mica coated with an organic dye and also nacreous pigments based on bismuth oxychloride. They may also be mica particles at the surface of which are superposed at least two successive layers of metal oxides and/or of organic dyestuffs.

Examples of nacres that may also be mentioned include natural mica coated with titanium oxide, with iron oxide, with natural pigment or with bismuth oxychloride.

Among the nacres available on the market, mention may be made of the mica-based nacres Timica, Flamenco and Duochrome sold by the company Engelhard, the Timiron nacres sold by the company Merck, the Prestige mica-based nacres, sold by the company Eckart, and the Sunshine synthetic mica-based nacres, sold by the company Sun Chemical.

The nacres may more particularly have a yellow, pink, red, bronze, orangey, brown, gold and/or coppery colour or tint.

As illustrations of nacres that may be used in the context of the present invention, mention may be made especially of the gold-coloured nacres sold especially by the company Engelhard under the name Brilliant gold 212G (Timica), Gold 222C (Cloisonne), Sparkle gold (Timica), Gold 4504 (Chromalite) and Monarch gold 233X (Cloisonne); the bronze nacres sold especially by the company Merck under the name Bronze fine (17384) (Colorona) and Bronze (17353) (Colorona) and by the company Engelhard under the name Super bronze (Cloisonne); the orange nacres sold especially by the company Engelhard under the name Orange 363C (Cloisonne) and Orange MCR 101 (Cosmica) and by the company Merck under the name Passion orange (Colorona) and Matte orange (17449) (Microna); the brown nacres sold especially by the company Engelhard under the name Nu-antique copper 340XB (Cloisonne) and Brown CL4509 (Chromalite); the nacres with a copper tint sold especially by the company Engelhard under the name Copper 340A (Timica); the nacres with a red tint sold especially by the company Merck under the name Sienna fine (17386) (Colorona); the nacres with a yellow tint sold especially by the company Engelhard under the name Yellow (4502) (Chromalite); the red nacres with a gold tint sold especially by the company Engelhard under the name Sunstone G012 (Gemtone); the pink nacres sold especially by the company Engelhard under the name Tan opale G005 (Gemtone); the black nacres with a gold tint sold especially by the company Engelhard under the name Nu antique bronze 240 AB (Timica), the blue nacres sold especially by the company Merck under the name Matte blue (17433) (Microna), the white nacres with a silvery tint sold especially by the company Merck under the name Xirona Silver, and the golden-green pink-orange nacres sold especially by the company Merck under the name Indian summer (Xirona), and mixtures thereof.

According to one embodiment variant, a composition of the invention may comprise as pigments a pigment chosen from titanium dioxide, pigments based on titanium dioxide and iron oxide, or pigments based on titanium dioxide, for instance sericite/brown iron oxide/titanium dioxide/silica, or natural mica coated with titanium oxide, and mixtures thereof.

A composition according to the invention may also comprise at least one dyestuff different from the pigments as defined above.

Such a dyestuff may be chosen from organic or inorganic, liposoluble or water-soluble dyestuffs, and materials with a specific optical effect, and mixtures thereof.

A cosmetic composition according to the invention may thus also comprise water-soluble or liposoluble dyes. The liposoluble dyes are, for example, Sudan red, DC Red 17, DC Green 6, β-carotene, Sudan brown, DC Yellow 11, DC Violet 2, DC Orange 5 and quinoline yellow. The water-soluble dyes are, for example, beetroot juice or methylene blue.

A cosmetic composition according to the invention may also contain at least one material with a specific optical effect.

This effect is different than a simple conventional hue effect, i.e. a unified and stabilized effect as produced by standard dyestuffs, for instance monochromatic pigments. For the purposes of the invention, the term "stabilized" means lacking an effect of variability of the colour as a function of the angle of observation or alternatively in response to a temperature change.

For example, this material may be chosen from particles with a metallic tint, goniochromatic colouring agents, diffracting pigments, thermochromic agents, optical brighteners, and also fibres, especially interference fibres.

The particles with a metallic tint that may be used in the invention are chosen in particular from:
particles of at least one metal and/or of at least one metal derivative,
particles comprising a mono-material or multi-material organic or mineral substrate, at least partially coated with at least one coat with a metallic tint comprising at least one metal and/or at least one metal derivative, and mixtures of the said particles.

Among the metals that may be present in the said particles, mention may be made, for example, of Ag, Au, Cu, Al, Ni, Sn, Mg, Cr, Mo, Ti, Zr, Pt, Va, Rb, W, Zn, Ge, Te and Se, and mixtures or alloys thereof. Ag, Au, Cu, Al, Zn, Ni, Mo and Cr and mixtures or alloys thereof (for example bronzes and brasses) are preferred metals.

The term "metal derivatives" is intended to denote compounds derived from metals, especially oxides, fluorides, chlorides and sulfides.

As illustrations of these particles, mention may be made of aluminium particles, such as those sold under the names Starbrite 1200 EAC® by the company Siberline, and Metalure® by the company Eckart.

Mention may also be made of copper metal powders or alloy mixtures such as the reference 2844 sold by the company Radium Bronze, metallic pigments such as aluminium or bronze, such as those sold under the name Rotosafe 700 from the company Eckart, the silica-coated aluminium particles sold under the name Visionaire Bright Silver from the company Eckart and metal alloy particles, for instance the silica-coated bronze (alloy of copper and zinc) powders sold under the name Visionaire Bright Natural Gold from the company Eckart.

They may also be particles comprising a glass substrate, such as those sold by the company Nippon Sheet Glass under the name Microglass Metashine.

The goniochromatic colouring agent may be chosen, for example, from multilayer interference structures and liquid-crystal colouring agents.

Examples of symmetrical multilayer interference structures that may be used in the compositions prepared in accordance with the invention are, for example, the following structures: Al/SiO$_2$/Al/SiO$_2$/Al, pigments having this structure being sold by the company Dupont de Nemours; Cr/MgF$_2$/Al/MgF$_2$/Cr, pigments having this structure being sold under the name Chromaflair by the company Flex; MoS$_2$/SiO$_2$/Al/SiO$_2$/MoS$_2$; Fe$_2$O$_3$/SiO$_2$/Al/SiO$_2$/Fe$_2$O$_3$, and Fe$_2$O$_3$/SiO$_2$/Fe$_2$O$_3$/SiO$_2$/Fe$_2$O$_3$, pigments having these structures being sold under the name Sicopearl by the company BASF; MoS$_2$/SiO$_2$/mica-oxide/SiO$_2$/MoS$_2$; Fe$_2$O$_3$/SiO$_2$/mica-oxide/SiO$_2$/Fe$_2$O$_3$; TiO$_2$/SiO$_2$/TiO$_2$ and TiO$_2$/Al$_2$O$_3$/TiO$_2$; SnO/TiO$_2$/SiO$_2$/TiO$_2$/SnO; Fe$_2$O$_3$/SiO$_2$/Fe$_2$O$_3$; SnO/mica/TiO$_2$/SiO$_2$/TiO$_2$/mica/SnO, pigments having these structures being sold under the name Xirona by the company Merck (Darmstadt). By way of example, these pigments may be the pigments of silica/titanium oxide/tin oxide structure sold under the name Xirona Magic by the company Merck, the pigments of silica/brown iron oxide structure sold under the name Xirona Indian Summer by the company Merck and the pigments of silica/titanium oxide/mica/tin oxide structure sold under the name Xirona Caribbean Blue by the company Merck. Mention may also be made of the Infinite Colors pigments from the company Shiseido. Depending on the thickness and the nature of the various layers, different effects are obtained. Thus, with the Fe$_2$O$_3$/SiO$_2$/Al/SiO$_2$/Fe$_2$O$_3$ structure, the colour changes from green-golden to red-gray for SiO$_2$ layers of 320 to 350 nm; from red to golden for SiO$_2$ layers of 380 to 400 nm; from violet to green for SiO$_2$ layers of 410 to 420 nm; from copper to red for SiO$_2$ layers of 430 to 440 nm.

Examples of pigments with a polymeric multilayer structure that may be mentioned include those sold by the company 3M under the name Color Glitter.

Examples of liquid-crystal goniochromatic particles that may be used include those sold by the company Chenix and also the product sold under the name Helicone® HC by the company Wacker.

The dyestuffs, in particular the pigments treated with a hydrophobic agent, may be present in the composition in a content ranging from 0.1% to 50% by weight, preferably ranging from 0.5% to 30% by weight and preferentially ranging from 1% to 20% by weight relative to the total weight of the composition.

Liquid Fatty Phase

According to one preferred embodiment, the composition comprises a liquid fatty phase comprising at least one oil.

The term "oil" means a non-aqueous compound, which is liquid at room temperature (25° C.) and atmospheric pressure (760 mmHg).

Volatile Oil

The composition according to the invention may comprise at least one volatile oil.

For the purposes of the invention, a volatile oil has, at room temperature (25° C.) and atmospheric pressure (760 mmHg), a vapour pressure ranging from 0.02 mmHg to 300 mmHg (2.66 Pa to 40 000 Pa) and better still ranging from 0.1 to 90 mmHg (13 Pa to 12 000 Pa). Non-volatile oils then correspond to a vapour pressure below 0.02 mmHg (2.66 Pa) and better still below $10^{-3}$ mmHg (0.13 Pa).

The volatile oil may be a silicone oil, a hydrocarbon-based oil or a fluoro oil.

a. Silicone Oil

According to one variant of the invention, the liquid fatty phase comprises at least one volatile silicone oil.

The term "silicone oil" means an oil comprising at least one silicon atom, especially comprising Si—O groups.

The volatile silicone oil that may be used in the invention may be chosen from silicone oils with a flash point ranging from 40° C. to 150° C., preferably with a flash point of greater than 55° C. and less than or equal to 105° C., and preferentially ranging from 65° C. to 95° C. The flash point is measured in particular according to standard ISO 3679.

The volatile silicone oil may be chosen from linear or cyclic silicone oils such as linear or cyclic polydimethylsiloxanes (PDMS) containing from 3 to 7 silicon atoms.

Examples of such oils that may be mentioned include octyl trimethicone, hexyl trimethicone, decamethylcyclopentasiloxane (cyclopentasiloxane or D5), octamethylcyclotetrasiloxane (cyclotetradimethyl-siloxane or D4), dodecamethylcyclohexasiloxane (D6), decamethyltetrasiloxane (L4), KF 96 A from Shin-Etsu, and polydimethylsiloxanes such as those sold under the references DC 200 (1.5 cSt), DC 200 (5 cSt) and DC 200 (3 cSt) by Dow Corning.

b. Hydrocarbon-based Oil

According to one variant of the invention, the liquid fatty phase comprises at least one volatile hydrocarbon-based oil.

The term "hydrocarbon-based oil" means an oil formed essentially from, or even constituted by, carbon and hydrogen atoms, and optionally oxygen and nitrogen atoms, and not containing any silicon or fluorine atoms. It may contain alcohol, ester, ether, carboxylic acid, amine and/or amide groups.

The volatile hydrocarbon-based oils (also known as solvents) may be chosen from hydrocarbon-based oils containing from 8 to 16 carbon atoms, especially branched C8-C16 alkanes such as C8-C16 isoalkanes of petroleum origin (also known as isoparaffins), for instance isododecane (also known as 2,2,4,4,6-pentamethylheptane), isodecane, isohexadecane and, for example, the oils sold under the trade names Isopar and Permethyl, branched C8-C16 esters and isohexyl neopentanoate, and mixtures thereof. Other volatile hydrocarbon-based oils, for instance petroleum distillates, especially those sold under the name Shell Solt by the company Shell, may also be used. Preferably, the volatile solvent is chosen from volatile hydrocarbon-based oils containing from 8 to 16 carbon atoms, and mixtures thereof.

As other volatile hydrocarbon-based solvents (oils) that may be used in the composition according to the invention, mention may also be made of ketones that are liquid at room temperature, such as methyl ethyl ketone or acetone; short-chain esters (containing from 3 to 8 carbon atoms in total) such as ethyl acetate, methyl acetate, propyl acetate or n-butyl acetate; ethers that are liquid at room temperature, such as diethyl ether, dimethyl ether or dichlorodiethyl ether; alcohols and especially linear or branched lower monoalcohols containing from 2 to 5 carbon atoms, such as ethanol, isopropanol or n-propanol.

Preferably, the composition has a volatile oil content of greater than 5% by weight, preferably ranging from 5% to 50% by weight and better still ranging from 10% to 35% by weight relative to the total weight of the composition.

According to one preferred embodiment, the volatile oil has a flash point of greater than 65° C. and better still greater than 80° C. An example of such a volatile oil that may be mentioned is isohexadecane.

Non-volatile Oils

The composition according to the invention may comprise at least one non-volatile oil. This oil may be chosen in particular from non-volatile hydrocarbon-based oils and/or silicone oils and/or fluoro oils, and preferably from hydrocarbon-based oils.

The term "non-volatile oil" means an oil that remains on the skin or the keratin fibre, more generally on keratin materials, at room temperature and atmospheric pressure, for at least several hours and that especially has a vapour pressure of less than $10^{-3}$ mmHg (0.13 Pa). A non-volatile oil may also be defined as having an evaporation rate such that, under the conditions defined previously, the amount evaporated after 30 minutes is less than 0.07 mg/cm².

These oils may be of plant, mineral or synthetic origin.

Non-volatile hydrocarbon-based oils that may especially be mentioned include:

- hydrocarbon-based oils of plant origin such as triglycerides formed from fatty acid esters of glycerol, the fatty acids of which may have chain lengths ranging from $C_4$ to $C_{24}$, these chains possibly being linear or branched, and saturated or unsaturated, for instance heptanoic or octanoic acid triglycerides; these oils are especially wheatgerm oil, sunflower oil, grapeseed oil, sesame seed oil, corn oil, apricot oil, castor oil, Shea oil, avocado oil, olive oil, soybean oil, sweet almond oil, palm oil, rapeseed oil, cottonseed oil, hazelnut oil, macadamia oil, jojoba oil, alfalfa oil, poppy oil, pumpkin oil, sesame oil, marrow oil, rapeseed oil, blackcurrant oil, evening primrose oil, millet oil, barley oil, quinoa oil, rye oil, safflower oil, candlenut oil, passion flower oil or musk rose oil; or alternatively caprylic/capric acid triglycerides, for instance those sold by the company Stearineries Dubois or those sold under the names Miglyol 810®, 812® and 818® by the company Dynamit Nobel, synthetic ethers;
- linear or branched hydrocarbons of mineral or synthetic origin, such as liquid paraffin or derivatives thereof, petroleum jelly, hydrogenated polyisobutene such as Parleam® sold by the company Nippon Oil Fats, squalane, polybutylenes such as Indopol H-100 (of molar mass or MW=965 g/mol), Indopol H-300 (MW=1340 g/mol) or Indopol H-1500 (MW=2160 g/mol) sold or manufactured by the company Amoco, hydrogenated polyisobutylenes such as Panalane H-300 E sold or manufactured by Amoco (MW=1340 g/mol), Viseal 20000 sold or manufactured by the company Synteal (MW=6000 g/mol) and Rewopal PIB 1000 sold or manufactured by the company Witco (MW=1000 g/mol), polydecenes and hydrogenated polydecenes such as: Puresyn 10 (MW=723 g/mol) and Puresyn 150 (MW=9200 g/mol) sold or manufactured by the company Mobil Chemicals, and mixtures thereof;
- fatty acid esters, in particular of 4 to 22 carbon atoms, and especially of octanoic acid, heptanoic acid, lanolic acid, oleic acid, lauric acid or stearic acid, for instance propylene glycol dioctanoate, propylene glycol monoisostearate, poly-2-glyceryl diisostearate or neopentyl glycol diheptanoate,
- synthetic esters, for instance the oils of formula $R_1COOR_2$ in which $R_1$ represents a linear or branched fatty acid residue comprising from 1 to 40 carbon atoms and $R_2$ represents a hydrocarbon-based chain, which is especially branched, containing from 1 to 40 carbon atoms, on condition that $R_1+R_2 \geq 11$, for instance Purcellin oil (cetostearyl octanoate), isononyl isononanoate, $C_{12}$ to $C_{15}$ alkyl benzoates, 2-ethylhexyl palmitate, 2-octyldodecyl stearate, 2-octyldodecyl erucate, isostearyl isostearate, 2-octyldodecyl benzoate, alcohol or polyalcohol octanoates, decanoates or ricinoleates, isopropyl myristate, isopropyl palmitate, butyl stearate, hexyl laurate, 2-ethylhexyl palmitate, 2-hexyldecyl laurate, 2-octyldecyl palmitate, 2-octyldodecyl myristate or isodecyl neopentanoate;
- hydroxylated esters, for instance isostearyl lactate, octyl hydroxystearate, octyldodecyl hydroxystearate, diisostearyl malate, triisocetyl citrate, glyceryl or diglyceryl triisostearate; diethylene glycol diisononanoate; and pentaerythritol esters, such as pentaerythrityl tetrakis(2-decyl)tetradecanoate (MW=1538 g/mol), pentaerythrityl tetraisostearate (MW=1202 g/mol) and pentaerythrityl tetraisononanoate (MW=697 g/mol);
- esters of aromatic acids and of alcohols comprising 4 to 22 carbon atoms, especially tridecyl trimellitate;
- a polyester resulting from the esterification of at least one hydroxylated carboxylic acid triglyceride with an aliphatic monocarboxylic acid and with an aliphatic dicarboxylic acid, which is optionally unsaturated, such as the castor oil of succinic acid and of isostearic acid sold under the reference Zenigloss by Zenitech,
- esters of a diol dimer and of a diacid dimer of general formula HO—$R^1$—(—OCO—$R^2$—COO—$R^1$—)$_h$—OH in which:

$R^1$ represents a diol dimer obtained by hydrogenation of dilinoleic diacid, $R^2$ represents a hydrogenated dilinoleic diacid residue, and h represents an integer ranging from 1 to 9, especially the esters of dilinoleic diacids and of dilinoleyl diol dimers sold by the company Nippon Fine Chemical under the trade names Lusplan DD-DA5 and DD-DA7®,
- vinylpyrrolidone/1-hexadecene copolymers, for example sold under the name Antaron V-216 by the company ISP (MW=7300 g/mol),
- fatty alcohols that are liquid at room temperature, with a branched and/or unsaturated carbon-based chain containing from 8 to 26 carbon atoms, for instance oleyl alcohol, linolenyl alcohol, linolenyl alcohol, isostearyl alcohol or octyldodecanol;
- $C_8$-$C_{26}$ higher fatty acids such as oleic acid, linoleic acid, linolenic acid or isostearic acid;
- and mixtures thereof.

The non-volatile silicone oils that may be used in the composition according to the invention may be silicone oils such as phenyl silicone oils, for instance trimethylsiloxyphenyl dimethicone sold under the reference Belsil PDM 1000 from the company Wacker (MW=9000 g/mol) or 1,3,5-trimethyl-1,1,3,5,5-pentaphenyltrisiloxane sold by the company Dow Corning under the reference PH-1555 HRI (INCI name: trimethyl pentaphenyl trisiloxane), phenyl trimethicones (such as the phenyl trimethicone sold under the trade name DC556 by Dow Corning), phenyl dimethicones, phenyltrimethylsiloxydiphenylsiloxanes, diphenyl dimethicones, diphenylmethyldiphenyltrisiloxanes, non-volatile polydimethylsiloxanes (PDMS), and polydimethylsiloxanes comprising alkyl or alkoxy groups, which are pendent and/or at the end of a silicone chain, these groups each containing from 2 to 24 carbon atoms.

Preferably, the composition according to the invention comprises at least one silicone oil, which is preferably non-volatile.

Preferably, the non-volatile oil may be present in a content ranging from 0.1% to 60% by weight, especially ranging from 0.5% to 50% by weight and in particular ranging from 1% to 40% by weight relative to the total weight of the composition.

Besides the oils described previously, the fatty phase may also comprise at least one fatty substance that is not liquid at room temperature (25° C.) and at atmospheric pressure, known as a solid fatty substance, chosen from waxes and pasty fatty substances.

Solid Fatty Substances

Preferably, the composition according to the invention comprises at least one solid fatty substance chosen from waxes and pasty fatty substances, and a mixture thereof.

Pasty Fatty Substances

For the purposes of the present invention, the term "pasty fatty substance" (also known as a paste) means a lipophilic fatty compound with a reversible solid/liquid change of state, displaying anisotropic crystal organization in the solid state, and comprising a liquid fraction and a solid fraction at a temperature of 23° C.

In other words, the starting melting point of the pasty compound can be less than 23° C. The liquid fraction of the pasty compound measured at 23° C. can represent 9% to 97% by weight of the compound. This liquid fraction at 23° C. preferably represents between 15% and 85% and more preferably between 40% and 85% by weight.

For the purposes of the invention, the melting point corresponds to the temperature of the most endothermic peak observed on thermal analysis (DSC) as described in standard ISO 11357-3; 1999. The melting point of a paste or wax can be measured by means of a differential scanning calorimeter (DSC), for example the calorimeter sold under the name MDSC 2920 by the company TA Instruments.

The measuring protocol is as follows:

A sample of 5 mg of paste or wax (depending on the case) placed in a crucible is subjected to a first temperature rise passing from −20° C. to 100° C., at the heating rate of 10° C./minute, then is cooled from 100° C. to −20° C. at a cooling rate of 10° C./minute and finally subjected to a second temperature rise passing from −20° C. to 100° C. at a heating rate of 5° C./minute. During the second temperature rise, the variation in the difference between the power absorbed by the empty crucible and the crucible containing the sample of wax as a function of the temperature is measured. The melting point of the compound is the temperature value corresponding to the top of the peak of the curve representing the variation in the difference in power absorbed as a function of the temperature.

The liquid fraction by weight of the pasty compound at 23° C. is equal to the ratio of the enthalpy of fusion consumed at 23° C. to the enthalpy of fusion of the pasty compound.

The enthalpy of fusion of the pasty compound is the enthalpy consumed by the compound in order to pass from the solid state to the liquid state. The pasty compound is said to be in the solid state when all of its mass is in crystalline solid form. The pasty compound is said to be in the liquid state when all of its mass is in liquid form.

The enthalpy of fusion of the pasty compound is equal to the area under the curve of the thermogram obtained by means of a differential scanning calorimeter (DSC) such as the calorimeter sold under the name MDSC 2920 by the company TA Instruments, with a temperature rise of 5 or 10° C. per minute, in accordance with standard ISO 11357-3; 1999. The enthalpy of fusion of the pasty compound is the amount of energy required to make the compound pass from the solid state to the liquid state. It is expressed in J/g.

The enthalpy of fusion consumed at 23° C. is the amount of energy absorbed by the sample in order to pass from the solid state to the state it displays at 23° C. formed from a liquid fraction and a solid fraction.

The liquid fraction of the pasty compound measured at 32° C. preferably represents from 30% to 100% by weight of the compound, preferably from 50% to 100%, more preferably from 60% to 100% by weight of the compound. When the liquid fraction of the pasty compound measured at 32° C. is equal to 100%, the temperature of the end of the melting range of the pasty compound is less than or equal to 32° C.

The liquid fraction of the pasty compound measured at 32° C. is equal to the ratio of the enthalpy of fusion consumed at 32° C. to the enthalpy of fusion of the pasty compound. The enthalpy of fusion consumed at 32° C. is calculated in the same way as the enthalpy of fusion consumed at 23° C.

The pasty compound is preferably chosen from synthetic compounds and compounds of plant origin. A pasty compound may be obtained by synthesis starting from starting materials of plant origin.

The pasty compound is advantageously chosen from:
lanolin and derivatives thereof,
polyol ethers chosen from pentaerythrityl ethers of polyalkylene glycols, fatty alkyl ethers of sugars, and mixtures thereof, pentaerythrityl ether of polyethylene glycol comprising 5 oxyethylene units (5 OE) (CTFA name: PEG-5 pentaerythrityl ether), pentaerythrityl ether of polypropylene glycol comprising 5 oxypropylene units (5 OP) (CTFA name: PPG-pentaerythrityl ether), and mixtures thereof, and more especially the mixture PEG-5 pentaerythrityl ether, PPG-5 pentaerythrityl ether and soybean oil, sold under the name Lanolide by the company Vevy, in which mixture the constituents are in a 46/46/8 weight ratio: 46% of PEG-5 pentaerythrityl ether, 46% of PPG-5 pentaerythrityl ether and 8% of soybean oil,
polymeric or non-polymeric silicone compounds,
polymeric or non-polymeric fluoro compounds,
vinyl polymers, especially:
 olefin homopolymers and copolymers,
 hydrogenated diene homopolymers and copolymers,
 linear or branched homopolymer or copolymer oligomers of alkyl (meth)acrylates preferably containing a $C_8$-$C_{30}$ alkyl group,
 homopolymer and copolymer oligomers of vinyl esters containing $C_8$-$C_{30}$ alkyl groups,
 vinylpyrrolidone/eicosene copolymers (INCI name VP/eicosene copolymer), for example the product sold by the company ISP under the trade name Ganex V220F®,
 homopolymer and copolymer oligomers of vinyl ethers containing $C_8$-$C_{30}$ alkyl groups,
liposoluble polyethers resulting from polyetherification between one or more $C_2$-$C_{100}$ and preferably $C_2$-$C_{50}$ diols,
esters,
and/or mixtures thereof.

The pasty compound is preferably a polymer, especially a hydrocarbon-based polymer.

Among the liposoluble polyethers, copolymers of ethylene oxide and/or of propylene oxide with $C_6$-$C_{30}$-long-chain alkylene oxides, more preferably such that the weight ratio of the ethylene oxide and/or propylene oxide to the alkylene oxides in the copolymer is from 5/95 to 70/30, are particularly preferred. In this family, mention will be made especially of copolymers such that the long-chain alkylene oxides are arranged in blocks with an average molecular weight from 1000 to 000, for example a polyoxyethylene/polydodecyl glycol block copolymer, such as the ethers of dodecanediol (22 mol) and of polyethylene glycol (45 OE) sold under the brand name Elfacos ST9 by Akzo Nobel.

Among the esters, the following are especially preferred:
esters of a glycerol oligomer, especially diglycerol esters, in particular condensates of adipic acid and of glycerol, for which some of the hydroxyl groups of the glycerols have reacted with a mixture of fatty acids such as stearic acid, capric acid, stearic acid and isostearic acid, and 12-hydroxystearic acid, especially the product sold under the brand name Softisan 649 by the company Sasol, arachidyl propionate sold under the brand name Waxenol 801 by Alzo, phytosterol esters, fatty acid triglycerides and derivatives thereof, pentaerythritol esters, non-crosslinked polyesters resulting from polycondensation between a linear or branched $C_4$-$C_{50}$ dicarboxylic acid or polycarboxylic acid and a $C_2$-$C_{50}$ diol or polyol, aliphatic esters of an ester resulting from the esterification of an aliphatic hydroxycarboxylic acid ester with an aliphatic carboxylic acid. Preferably, the aliphatic carboxylic acid comprises from 4 to 30 and preferably from 8 to 30 carbon atoms. It is preferably chosen from hexanoic acid, heptanoic acid, octanoic acid, 2-ethylhexanoic acid, nonanoic acid, decanoic acid, undecanoic acid, dodecanoic acid, tridecanoic acid, tetradecanoic acid, pentadecanoic acid, hexadecanoic acid, hexyldecanoic acid, heptadecanoic acid, octadecanoic acid, isostearic acid, nonadecanoic acid, eicosanoic acid, isoarachidic acid, octyldodecanoic acid, heneicosanoic acid and docosanoic acid, and mixtures thereof. The aliphatic carboxylic acid is preferably branched. The aliphatic hydroxycarboxylic acid ester is advantageously derived from a hydroxylated aliphatic carboxylic acid containing from 2 to 40 carbon atoms, preferably from 10 to 34 carbon atoms and better still from 12 to 28 carbon atoms, and from 1 to 20 hydroxyl groups, preferably from 1 to 10 hydroxyl groups and better still from 1 to 6 hydroxyl groups. The aliphatic hydroxycarboxylic acid ester is chosen from:

a) partial or total esters of saturated linear monohydroxylated aliphatic monocarboxylic acids;

b) partial or total esters of unsaturated mono-hydroxylated aliphatic monocarboxylic acids;

c) partial or total esters of saturated mono-hydroxylated aliphatic polycarboxylic acids;

d) partial or total esters of saturated poly-hydroxylated aliphatic polycarboxylic acids;

e) partial or total esters of $C_2$ to $C_{16}$ aliphatic polyols that have reacted with a monohydroxylated or polyhydroxylated aliphatic monocarboxylic or poly-carboxylic acid, and mixtures thereof;

esters of a diol dimer and of a diacid dimer, where appropriate esterified on their free alcohol or acid function(s) with acid or alcohol radicals, especially dimer dilinoleate esters; such esters may be chosen especially from the esters having the following INCI nomenclature: bis-behenyl/isostearyl/phytosteryl dimerdilinoleyl dimerdilinoleate (Plandool G), phytosteryl/isosteryl/stearyl/behenyl dimerdilinoleate (Plandool H or Plandool S), and mixtures thereof;

hydrogenated rosinate esters, such as dilinoleyl dimers of hydrogenated rosinate (Lusplan DD-DHR or DD-DHR from Nippon Fine Chemical);

and mixtures thereof.

Advantageously, the pasty compound(s) preferably represent 0.1% to 80%, better still 0.5% to 60%, better still 1% to 30% and even better still 1% to 20% by weight relative to the total weight of the composition.

Waxes:

According to one preferred embodiment, the composition according to the invention comprises at least one wax.

The wax under consideration in the context of the present invention is generally a lipophilic compound that is solid at room temperature (25° C.), with a solid/liquid reversible change of state, having a melting point of greater than or equal to 30° C., which may be up to 200° C. and in particular up to 120° C.

In particular, the waxes that are suitable for the invention may have a melting point of greater than or equal to 45° C. and in particular greater than or equal to 55° C.

The waxes that may be used in the compositions according to the invention are chosen from waxes that are solid at room temperature, of animal, plant, mineral or synthetic origin, and mixtures thereof.

As illustrations of waxes that are suitable for use in the invention, mention may be made especially of hydrocarbon-based waxes, for instance beeswax, lanolin wax and Chinese insect waxes, rice bran wax, carnauba wax, candelilla wax, ouricury wax, alfalfa wax, berry wax, shellac wax, Japan wax and sumach wax; montan wax, orange wax and lemon wax, microcrystalline waxes, paraffins and ozokerite; polyethylene waxes, the waxes obtained by Fisher-Tropsch synthesis, and waxy copolymers, and also esters thereof.

Mention may also be made of the waxes obtained by catalytic hydrogenation of animal or plant oils with linear or branched $C_8$-$C_{32}$ fatty chains. Among these, mention may be made especially of isomerized jojoba oil such as the trans-isomerized partially hydrogenated jojoba oil manufactured or sold by the company Desert Whale under the trade reference Iso-Jojoba-50°, hydrogenated sunflower oil, hydrogenated castor oil, hydrogenated coconut oil, hydrogenated lanolin oil, and the bis(1,1,1-trimethylolpropane) tetrastearate sold under the name Hest 2T-4S® by the company Heterene.

Mention may also be made of silicone waxes ($C_{30\text{-}45}$ Alkyl Dimethicone) and fluoro waxes.

It is also possible to use the waxes obtained by hydrogenation of castor oil esterified with cetyl alcohol, sold under the names Phytowax Ricin 16L64® and 22L73® by the company Sophim. Such waxes are described in patent application FR-A-2 792 190.

It is possible to use a $C_{20}$-$C_{40}$ alkyl (hydroxystearyloxy) stearate (the alkyl group comprising from 20 to 40 carbon atoms) as wax, alone or as a mixture. Such a wax is sold especially under the names Kester Wax K 82 P®, Hydroxypolyester K 82 P® and Kester Wax K 80 P® by the company Koster Keunen.

As microwaxes that may be used in the compositions according to the invention, mention may be made especially of carnauba microwaxes such as the product sold under the name MicroCare 350° by the company Micro Powders, synthetic microwaxes such as the product sold under the name MicroEase 114S° by the company Micro Powders, microwaxes formed from a mixture of carnauba wax and polyethylene wax, such as those sold under the names MicroCare 300° and 310® by the company Micro Powders, microwaxes formed from a mixture of carnauba wax and synthetic wax, such as the product sold under the name MicroCare 325® by the company Micro Powders, polyethylene microwaxes such as those sold under the names Micropoly 200®, 220®, 220L® and 250S° by the company Micro Powders, and polytetrafluoroethylene microwaxes such as those sold under the names Microslip 519® and 519 L® by the company Micro Powders.

The composition according to the invention may comprise a wax content ranging from 0.1% to 30% by weight, in particular from 0.5% to 20% and more particularly from 1% to 15% by weight relative to the total weight of the composition.

Additional Film-forming Polymer

Besides the copolymer described previously, the composition may comprise an additional polymer such as a film-forming polymer.

According to the present invention, the term "film-forming polymer" means a polymer that is capable of forming, by itself or in the presence of an auxiliary film-forming agent, a continuous deposit on a support, especially on keratin materials.

Among the film-forming polymers that may be used in the composition of the present invention, mention may be made of synthetic polymers, of radical type or of polycondensate type, polymers of natural origin, and mixtures thereof. Film-forming polymers that may be mentioned in particular include acrylic polymers, polyurethanes, polyesters, polyamides, polyureas and cellulose-based polymers, for instance nitrocellulose.

The polymer may be combined with one or more auxiliary film-forming agents. Such a film-forming agent may be chosen from any compound known to those skilled in the art as being capable of fulfilling the desired function, and may be chosen especially from plasticizers and coalescers.

Lipophilic Gelling Agents

According to one embodiment, the composition according to the invention may comprise at least one gelling agent. The gelling agents that may be used in the compositions according to the invention may be organic or mineral, polymeric or molecular lipophilic gelling agents.

Mineral lipophilic gelling agents that may be mentioned include optionally modified clays such as hectorites modified with a $C_{10}$ to $C_{22}$ ammonium chloride, for instance hectorite modified with distearyldimethylammonium chloride, for instance the product sold under the name Bentone 38V® by the company Elementis.

Mention may also be made of optionally hydrophobic-surface-treated fumed silica with a particle size of less than 1 μm. Specifically, it is possible to chemically modify the surface of silica, via a chemical reaction that generates a reduction in the number of silanol groups present at the surface of the silica. It is especially possible to replace silanol groups with hydrophobic groups: a hydrophobic silica is then obtained. The hydrophobic groups may be:

trimethylsiloxyl groups, which are obtained especially by treating fumed silica in the presence of hexamethyldisilazane. Silicas thus treated are known as Silica silylate according to the CTFA (8th edition, 2000). They are sold, for example, under the references Aerosil R812® by the company Degussa and Cab-O-Sil TS-530® by the company Cabot, dimethylsilyloxyl or polydimethylsiloxane groups, which are especially obtained by treating fumed silica in the presence of polydimethylsiloxane or dimethyldichlorosilane. Silicas thus treated are known as Silica dimethyl silylate according to the CTFA (8th edition, 2000). They are sold, for example, under the references Aerosil R972® and Aerosil R974® by the company Degussa, and Cab-O—Sil TS-610 and Cab-O—Sil TS-720® by the company Cabot.

Among the lipophilic gelling agents that may be used in the compositions according to the invention, mention may also be made of fatty acid esters of dextrin, such as dextrin palmitates, especially those sold under the names Rheopearl TL® or Rheopearl KL® by the company Chiba Flour.

It is also possible to use silicone polyamides of the polyorganosiloxane type such as those described in documents U.S. Pat. Nos. 5,874,069, 5,919,441, 6,051,216 and 5,981,680.

These silicone polymers may belong to the following two families:

polyorganosiloxanes comprising at least two groups capable of establishing hydrogen interactions, these two groups being located in the polymer chain, and/or polyorganosiloxanes comprising at least two groups capable of establishing hydrogen interactions, these two groups being located on grafts or branches.

Fillers:

The composition according to the invention may comprise at least one filler.

For the purposes of the present invention, the term "filler" denotes solid particles of any form, which are in an insoluble form and dispersed in the medium of the composition, even at temperatures that may be up to the melting point of all the fatty substances of the composition.

Generally, the fillers used according to the invention are colourless or white, namely non-pigmentary, i.e. they are not used to give a particular colour or shade to the composition according to the invention, even though their use may inherently lead to such a result. These fillers serve especially to modify the rheology or texture of the composition.

In this respect, they are different from nacres, organic pigmentary materials, for instance carbon black, pigments of D&C type, and lakes based on cochineal carmine or on barium, strontium, calcium or aluminium, and inorganic pigmentary materials, for instance titanium dioxide, zirconium oxide or cerium oxide, and also iron oxides (black, yellow or red), chromium oxide, manganese violet, ultramarine blue, chromium hydrate and ferric blue, which are, themselves, used to give a shade and coloration to the compositions incorporating them.

For the purposes of the invention, such compounds are not covered by the definition of fillers, which thus covers non-pigmentary fillers, which may be organic or inorganic.

The non-pigmentary fillers used in the compositions according to the present invention may be of lamellar, globular or spherical form, of fibre type, or of any intermediate form between these defined forms.

The size of the particles, i.e. their granulometry, is chosen so as to ensure the good dispersion of the fillers in the composition according to the invention. The granulometry of the particles may be distributed within the range from 5 μm to 10 nm and in particular from 10 μm to 10 nm.

The fillers according to the invention may or may not be surface-coated, in particular surface-treated with silicones, amino acids, fluoro derivatives or any other substance that promotes the dispersion and compatibility of the filler in the composition.

Mineral Fillers

For the purposes of the present invention, the terms "mineral" and "inorganic" are used interchangeably.

Among the non-pigmentary mineral fillers that may be used in the compositions according to the invention, mention may be made of talc, mica, silica, perlite, which is especially commercially available from the company World Minerals Europe under the trade names Perlite P1430, Perlite P2550 or Perlite P204, kaolin, precipitated calcium carbonate, magnesium carbonate, magnesium hydrogen carbonate, hydroxyapatite, boron nitride, hollow silica microspheres (Silica Beads from Maprecos), and glass or ceramic microcapsules, and mixtures thereof.

According to one embodiment, the cosmetic composition according to the invention comprises at least one non-pigmentary mineral filler chosen from the group comprising kaolin, talc, silica, perlite and clay, and mixtures thereof.

Organic Fillers

Among the organic fillers that may be mentioned are polyamide powder (Orgasol® Nylon® from Atochem), poly-β-alanine powder and polyethylene powder, lauroyllysine, starch, tetrafluoroethylene polymer powders (Teflon®), hollow polymer microspheres such as those of polyvinylidene chloride/acrylonitrile, for instance Expancel® (Nobel Industrie) or of acrylic acid copolymer (such as Polytrap (Dow Corning)), acrylate copolymers, PMMA, 12-hydroxystearic acid oligomer stearate and silicone resin microbeads (for example Tospearls® from Toshiba), magnesium carbonate, magnesium hydrogen carbonate, and metal soaps derived from organic carboxylic acids containing from 8 to 22 carbon atoms and preferably from 12 to 18 carbon atoms, for example zinc stearate, magnesium stearate, lithium stearate, zinc laurate or magnesium myristate, and mixtures thereof.

For the purposes of the present invention, the organic fillers are different from the pigments.

They may also be particles comprising a copolymer, the said copolymer comprising trimethylol hexyl lactone. In particular, it may be a hexamethylene diisocyanate/trimethylol hexyl lactone copolymer. Such particles are especially commercially available, for example under the name Plastic Powder D-400 or Plastic Powder D-800 from the company Toshiki.

According to one embodiment, a composition of the invention may comprise at least one filler chosen from talc, silica, starch, clay, kaolin and perlite, and mixtures thereof.

One or more dispersants may be used, where appropriate, to protect the dispersed fillers or particles against aggregation or flocculation. They may be added independently of the solid fillers or particles or in the form of a colloidal dispersion of particles.

The concentration of dispersant is chosen so as to obtain satisfactory dispersion of the solid particles (without flocculation).

This dispersant may be a surfactant, an oligomer, a polymer or a mixture of several thereof, bearing one or more functionalities with strong affinity for the surface of the particles to be dispersed. In particular, poly(12-hydroxystearic acid) esters are used, such as poly(12-hydroxystearic acid) stearate with a molecular weight of about 750 g/mol, such as the product sold under the name Solsperse 21 000® by the company Avecia, esters of poly(12-hydroxystearic acid) with polyols such as glycerol or diglycerol, such as polyglyceryl-2 dipolyhydroxystearate (CTFA name) sold under the reference Dehymuls PGPH® by the company Henkel (or diglyceryl poly(12-hydroxystearate)), or alternatively poly(12-hydroxystearic acid), such as the product sold under the reference Arlacel P100 by the company Uniqema, and mixtures thereof.

As other dispersants that may be used in the composition of the invention, mention may be made of quaternary ammonium derivatives of polycondensated fatty acids, for instance Solsperse 17 000® sold by the company Avecia, and mixtures of polydimethylsiloxane/oxypropylene such as those sold by the company Dow Corning under the references DC 2-5185 and DC 2-5225 C.

Additional Common Cosmetic Ingredients

The composition according to the invention may also comprise any common cosmetic ingredient, which may be chosen especially from film-forming polymers, antioxidants, fragrances, preserving agents, moisturizers, self-tanning compounds, antiwrinkle active agents, emollients, hydrophilic or lipophilic active agents, free-radical scavengers, deodorants, sequestrants, film-forming agents and semicrystalline polymers, and mixtures thereof.

Needless to say, a person skilled in the art will take care to select the optional additional ingredients and/or the amount thereof such that the advantageous properties of the composition according to the invention are not, or are not substantially, adversely affected by the envisaged addition.

The compositions according to the invention may be in any common acceptable form for a cosmetic composition. They may thus be in the form of a suspension or a dispersion, especially of oil in water by means of vesicles; an optionally thickened or even gelled organic or oily solution; an oil-in-water, water-in-oil or multiple emulsion; a gel or a mousse; an oily or emulsified gel; a dispersion of vesicles, especially lipid vesicles; a two-phase or multiphase lotion; a spray; a lotion, a cream, a pomade, a soft paste, an ointment, a solid cast or moulded especially as a stick or in a dish, or a compacted solid.

A person skilled in the art may select the appropriate galenical form, and also the method for preparing it, on the basis of his general knowledge, taking into account firstly the nature of the constituents used, especially their solubility in the support, and secondly the intended use of the composition.

Preferably, the composition according to the invention comprises less than 3% and better still less than 1% by weight of water relative to the total weight of the composition. Even more preferably, the composition is totally anhydrous. The term "anhydrous" especially means that water is preferably not deliberately added to the composition, but may be present in trace amount in the various compounds used in the composition.

According to one preferred embodiment, the composition according to the invention is a lipstick.

According to one preferred embodiment, the composition according to the invention is in liquid form at 25° C., such as a lip gloss.

According to another embodiment, the composition is in solid form at 25° C. In the case of a lipstick, it may be a stick of lipstick or a lipstick cast in a dish, for example.

The term "solid" refers to a composition whose hardness, measured according to the following protocol, is greater than or equal to 30 $Nm^{-1}$ at a temperature of 20° C. and at atmospheric pressure (760 mmHg).

Protocol for Measuring the Hardness:

The hardness of the composition is measured according to the following protocol:

The stick of lipstick is stored at 20° C. for 24 hours before measuring the hardness.

The hardness may be measured at 20° C. via the "cheese wire" method, which consists in transversely cutting a wand of product, which is preferably a circular cylinder, by means of a rigid tungsten wire 250 μm in diameter, by moving the wire relative to the stick at a speed of 100 mm/minute.

The hardness of the samples of compositions of the invention, expressed in $Nm^{-1}$, is measured using a DFGHS2 tensile testing machine from the company Indelco-Chatillon.

The measurement is repeated three times and then averaged. The average of the three values read using the tensile testing machine mentioned above, noted Y, is given in grams. This average is converted into newtons and then divided by L which represents the longest distance through which the wire passes. In the case of a cylindrical wand, L is equal to the diameter (in meters).

The hardness is converted into $Nm^{-1}$ by the equation below:

$$(Y \times 10^{-3} \times 9.8)/L$$

For a measurement at a different temperature, the stick is stored for 24 hours at this new temperature before the measurement.

The compositions in accordance with the invention may be used for caring for or making up keratin materials such as the skin, the eyelashes, the eyebrows, the nails or the lips, and more particularly for making up the lips, the eyelashes and/or the face.

They may thus be in the form of a care and/or makeup product for bodily or facial skin, the lips, the eyelashes, the eyebrows or the nails; an antisun or self-tanning product; they may advantageously be in the form of a makeup composition, especially a mascara, an eyeliner, a lipstick, a lip gloss, a face powder, an eyeshadow, a foundation, a nail varnish or a nail-care product.

A subject of the invention is also a cosmetic process for treating keratin materials, especially bodily or facial skin, the lips, the nails and/or the eyelashes, comprising the application to the said materials of a cosmetic composition as defined previously.

This process according to the invention especially allows the said keratin materials, in particular the lips and/or the nails, to be cared for or made up, by applying a composition, especially a lipstick, a lip gloss, a nailcare product or a nail varnish according to the invention.

The invention is illustrated in greater detail in the following preparation examples.

EXAMPLE 1

Preparation of a Poly(Isobornyl Acrylate/Isobornyl Methacrylate/Isobutyl Acrylate/Acrylic Acid) Copolymer 300 g of isododecane are placed in a 1 liter reactor, and the temperature is then increased so as to go from room temperature (25° C.) to 90° C. over 1 hour.

105 g of isobornyl methacrylate, 105 g of isobornyl acrylate and 1.8 g 2,5-bis(2-ethylhexanoyl-peroxy)-2,5-dimethylhexane (Trigonox® 141 from Akzo Nobel) are then added, at 90° C. over 1 hour.

The mixture is maintained at 90° C. for 1 hour 30 minutes.

75 g of isobutyl acrylate, 15 g of acrylic acid and 1.2 g of 2,5-bis(2-ethylhexanoylperoxy)-2,5-dimethylhexane are then added to the preceding mixture, still at 90° C. and over 30 minutes.

The mixture is maintained at 90° C. for 3 hours, and the whole is then cooled.

A solution with a 50% active material content of copolymer in isododecane is obtained.

A copolymer is obtained comprising a first poly(isobornyl acrylate/isobornyl methacrylate) block with a Tg of 128° C., a second poly(isobutyl acrylate/acrylic acid) block with a Tg of −9° C., and an intermediate block, which is an isobornyl acrylate/isobornyl methacrylate/isobutyl acrylate/acrylic acid random copolymer.

The Tg of the copolymer is 74° C.

These are theoretical Tg values calculated by Fox's law.

EXAMPLE 2

Preparation of the Siloxane Resins

The following resins are used:

MQ resin=an MQ resin of formula $M_{0.43}Q_{0.57}$ and of $M_n$=3230 dissolved in xylene to a proportion of 70.8% by weight of solids. The MQ resin was manufactured according to the techniques described by Daudt in U.S. Pat. No. 2,676,182.

T Propyl resin=a propyl silsesquioxane resin at 74.8% by weight in toluene. The propyl silsesquioxane resin was obtained by hydrolysis of propyltrichlorosilane.

Preparation of the $MQT^{Pr}$ Resins

An MQ resin, a T propyl resin, xylene and 1M KOH in water in the proportions presented in Table 1 are introduced into a 3-necked flask equipped with a stirrer, a temperature probe and Dean-Stark apparatus mounted with a condenser. Xylene is pre-introduced into the Dean-Stark apparatus so as to ensure maintenance of a level of solids of 50% in the reactor. The mixture in the reactor is refluxed (between 100 and 140° C.) for at least 3 hours. Any water formed in the reaction mixture is continuously removed and trapped in the form of an azeotrope in the Dean-Stark apparatus. After refluxing for 3 hours, the water is removed from the apparatus and heating is continued for a further 30 minutes. After cooling the mixture, an excess of acetic acid is added to neutralize the KOH in the mixture. The mixture is then filtered to remove the salts formed, by passing it through a filter under pressure. Solvent exchange is performed by heating the mixture in a rotary evaporator under vacuum. After removing the majority of the xylene, decamethylcyclopentasiloxane (or isododecane) is added while continuing to remove any residual aromatic solvent. The structures of the resulting siloxane resins are characterized by $^{29}Si$ NMR and GPC, and the results are summarized in Table 2 below.

TABLE 1

| Example # | Mass ratio of MQ/$T^{Pr}$ resins added | Weight % of MQ resin | Weight % of T propyl resin | Weight % of xylene | Weight % of 1M KOH | Weight % of acetic acid |
|---|---|---|---|---|---|---|
| 1-a | (85:15) | 59.4 | 10.5 | 29.1 | 0.9 | 0.2 |
| 1-b | (50:50) | 34.9 | 34.8 | 29.1 | 0.9 | 0.2 |
| 1-c | (30:70) | 20.9 | 48.8 | 29.2 | 0.9 | 0.2 |
| 1-d | (95:5) | 67.1 | 3.5 | 28.3 | 0.9 | 0.2 |
| 1-e | (100:0) | 69.3 | 0 | 28.8 | 0.9 | 0.2 |

TABLE 2

| Example # | Resin structure according to NMR characterization | Weight % of OH | Mn | Mw | Mw/Mn |
|---|---|---|---|---|---|
| MQ resin | $M^{0.43}Q^{0.57}$ | | 3230 | 1516 | 4.7 |
| T Propyl resin | $T^{Pr}_{1.0}$ | 7.0 | 3470 | 11 400 | 3.3 |
| 1-a | $M_{0.374}Q_{0.529}:T^{Pr}_{0.097}$ | 1.4 | 5880 | 271 000 | 46.1 |
| 1-b | $M_{0.248}Q_{0.341}:T^{Pr}_{0.412}$ | 2.1 | 6640 | 3 860 000 | 581.3 |
| 1-c | $M_{0.162}Q_{0.217}:T^{Pr}_{0.621}$ | 1.5 | 7600 | 25 300 000 | 3329 |
| 1-d | $M_{0.419}Q_{0.5485}:T^{Pr}_{0.03}$ | 1.5 | | | |
| 1-e | MQ | 1.7 | 5200 | 28 900 | 5.6 |

EXAMPLES 3 to 5

Liquid Lipsticks

The following liquid lipstick compositions were prepared:

| Compound | Composition 3 according to the invention (weight %) | Composition 4 according to the invention (weight %) | Composition 5 according to the invention (weight %) |
|---|---|---|---|
| Supramolecular compound prepared from Jarcol 16 (51.7% in a 90/10 isododecane/ethanol | 80 | 80 | 80 |

-continued

| Compound | Composition 3 according to the invention (weight %) | Composition 4 according to the invention (weight %) | Composition 5 according to the invention (weight %) |
|---|---|---|---|
| mixture) (Supramolecular compound No. 9 prepared above) | | | |
| Pentaerythritol 20/benzoic acid 4/isostearic acid 56/isophthalic acid 20 (as prepared in Example 2 of EP-A-1 870 082) | 19 | — | — |
| Acrylic copolymer as a dispersion in isododecane with styrene/isoprene copolymer (Kraton G1701) (MEXOMER PAP From Chimex) | — | 19 | — |
| Poly(isobornyl methacrylate-co-isobornyl acrylate-co-isobutyl acrylate-co-acrylic acid) at 50% active material in 50% of isododecane, as prepared according to Example 1 above | — | — | 19 |
| Red 7 (Unipure Red LC 3079 OR from LCW (Sensient) | 1 | 1 | 1 |
| Total: | 100 | 100 | 100 |

Preparation Protocol:

In a first stage, the pigments are ground in a three-roll mill in part of the oily phase.

The rest of the liposoluble ingredients are then mixed together at a temperature of about 50° C. (above the melting point of the solid fatty substances (paste or wax) present in the composition) with stirring using a Rayneri blender.

The ground material is then added to the mixture and is stirred to homogenize thoroughly. The fluid is then allowed to cool to room temperature and is conditioned in a heating bag with an applicator.

The various compositions obtained are homogeneous.

After applying the compositions to the lips, the following results are observed:

For composition 3 comprising a polycondensate, the deposit formed is glossy, does not transfer and is sparingly tacky.

For composition 4 comprising a non-aqueous dispersion, the deposit formed is glossy and non-tacky.

For composition 5 comprising a block ethylenic copolymer, the deposit formed is glossy and non-tacky.

EXAMPLES 6 and 7

Liquid Lipsticks

The following liquid lipstick compositions, containing a silicone resin, were prepared:

| Compound | Composition 6 according to the invention (weight %) | Composition 7 according to the invention (weight %) |
|---|---|---|
| Supramolecular compound prepared from Jarcol 16 (51.7% in a 90/10 isododecane/ethanol mixture) (Supramolecular compound No. 9 prepared above) | 70 | 70 |
| MQ-T Propyl resin (30:70) at 70.3% in isododecane, as prepared in Example 1-C above (Dow Corning) | 29 | — |
| Trimethyl siloxysilicate (SR 1000 from Momentive) | — | 29 |
| Red 7 (Unipure Red LC 3079 OR from LCW (Sensient)) | 1 | 1 |
| Total: | 100 | 100 |

Preparation Protocol:

In a first stage, the pigments are ground in a three-roll mill in part of the oily phase.

The rest of the liposoluble ingredients are then mixed together at a temperature of about 50° C. (above the melting point of the solid fatty substances (paste or wax) present in the composition) with stirring using a Rayneri blender.

The ground material is then added to the mixture and is stirred to homogenize thoroughly. The fluid is then allowed to cool to room temperature and is conditioned in a heating bag with an applicator.

The various compositions obtained are homogeneous.

After applying the compositions to the lips, the following results are observed:

For composition 6 comprising a silicone resin of MQT type, the deposit formed is very glossy and non-tacky.

For composition 7 comprising a silicone resin of MQ type, the deposit formed is very glossy and non-tacky.

EXAMPLES 8 and 9

Liquid Lipsticks

The following liquid lipstick compositions, containing a thickener capable of establishing hydrogen interactions, were prepared:

| Compound | Composition 8 according to the invention (weight %) | Composition 9 according to the invention (weight %) |
|---|---|---|
| Supramolecular compound prepared from Jarcol 16 (51.7% in a 90/10 isododecane/ethanol mixture) (Supramolecular compound No. 9 prepared above) | 90 | 90 |
| Ethylenediamine/stearyl dimer dilinoleate copolymer (Uniclear 100 VG from Arizona Chemicals) | 9 | — |
| Nylon-611/dimethicone copolymer (Dow Corning 2-8179 Gellant from Dow Corning) | — | 9 |

| Compound | Composition 8 according to the invention (weight %) | Composition 9 according to the invention (weight %) |
|---|---|---|
| Red 7 (Unipure Red LC 3079 OR from LCW (Sensient) | 1 | 1 |
| Total: | 100 | 100 |

Preparation Protocol:

In a first stage, the pigments are ground in a three-roll mill in part of the oily phase.

The rest of the liposoluble ingredients are then mixed together at a temperature of about 50° C. (above the melting point of the solid fatty substances (paste or wax) present in the composition) with stirring using a Rayneri blender.

The ground material is then added to the mixture and is stirred to homogenize thoroughly. The fluid is then allowed to cool to room temperature and is conditioned in a heating bag with an applicator.

The various compositions obtained are homogeneous.

After applying the compositions to the lips, the following results are observed:

For composition 8 comprising a polyamide, the deposit formed is glossy.

For composition 9 comprising a silicone polyamide, the deposit formed is glossy and non-tacky.

EXAMPLES 10

Liquid Lipsticks

The following liquid lipstick composition, containing a silicone elastomer, was prepared:

| Compound | Composition 10 according to the invention (weight %) |
|---|---|
| Supramolecular compound prepared from Jarcol 16 (51.7% in a 90/10 isododecane/ethanol mixture) (Supramolecular compound No. 9 prepared above) | 89 |
| Dimethicone (and) dimethicone crosspolymer (Dow Corning 9041 Silicone Elastomer Blend from Dow Corning) | 10 |
| Red 7 (Unipure Red LC 3079 OR from LCW (Sensient)) | 1 |
| Total: | 100 |

Preparation Protocol:

In a first stage, the pigments are ground in a three-roll mill in part of the oily phase.

The rest of the liposoluble ingredients are then mixed together at a temperature of about 50° C. (above the melting point of the solid fatty substances (paste or wax) present in the composition) with stirring using a Rayneri blender.

The ground material is then added to the mixture and is stirred to homogenize thoroughly. The fluid is then allowed to cool to room temperature and is conditioned in a heating bag with an applicator.

The composition obtained is homogeneous. After applying the composition to the lips, a glossy and non-tacky deposit is obtained (the deposit is glossy, but slightly less glossy than the deposits obtained with compositions 1 to 9).

EXAMPLES 11 and 12

Solid Lipsticks

The following solid lipstick compositions, containing a silicone resin, were prepared:

| Compounds | Composition 11 according to the invention (weight %) | Composition 12 according to the invention (weight %) |
|---|---|---|
| Supramolecular compound prepared from Jarcol 24 (51.5% in a 90/10 isododecane/ethanol mixture) (Supramolecular compound No. 12 prepared above) | 30.68 | — |
| Supramolecular compound prepared from diisostearyl malate (50.8% in isododecane) (Supramolecular compound No. 8 prepared above) | — | 30.68 |
| Trimethyl siloxysilicate (SR 1000 from Momentive) | 25 | 25 |
| Silica (Solesphere H 51 from AGC SI-TECH) | 1 | 1 |
| Disteardimonium hectorite (and) propylene carbonate (Bentone Gel ISD V from Elementis) | 5.95 | 5.95 |
| Isododecane | qs 100 | qs 100 |
| Isopropyl alcohol | 1 | 1 |
| Polyethylene wax (Performalene 500-L Polyethylene from New Phase Technologies) | 9.20 | 9.20 |
| C30-50 alcohols (Performacol 550-L Alcohol from New Phase Technologies) | 2.25 | 2.25 |
| Red 7 (Unipure Red LC 3079 OR from LCW (Sensient)) | 5 | 5 |
| Total: | 100 | 100 |
| HARDNESS | 57.5 Nm$^{-1}$ | 52.6 Nm$^{-1}$ |

Preparation Protocol:

In a first stage, the silicone resin was dispersed in part of the isododecane with stirring using a Rayneri blender, and the disteardimonium hectorite was then added. The pigments were then ground in the mixture thus prepared, using a three-roll mill, and the rest of the isododecane was then added to the ground material. Stirring of the mixture was continued using a Rayneri blender.

The supramolecular compound and isopropyl alcohol were placed in a heating pan at room temperature. Once the mixture was homogeneous, the silica was added and mixing was continued for a further 10 minutes. The pigmentary ground material prepared previously was then added to the mixture. Finally, the waxes were added and the whole was heated at 98° C. for 30 minutes with stirring using a Rayneri blender.

The composition was then poured into moulds preheated to 42° C. to produce sticks 8 mm in diameter, which were then left to cool in a freezer for the time necessary to achieve efficient work-hardening (about one hour). The sticks were then left to stand at room temperature for 24 hours.

Protocol to be Confirmed

The various compositions obtained are homogeneous and the sticks obtained are easy to apply (slippery on application).

After applying the compositions to the lips, the following results are observed:

For each of the compositions 11 and 12, the makeup deposits obtained are uniform and comfortable, and do not transfer.

EXAMPLES 13 and 14

Liquid Lipsticks

The following liquid lipstick compositions, containing a silicone resin, were prepared:

| Compounds | Composition 13 according to the invention (weight %) | Composition 14 according to the invention (weight %) |
|---|---|---|
| Supramolecular compound prepared from Jarcol 24 (51.5% in a 90/10 isododecane/ethanol mixture) (Supramolecular compound No. 12 prepared above) | 28.66 | — |
| Supramolecular compound prepared from diisostearyl malate (50.8% in isododecane) (Supramolecular compound No. 8 prepared above) | — | 28.66 |
| Trimethyl siloxysilicate (SR 1000 from Momentive) | 17 | 17 |
| Disteardimonium hectorite (and) propylene carbonate (Bentone Gel ISD V from Elementis) | 25 | 25 |
| Isododecane | qs 100 | qs 100 |
| Lauroyllysine (Amihope LL from Ajinomoto) | 1.5 | 1.5 |
| Red 7 (Unipure Red LC 3079 OR from LCW (Sensient)) | 5 | 5 |
| Total: | 100 | 100 |

Preparation Protocol:

In a first stage, the silicone resin was dispersed in part of the isododecane with stirring using a Rayneri blender, and the disteardimonium hectorite was then added. The pigments and the lauroyllysine were then ground in the mixture thus prepared, in a three-roll mill, and the rest of the isododecane was then added to the ground material. Stirring of the mixture was continued using a Rayneri blender.

The preceding mixtures were placed in a heating pan at room temperature. The supramolecular compound was then added and the mixture was maintained at 50° C. for 15 minutes with stirring. Once the mixture was homogeneous, it was cooled with continued stirring. The compositions were then conditioned in isododecane-leaktight heating bags.

The various compositions obtained are homogeneous.

After applying the compositions to the lips, the following results are observed:

For each of the compositions 13 and 14, the makeup deposits obtained are homogeneous, comfortable, do not transfer and show a good level of remanence of the colour, especially grease resistance.

The invention claimed is:

1. A cosmetic composition comprising, in a cosmetically acceptable medium:
   (i) a supramolecular compound obtained by reacting:
   an oil comprising a nucleophilic reactive function selected from the group consisting of OH and $NH_2$, and
   a junction group, which establishes a hydrogen bond with a partner junction group, each pairing of the junction group involving at least three hydrogen bonds, wherein the junction group comprises an isocyanate or imidazole reactive function, which reacts with the nucleophilic reactive function of the oil, and a unit of formula (I) or (II):

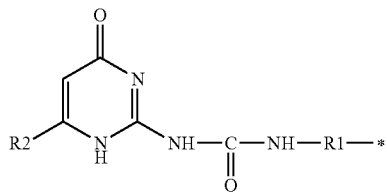

wherein:
R1 and R3 are each independently a divalent carbon-based radical selected from the group consisting of a linear or branched $C_1$-$C_{32}$ alkyl group, a $C_4$-$C_{16}$ cycloalkyl group, and a $C_4$-$C_{16}$ aryl group; optionally comprising 1 to 8 heteroatoms selected from the group consisting of O, N, S, F, Si, and P; and/or optionally substituted with an ester function, an amide function, or a $C_1$-$C_{12}$ alkyl radical; or a mixture of these groups;

R2 is a hydrogen atom or a linear, branched, or cyclic, saturated or unsaturated, optionally aromatic, $C_1$-$C_{32}$ carbon-based radical, optionally comprising at least one heteroatom selected from the group consisting of O, N, S, F, Si and P;

wherein the oil comprises at least one selected from the group consisting of:
a linear, branched, or cyclic, saturated or unsaturated fatty alcohol comprising 6 to 50 carbon atoms, an OH, and optionally an $NH_2$;
an ester or ether comprising a free OH group;
a hydroxylated natural oil, a modified natural oil, a plant oil, or any combination thereof; and
(ii) at least one ingredient selected from the group consisting of:
a silicone elastomer;
a polyester obtained by reacting a tetraol comprising from 4 to 10 carbon atoms,
a saturated, linear or branched monocarboxylic acid comprising from 9 to 23 carbon atoms,
a cyclic dicarboxylic acid comprising from 6 to 12 carbon atoms, and an aromatic monocarboxylic acid comprising from 7 to 11 carbon atoms;
a film-forming agent, which is a silicone resin or film-forming polymer,
a structuring agent selected from the group consisting of a semicrystalline polymer and a semicrystalline thickener comprising at least one a group capable of establishing hydrogen interactions selected from the group consisting of a polymeric thickener and an organogelling agent.

2. The composition of claim 1, wherein the oil comprises at least one selected from the group consisting of:
a saturated or unsaturated, linear or branched C6-C50 monoalcohol;

a saturated or unsaturated, linear or branched C6-C50 diol;
a saturated or unsaturated, linear or branched C6-C50 triol;
a pentaerythritol partial ester;
a dipentaerythritol diester, triester, tetraester, or pentaester;
a trimethylolpropane monoester or diester;
a bis(trimethylolpropane) monoester, diester, or triester;
a partial monoester or polyester of glycerol or a polyglycerol;
a propylene glycol monoester;
a diol dimer monoester;
a glycerol ether;
an ester between a hydroxylated monocarboxylic, dicarboxylic, or tricarboxylic acid and a monoalcohol;
a triglyceryl ester comprising an OH;
a hydrogenated or non-hydrogenated castor oil, or a derivative thereof; and
a modified epoxidized oil, wherein the modification comprises opening the epoxy function, to obtain a diol.

3. The composition of claim 1, wherein the oil has a refractive index of greater than or equal to 1.46 at 25° C.

4. The composition of claim 1, wherein the oil has a molar mass (Mw) from 150 and 6000 g/mol.

5. The composition of claim 1, wherein the oil is selected from the group consisting of:
a linear, branched, or cyclic, saturated or unsaturated fatty alcohol comprising 6 to 50 carbon atoms, an OH, and optionally an $NH_2$; and
an ester of a hydroxylated dicarboxylic acid with a monoalcohol.

6. The composition of claim 1, wherein, in the junction group, the radical R1 is:
a linear or branched, divalent C2-C12 alkylene group; or
a divalent C4-C12 cycloalkylene or arylene group.

7. The composition of claim 1, wherein, in the junction group, the radical R2 is H, or a radical comprising at least one selected from the group consisting of: a $C_1$-$C_{32}$ alkyl group; a $C_4$-$C_{12}$ cycloalkyl group; a $C_4$-$C_{12}$ aryl group; a ($C_4$-$C_{12}$) aryl ($C_1$-$C_{18}$) alkyl group; a $C_1$-$C_4$ alkoxy group; an arylalkoxy group; and a $C_4$-$C_{12}$ heterocycle, and optionally substituted with at least one selected from the group consisting of an amino function, an ester function, and a hydroxyl function.

8. The composition of claim 1, wherein, in the junction group, the radical R3 is a divalent radical —R'3-O—C(O)—NH—R'4-,
wherein R'3 and R'4 are each independently a divalent carbon-based radical selected from the group consisting of a linear or branched $C_1$-$C_{32}$ alkyl group, a $C_4$-$C_{16}$ cycloalkyl group, and a $C_4$-$C_{16}$ aryl group; or a mixture thereof.

9. The composition of claim 1, wherein, in the junction group, (a) in formula (I), the following are present:
$R_1$ is -isophorone- and R2 is methyl;
$R_1$ is —$(CH_2)_6$— and R2 is methyl;
$R_1$ is —$(CH_2)_6$— and R2 is isopropyl; or
$R_1$ is 4,4'-methylenebiscyclohexylene and R2 is methyl, or alternatively (b) in formula (II),
R1 is the -isophorone- radical, R2 is methyl, and R3 is —$(CH_2)_2$OCO—NH-isophorone.

10. The composition of claim 1, wherein the junction group is of formula (I') or formula (II'):

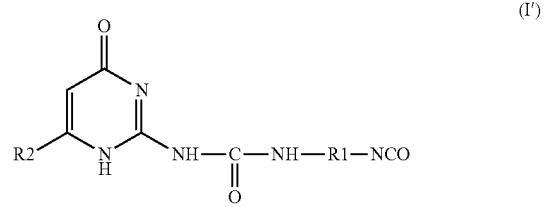

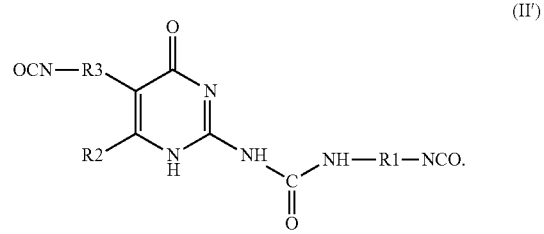

11. The composition of claim 1, wherein the junction group is selected from the group consisting of formulae:

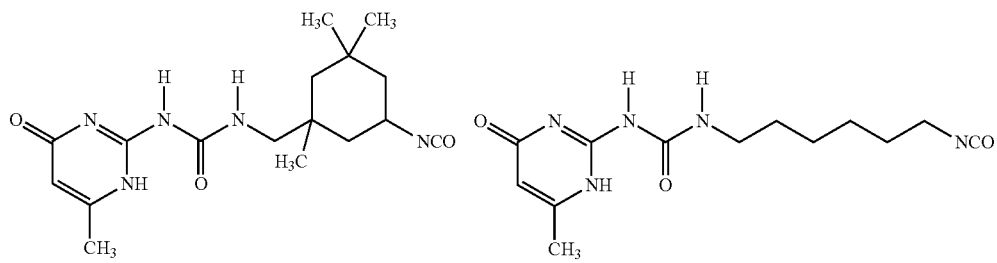

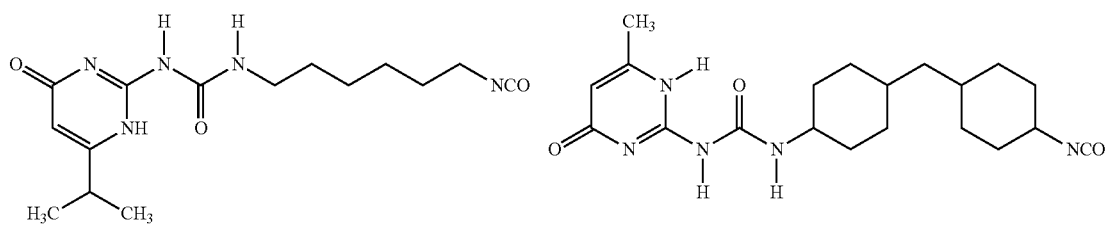

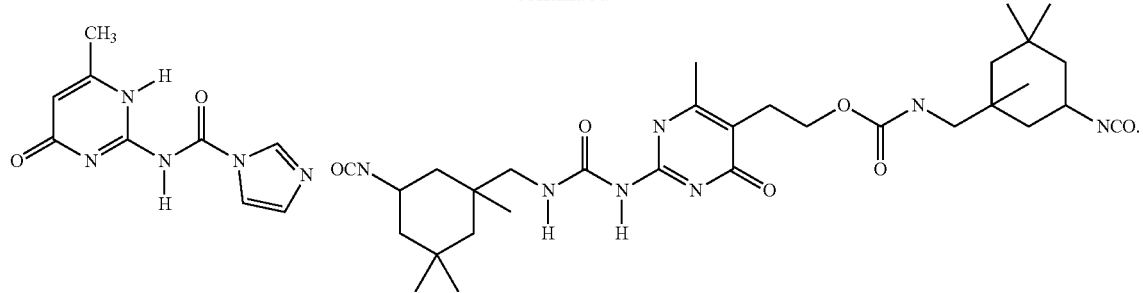
12. The composition of claim 1, wherein the supramolecular compound has a structure selected from the group consisting of:
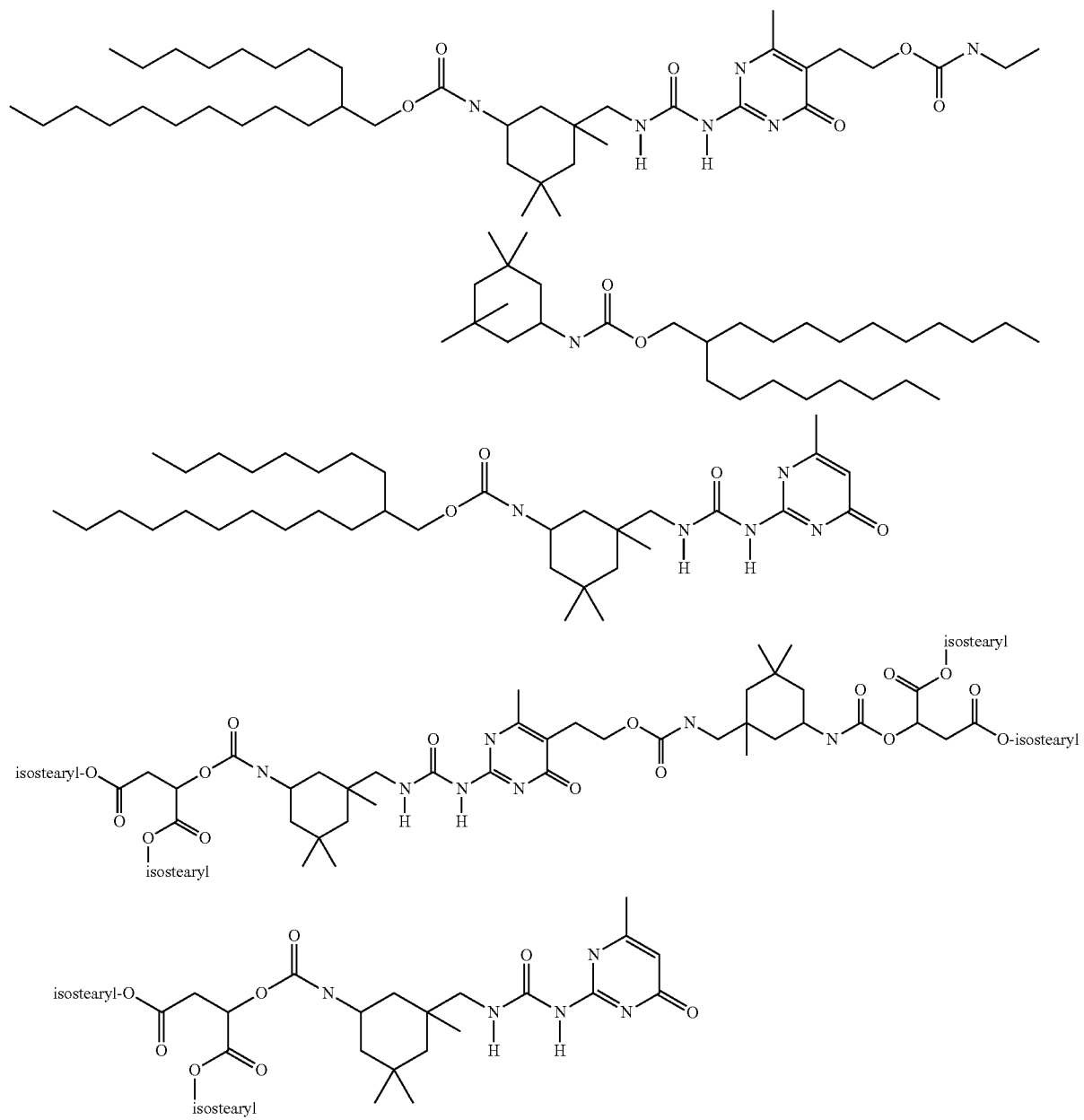

137 138
-continued
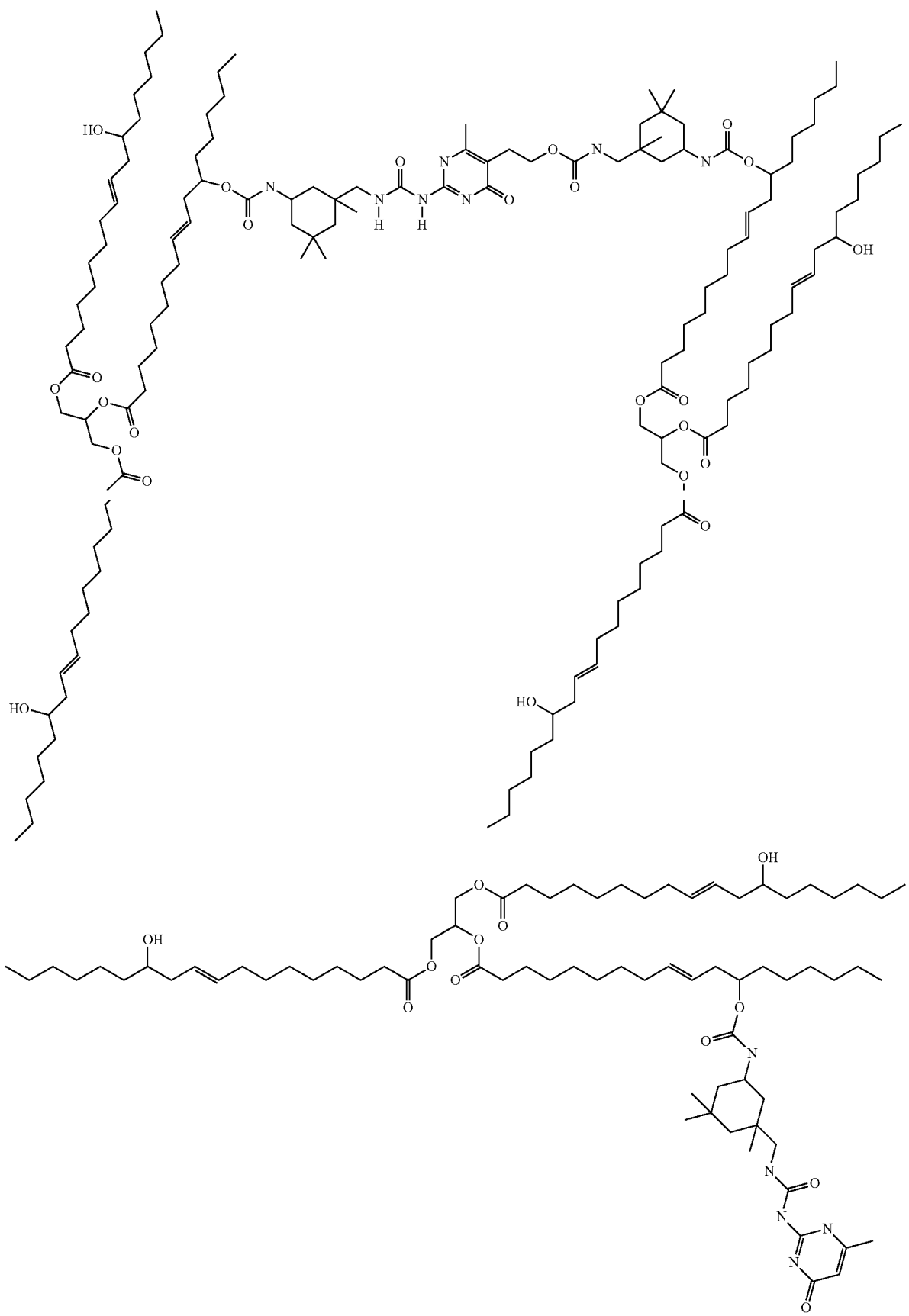

-continued

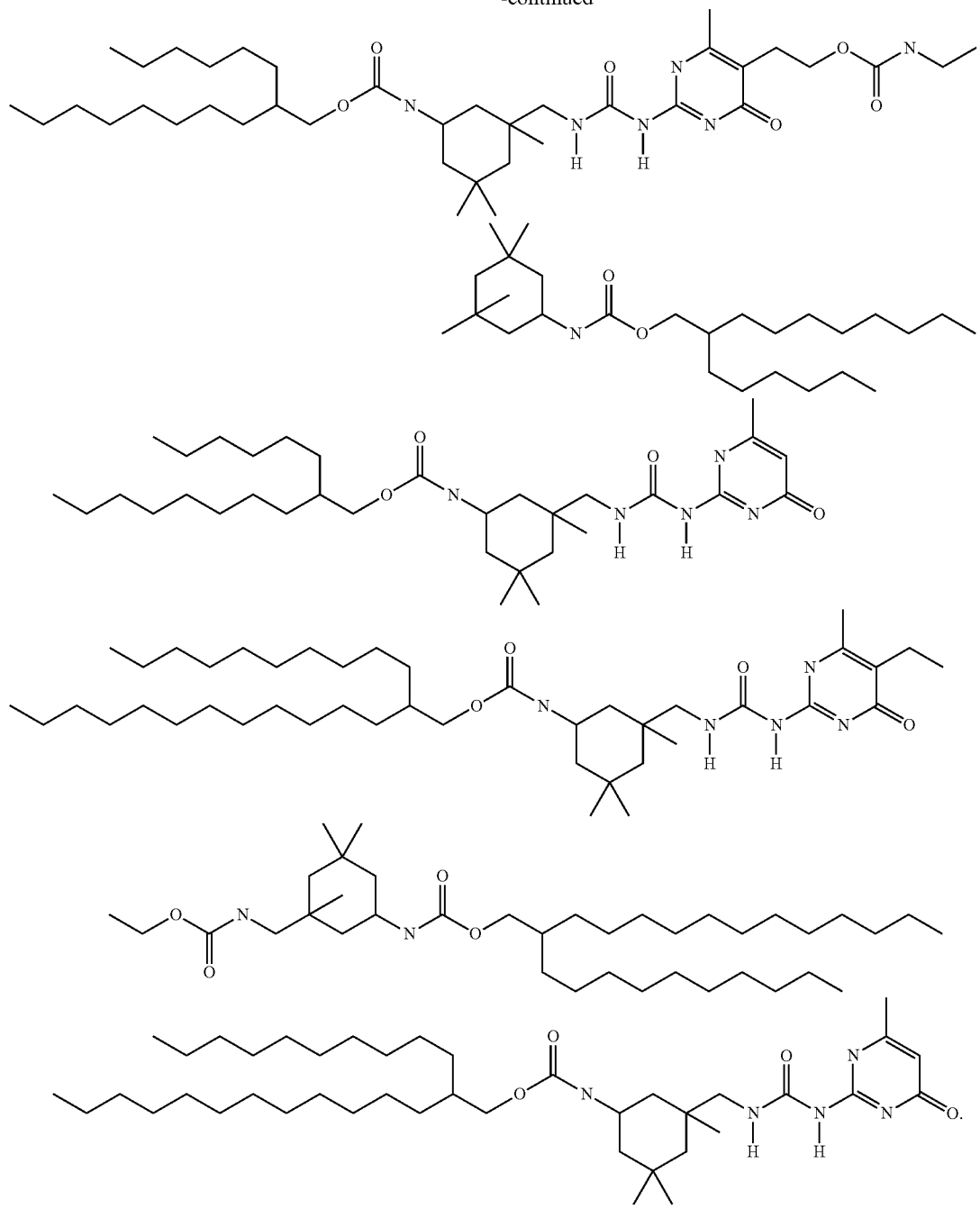

13. The composition of claim 1, wherein the number-average molecular mass (Mn) of the supramolecular compound is from 180 to 8000.

14. The composition of claim 1, wherein the supramolecular compound is present in the composition in an amount from 5% to 95% by weight, relative to a total weight of the composition.

15. The composition of claim 1, wherein the ingredient is an organopolysiloxane elastomer obtained via:
 a crosslinking addition reaction of diorganosiloxane comprising a hydrogen bonded to silicon and of a diorganopolysiloxane comprising an ethylenically unsaturated group bonded to silicon;
 a dehydrogenation crosslinking condensation reaction between a diorganopolysiloxane comprising a hydroxyl end group and a diorganopolysiloxane comprising a hydrogen bonded to silicon;
 a crosslinking condensation reaction of a diorganopolysiloxane comprising a hydroxyl end group and of a hydrolysable organopolysilane;
 a thermal crosslinking of an organopolysiloxane; or
 a crosslinking of organopolysiloxane by high-energy radiation.

16. The composition of claim 1, wherein the ingredient is at least one silicone resin selected from the group consisting of:
 a) a MQ resin;

b) a T resin; and
c) a MQT resin.

17. The composition of claim 1, wherein the ingredient is a film-forming polymer selected from the group consisting of:
(I) a film-forming block ethylenic polymer comprising a first and second block, wherein the second block is obtained from acrylic acid and isobutyl acrylate and the first block is obtained from isobornyl acrylate and isobornyl methacrylate;
(II) a vinyl polymer comprising a carbosiloxane dendrimer unit comprising a carbosiloxane dendritic structure of formula (I):

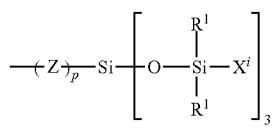

wherein Z is a divalent organic group, "p" is 0 or 1, $R^1$ is an aryl or alkyl group comprising 1 to 10 carbon atoms, and $X^i$ is a silylalkyl group of formula (II):

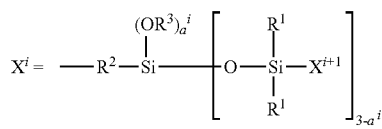

wherein $R^1$ is an aryl or alkyl group comprising 1 to 10 carbon atoms, $R^2$ is an alkylene group comprising 1 to 10 carbon atoms, $R^3$ is an alkyl group comprising 1 to 10 carbon atoms, and $X^{i+1}$ is a hydrogen atom, an aryl group comprising up to 10 carbon atoms, an alkyl group comprising up to 10 carbon atoms, or a silylalkyl group $X^i$, wherein the power "i" is an integer from 1 to 10 indicating the generation of the starting silylalkyl group in each carbosiloxane dendrite structure with a value of 1 for the group $X^i$ in formula (I), and the index "a" is an integer from 0 to 3; and
(III) a dispersion of acrylic or vinyl radical homopolymer or copolymer particles dispersed in a liquid fatty phase, wherein the polymer particles in dispersion are acrylic polymers or copolymers which are insoluble in water-soluble alcohol.

18. The composition of claim 1, wherein the ingredient is a semicrystalline polymer selected from the group consisting of:
a homopolymer or copolymer comprising a unit obtained from polymerizing a monomer comprising a crystallizable hydrophobic side chain;
a polymer comprising, in the backbone, a crystallizable block;
a polycondensate of an aliphatic, an aromatic, or an aliphatic/aromatic polyester;
at least one selected from the group consisting of an ethylene homopolymer, a propylene homopolymer, and an ethylene/propylene copolymer prepared via metallocene catalysis.

19. The composition of claim 1, wherein the ingredient is a thickener, which establishes H bonds, selected from the group consisting of:
(i) a polymer having a weight-average molecular mass of less than 100 000, and comprising a) a polymer backbone comprising hydrocarbon repeating units comprising a heteroatom, and optionally comprising b) at least one selected from the group consisting of a pendent fatty chain and a terminal fatty chain, optionally functionalized, comprising from 6 to 120 carbon atoms, and linked to the hydrocarbon; and
(ii) a silicone polyamide.

20. The composition of claim 1, further comprising:
at least one additive selected from the group consisting of a volatile oil, a nonvolatile oil, a dyestuff, a pasty fatty substance, a wax, and a filler.

21. The composition of claim 1, in the form of a composition for caring for and/or making up bodily or facial skin, lips, eyelashes, eyebrows, or nails; an antisun or self-tanning product.

22. A process for treating a keratin material, the process comprising:
applying the cosmetic composition of claim 1 to a keratin material.

* * * * *